US006990422B2

(12) United States Patent
Laletin et al.

(10) Patent No.: US 6,990,422 B2
(45) Date of Patent: Jan. 24, 2006

(54) METHOD OF ANALYZING THE TIME-VARYING ELECTRICAL RESPONSE OF A STIMULATED TARGET SUBSTANCE

(75) Inventors: William H. Laletin, Slidell, LA (US); Kurt Salloux, Topanga, CA (US)

(73) Assignee: World Energy Labs (2), Inc., Torrance, CA (US)

( * ) Notice: Subject to any disclaimer, the term of this patent is extended or adjusted under 35 U.S.C. 154(b) by 0 days.

(21) Appl. No.: 10/666,567

(22) Filed: Sep. 19, 2003

(65) Prior Publication Data

US 2004/0128088 A1    Jul. 1, 2004

Related U.S. Application Data

(63) Continuation-in-part of application No. 10/443,230, filed on May 21, 2003, which is a continuation-in-part of application No. 09/122,181, filed on Jul. 24, 1998, now abandoned, and a continuation-in-part of application No. PCT/US97/050002, filed on Mar. 27, 1997.

(60) Provisional application No. 60/054,466, filed on Jul. 25, 1997, provisional application No. 60/014,159, filed on Mar. 27, 1996.

(51) Int. Cl.
*G06F 19/00* (2006.01)

(52) U.S. Cl. ............... 702/109; 702/117; 702/124; 702/125; 379/88.07; 708/100; 324/425; 320/116; 320/124

(58) Field of Classification Search ............ 702/117, 702/124, 125, 109; 379/88.07; 708/100; 73/1.01, 1.11; 324/425; 320/116, 124, 1
See application file for complete search history.

(56) References Cited

U.S. PATENT DOCUMENTS 2,354,877 A     8/1944  Peters .......................... 320/5
2,662,211 A    12/1953  Marko et al. ................. 324/29

(Continued)

FOREIGN PATENT DOCUMENTS

WO    WO 97/36182    10/1997

OTHER PUBLICATIONS

Lau et al., 'DSP Based Fuzzy Controlled 2-Wheeler Forward Converter', Nov. 1995, IEEE Article, pp. 440-445.*

*Primary Examiner*—Marc S. Hoff
*Assistant Examiner*—Elias Desta
(74) *Attorney, Agent, or Firm*—Mark S. Leonardo; Joseph P. Quinn; Brown Rudnick Berlack Israels

(57) ABSTRACT

A time varying electrical excitation(s) is applied to a system containing biologic and/or non-biologic elements, whereupon the time-varying electrochemical or electrical response is detected and analyzed. For biologic specimens, the presence, activity, concentration or relative quantity, and certain inherent characteristics of certain target substances (hereinafter referred to as "target analytes") within, or comprising, the specimen of interest may be determined by measuring either the current response induced by a voltage-mode excitation, or the voltage response induced by a current-mode excitation. Labeling or marker techniques may be employed, whereby electrochemically active auxiliary molecules are attached to the substance to be analyzed, in order to facilitate or enhance the electrochemical or electrical response. The method may also be employed to test non-biologic systems comprising an electrochemical cell or a battery of cells, wherein complex pulse type excitation signals are applied to the cell and the resultant time varying polarization voltage information is extracted and analyzed to determine at least one characteristic of the cell(s) condition or state.

24 Claims, 59 Drawing Sheets

Galvanodynamic Test System

U.S. PATENT DOCUMENTS

| | | | |
|---|---|---|---|
| 2,853,676 A | 9/1958 | Ellis .......................... 324/29.5 |
| 3,621,359 A | 11/1971 | Schnegg ..................... 320/43 |
| 3,626,270 A | 12/1971 | Burkett et al. ................ 320/35 |
| 3,808,487 A | 4/1974 | Feuillade .................... 320/21 |
| 3,873,911 A | 3/1975 | Champlin ................. 324/29.5 |
| 3,909,708 A | 9/1975 | Champlin ................. 324/29.5 |
| 3,931,506 A * | 1/1976 | Borrelli et al. ............. 714/724 |
| 3,984,762 A | 10/1976 | Dowgiallo, Jr. ............ 324/29.5 |
| 3,997,834 A | 12/1976 | Winter et al. .............. 324/29.5 |
| 4,053,824 A | 10/1977 | Dupuis et al. ............. 324/29.5 |
| 4,080,560 A | 3/1978 | Abert ....................... 324/29.5 |
| 4,181,885 A | 1/1980 | Gosser et al. ............... 324/428 |
| 4,204,162 A | 5/1980 | Froidevaux ................ 324/430 |
| 4,259,639 A | 3/1981 | Renirie ..................... 324/430 |
| 4,295,097 A | 10/1981 | Thompson et al. ......... 324/429 |
| 4,305,039 A | 12/1981 | Steuernagel et al. ........ 324/425 |
| 4,321,541 A | 3/1982 | Nishizuka .................. 324/426 |
| 4,360,779 A | 11/1982 | Peled et al. ................ 324/434 |
| 4,361,809 A | 11/1982 | Bil et al. ................... 324/426 |
| 4,376,485 A | 3/1983 | Shah ........................ 209/575 |
| 4,388,618 A | 6/1983 | Finger ....................... 340/636 |
| 4,413,221 A | 11/1983 | Benjamin et al. ............ 320/48 |
| 4,433,294 A | 2/1984 | Windebank ................ 324/426 |
| 4,433,295 A | 2/1984 | Zaugg ........................ 324/429 |
| 4,453,129 A | 6/1984 | Lissalde et al. ............ 324/429 |
| 4,659,994 A | 4/1987 | Poljak ...................... 324/426 |
| 4,697,134 A | 9/1987 | Burkum et al. .............. 320/48 |
| 4,707,795 A | 11/1987 | Alber et al. ................ 364/550 |
| 4,719,428 A | 1/1988 | Liebermann ................ 324/436 |
| 4,728,877 A | 3/1988 | Adamson ..................... 320/21 |
| 4,743,855 A | 5/1988 | Randin et al. .............. 324/430 |
| 4,758,779 A * | 7/1988 | Thong ....................... 324/72.5 |
| 4,816,768 A | 3/1989 | Champlin ................... 324/428 |
| 4,825,170 A | 4/1989 | Champlin ................... 324/436 |
| 4,829,225 A | 5/1989 | Podrazhansky et al. ....... 320/14 |
| 4,849,700 A | 7/1989 | Morioka et al. ............ 324/427 |
| 4,876,513 A | 10/1989 | Brilmyer et al. ............. 324/427 |
| 4,881,038 A | 11/1989 | Champlin ................... 324/426 |
| 4,912,416 A | 3/1990 | Champlin ................... 324/430 |
| 4,931,367 A | 6/1990 | Brecht et al. ................. 429/50 |
| 4,947,124 A | 8/1990 | Hauser ...................... 324/430 |
| 4,952,861 A | 8/1990 | Horn .......................... 320/23 |
| 4,958,127 A | 9/1990 | Williams et al. ............ 324/426 |
| 4,968,942 A | 11/1990 | Palanisamy ................. 324/430 |
| 5,032,825 A | 7/1991 | Kuznicki .................... 340/636 |
| 5,040,126 A * | 8/1991 | Allington ..................... 702/47 |
| 5,047,971 A | 9/1991 | Horwitz ..................... 364/578 |
| 5,051,689 A * | 9/1991 | Hiwada et al. ............. 324/754 |
| 5,061,898 A | 10/1991 | Oram et al. ................ 324/427 |
| 5,107,191 A | 4/1992 | Lowndes et al. ............ 318/139 |
| 5,140,269 A | 8/1992 | Champlin ................... 324/433 |
| 5,166,623 A | 11/1992 | Ganio ....................... 324/427 |
| 5,179,340 A | 1/1993 | Rogers ...................... 324/428 |
| 5,191,291 A | 3/1993 | Taylor ....................... 324/429 |
| 5,214,385 A | 5/1993 | Gabriel et al. .............. 324/434 |
| 5,307,000 A | 4/1994 | Podrazhansky et al. ........ 320/14 |
| 5,315,253 A | 5/1994 | Alexandres et al. ........ 324/429 |
| 5,325,041 A | 6/1994 | Briggs ........................ 320/44 |
| 5,369,364 A | 11/1994 | Renirie et al. .............. 324/430 |
| 5,394,089 A | 2/1995 | Clegg ........................ 324/427 |
| 5,404,106 A | 4/1995 | Matsuda ..................... 324/431 |
| 5,432,452 A | 7/1995 | Fiorina et al. .............. 324/427 |
| 5,451,880 A | 9/1995 | Yamagishi et al. .......... 324/429 |
| 5,457,377 A | 10/1995 | Jonsson ........................ 320/5 |
| 5,572,136 A | 11/1996 | Champlin ................... 324/426 |
| 5,574,355 A | 11/1996 | McShane et al. ............. 320/39 |
| 5,619,417 A | 4/1997 | Kendall ..................... 364/483 |
| 5,757,192 A | 5/1998 | McShane et al. ........... 324/427 |
| 5,771,178 A * | 6/1998 | Stemporzewski et al. ..... 702/45 |
| 6,043,631 A | 3/2000 | Tsenter ...................... 320/148 |
| 6,411,098 B1 | 6/2002 | Laletin ...................... 324/436 |

* cited by examiner

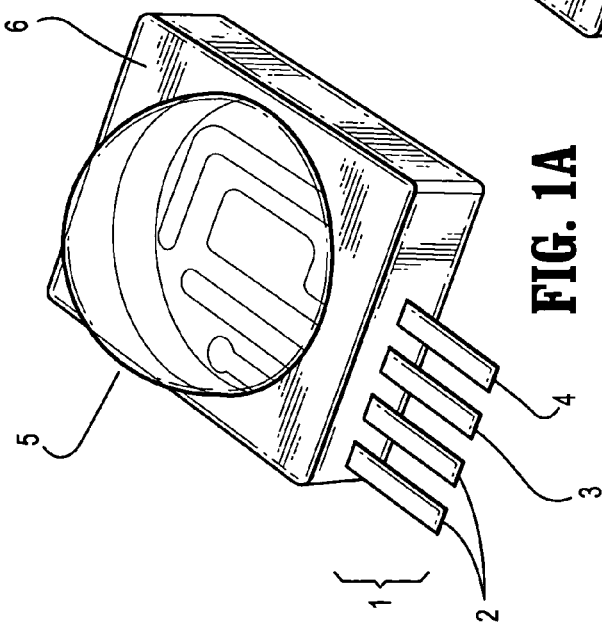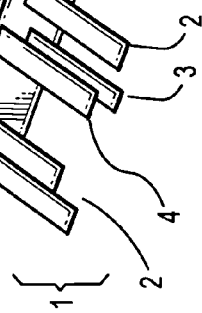

Excitation and Response Waveforms

Galvanodynamic Test System

Exponentially Decimated Data Point
First Discharge Pulse (32,768 Raw Data Points)

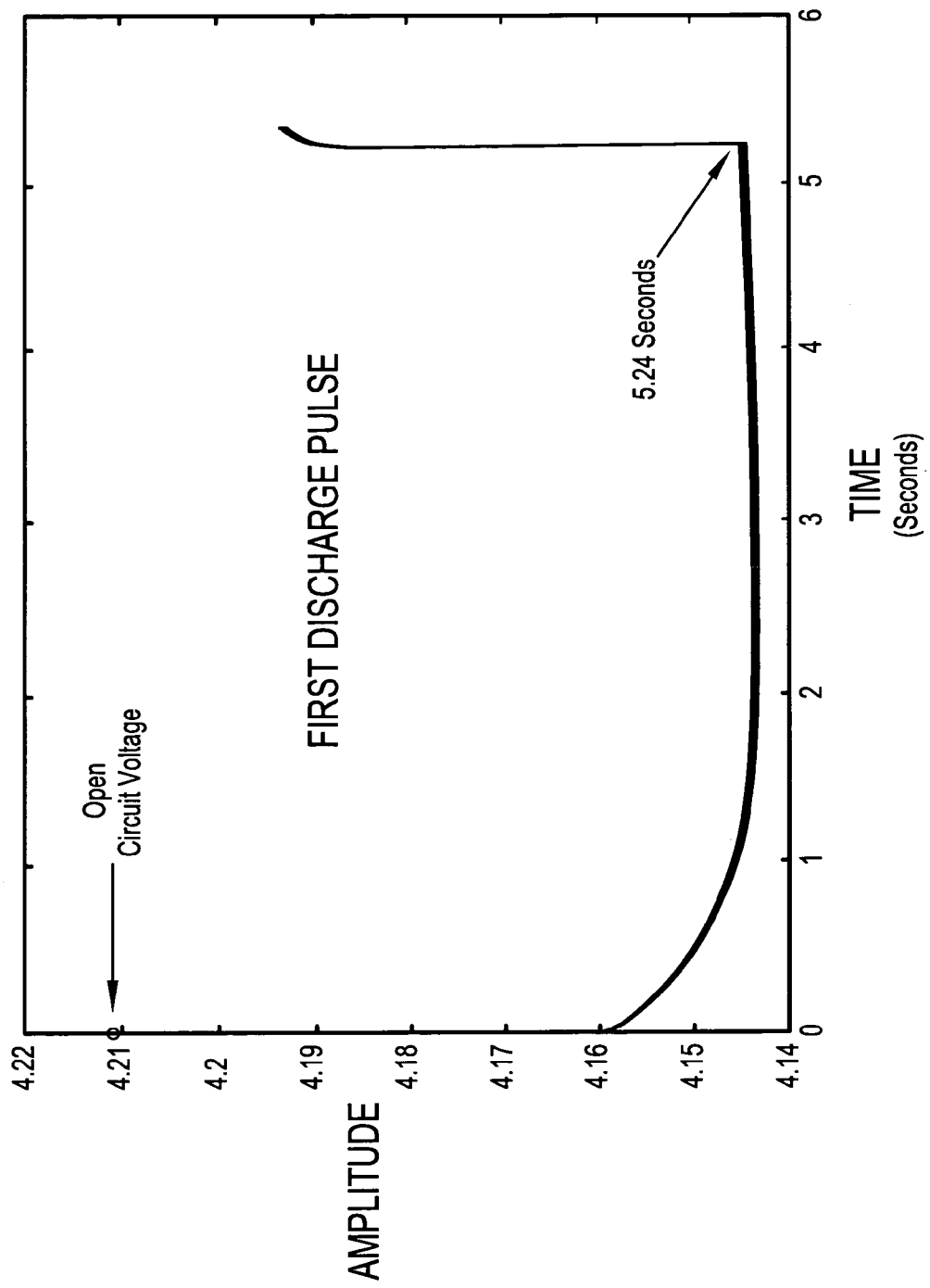

Increasing plot number indicates decreasing state of charge.

METHOD OF ANALYZING THE TIME-VARYING ELECTRICAL RESPONSE OF A STIMULATED TARGET SUBSTANCE

RELATED APPLICATION INFORMATION

This patent application is a continuation-in-part of U.S. Utility patent application Ser. No. 10/443,230, filed in the U.S. Patent and Trademark Office on May 21, 2003 and a continuation-in-part of U.S. Utility patent application Ser. No. 09/122,181, filed in the U.S. Patent and Trademark Office on Jul. 24, 1998 now abandoned which claims priority to U.S. Provisional Application No. 60/054,466, filed in the U.S. Patent and Trademark Office on Jul. 25, 1997 and is a continuation-in-part of PCT/US97/05002, filed in the U.S. Patent and Trademark Office on Mar. 27, 1997, which claims priority to U.S. Provisional Application No. 60/014,159, filed in the U.S. Patent and Trademark Office on Mar. 27, 1996, the entire contents of which are incorporated herein by reference.

FIELD OF THE INVENTION

The present disclosure relates generally to the electrochemical testing of systems containing biologic or non-biologic substances, and more particularly to an apparatus and method for detecting, measuring and analyzing the time-varying electrical response of a stimulated target device or substance.

BACKGROUND OF THE INVENTION

The invention relates both to the testing and evaluation of biological and non-biologic substances, electrical elements and electrochemical element, and combinations thereof, that are responsive to electrical excitation, as well as to the control of systems incorporating such substances and/or electrical and electrochemical elements, each of which exhibits the general characteristic of impedance, or conversely, admittance. A Device Under Test (D.U.T.), which may be, or may contain, any combination of substance or elements, is excited with a time-varying electrical signal while a synchronous sampling means is employed to acquire the response. A variety of analyses may be performed on the acquired data to determine at least one characteristic of the D.U.T.; in alternate embodiments, the inventive method may be used to assist or control systems within which said substances are either removably or permanently incorporated.

The determination of characteristics of electrically responsive elements and substances may be accomplished using both Frequency Domain and Time Domain techniques, commonly know as Frequency Response Analysis and Time Domain Spectroscopy respectively.

In the discussion that follows, the application of the inventive method both to simple non-biologic systems such as a non-rechargeable electrochemical accumulator (conventionally referred to as a "cell" or battery of cells), and to complex biologic systems, such as chemical samples derived from living organisms, will be described.

Lithium sulfur dioxide cells ($LiSO_2$) exhibit a 2.95V nominal operating voltage and provide high energy density and a relatively flat discharge profile over a wide temperature range. This combination of low weight per watt and excellent discharge characteristics make them the cell of choice for mission critical applications. The flat cell voltage profile, which makes such cells desirable, also presents difficulties in determining cell condition and state of charge.

Attempts have been made to use frequency response analysis, or electrochemical impedance spectroscopy techniques to evaluate these cells. However, the static impedance profile of this cell remains virtually flat across a wide range of test frequencies until nearly the end of their useful service life. In addition, to obtain a reasonable impedance/frequency profile using FRA techniques, sophisticated measuring equipment is used to provide multiple (sequential) tests at a plurality of frequencies, resulting in severely protracted test times.

Traditional chronopotentiometry/chronoamperometry (both conventional and cyclic) offer another method of measuring electrochemical cells. Here, the cell is provided with an excitation signal and the time varying response of the cell is determined. Traditional methods employ excitations (current or voltage) such as 'constant value' or 'pulse followed by relaxation interval'. One commercially available lithium battery tester employs such a 'pulse discharge/relaxation' method. It provides a relatively high current discharge event (60 seconds, at about a $C_{1-hr-rate/4}$), followed by a 'rest' period, wherein the battery is placed on open-circuit, and uses the profile of the battery's recovery voltage to diagnose the state of charge. With this device, when severely depleted batteries are tested, the high current levels employed can occasionally lead to 'venting' of $SO_2$ gas, with the attendant possibility of cell rupture. In addition, multiple, sequential tests of the same battery are strongly discouraged.

When evaluating the electrical response of a biologic target substance, multiple problems may arise as well. For example, currently a variety of well-known electrochemical techniques exist for performing assays of biological material. These techniques may be separated into three primary categories: 1) passive techniques or methods, 2) active techniques or methods and 3) a combination of passive and active techniques or methods; each of these is discussed in more detail below.

The application of a passive assay technique typically involves disposing one or more components within a test environment so that a chemical or electrochemical reaction occurs and gives rise to a detectable (measurable) current or voltage output.

The application of an active assay technique typically involves placing the substance of interest (henceforth, the "analyte") within a test chamber equipped with at least two electrodes. The analyte(s), which may be a single substance or some combination of different substances, is then excited, via the electrodes, with either a voltage or a current. The resultant conjugate response, which will take the form of a current or voltage respectively, may then be measured. In well-designed test paradigms, the nature or characteristics of the substance of interest (e.g., the "analyte") may be inferred from the functional and/or dynamical relationship that obtains between the excitation and the response signals.

These active techniques may be further separated into a plurality of sub-categories depending upon the nature of the excitation employed. If the assay technique employs a voltage which is applied across the excitation probes (i.e. 'across' the specimen disposed within the test chamber) as the independent variable and the voltage is constant, the active assay technique may be referred to as potentiostatic, whereas if the voltage is time-varying, the active assay technique may be referred to as potentiodynamic. As an example, U.S. Pat. No. 5,871,918 to Thorpe discloses a voltage-mode test method wherein cyclic voltammetry is employed to detect the presence of specific nucleic acids in a test sample. However, if the assay technique employs a current which is applied across the excitation probes (i.e. 'across' the specimen disposed within the test chamber) as the independent variable and the current is fixed or constant, the active assay technique may be referred to as galvanostatic, whereas if the current is time-varying, the active assay technique may be referred to as galvanodynamic.

Moreover, these methods may be employed in combination with each other. The application of a combination of the active and passive techniques typically employs an experimental paradigm, which may combine two or more of these techniques or methods in sequence. For example, a constant current may be forced through a test chamber until a specified differential voltage appears across the chemical sample, whereby the excitation control method abruptly changes to a 'constant voltage' mode, wherein the current is adjusted to maintain that specific voltage differential. The resultant time-varying current thereafter becomes the dependent (measured) variable. Additional alternations between voltage-mode and current-mode excitation control may also be incorporated into the experimental paradigm as well.

While current-mode excitation techniques have been used extensively in several areas related to biochemistry, these techniques are used primarily for the modification of biological systems rather than as the basis of analysis or measurement methods. As an example, U.S. Pat. No. 4,663, 006 refers to the remediation of blood chemistry imbalance regarding a method of electrochemical dialysis employing alternating current excitation and electro-mediated osteogenesis.

SUMMARY OF THE INVENTION

The invention provides a method and apparatus for measuring and analyzing the time-varying electric response produced in an electrical or electrochemical element or when excited by a time-varying electrical signal; when the excitation takes the form of a current signal, the attendant response is conventionally referred to as the time-dependent polarization voltage. The method can be generally used to evaluate the response of systems of interest that may include biologic and non-biologic substances exhibiting the property of electrical impedance (or conversely, admittance). The response is detected and converted into digital format by a sampling means, operating according to a sampling schedule that is synchronized with the excitation means; the excitation signal itself may also be sampled in a synchronous manner. The inventive method may be embodied in an open-loop form wherein the results of measurements and analysis are provided, or in a closed-loop form wherein said results are used to provide feedback, to modulate the behavior of a system or device.

It is an object of the present invention to provide methods of determining both the presence of an analyte by exciting it with a suitable time-varying electric signal, and then detecting, measuring and analyzing the concomitant electric response. The response of the analyte will depend on the presence or absence, the quantity or concentration, and/or some inherent properties of the target analyte.

According to another aspect of the invention, the response signal (viz., a voltage in the case of a current-mode excitation, or a current in the case of a voltage-mode excitation) may be analyzed to characterize various properties of the analyte(s). The raw data will correspond to the magnitude of the response signal as a function of time. The response data can be analyzed in various ways such as: 1) The calculation of the first and second time derivatives; 2) Extraction of the underlying sinusoidal components (i.e. the power spectrum) and optionally the phase of each component with respect to the phase of the excitation signal; 3) Evaluation of the distortion products found in the response under the condition that the excitation is a substantially pure sinusoid; 4) The determination of hysteresis effects under non-sinusoidal excitation conditions; 5) The determination of long-term DC biasing effect in response to non-linearities and or irreversible reactions occurring in the analyte.

Analysis that may be used will include, voltage vs. time For example, magnitude vs. time functions derived and its first or second time derivative. Various other signal processing techniques can be used to analyze the data such as extracting the real and imaginary components of a substantially sinusoidal response. A second may be extracting the power spectrum of a non-sinusoidal response. Or the distortion products found in the response under the condition that the excitation was a substantially pure sinusoid—A voltage response to a current mode excitation or a current response to a voltage-mode excitation.

Both immediate response signals, which may be either measured voltages or currents that arise due to the application of an excitation, various derived signals, and/or results of signal processing, such as for example, the rate of change over time of certain immediate response signals, may be used to characterize properties of the analyte(s).

By a further aspect of the invention, periodic or quasi-periodic excitation protocols, comprising a sequence of time-varying excitation patterns (where each pattern is termed an "excitation waveform cycle") may be employed, allowing the use of various synchronous sampling measurement techniques wherein a plurality of successive response measurements are accumulated for corresponding points in successive excitation cycles.

Moreover, a method for determining characteristics of an analyte is provided, the method including the steps of providing a time-varying current-mode electrical excitation to an electrochemical test device containing an analyte (SUT), which time varying signal comprises a periodic or quasi-periodic waveform; detecting by a detection means, the conjugate electrical response elicited from the analyte by the excitation; converting the detected response from an analog signal into a digital signal of an analog-to-digital conversion means, controlled by a synchronous sampling clock controlling means; and performing at least one predetermined analysis of the digital response signal to provide a characterization of the digital response signals.

In an alternative embodiment, a method of evaluating lithium sulfur dioxide ($LiSO_2$) cells is provided, the method comprising applying complex pulse type excitation signals characterized by alternating periods of discharging current and zero current to the cell; monitoring the voltage of the cell; extracting time varying cell polarization voltage information; and analyzing the time varying cell polarization voltage information to evaluate the cell.

The above discussed and other features and advantages of the present invention will be appreciated and understood by those skilled in the art from the following detailed description and drawings.

BRIEF DESCRIPTION OF THE DRAWINGS

The foregoing and other features and advantages of the present invention will be more fully understood from the following detailed description of illustrative embodiments, taken in conjunction with the accompanying drawing in which:

FIG. 1A shows a test chamber having two or more electrodes in a co-planar arrangement and containing the SUT;

FIG. 1B shows a test chamber having two or more electrodes in a non-co-planar arrangement and containing the SUT;

FIGS. 18A–18C shows raw data plots;

DETAILED DESCRIPTION OF THE INVENTION

The present disclosure provides a method for detecting, measuring and analyzing the time-varying electrical response of various systems and/or substances, such as an electrical system (i.e. $LiSO_2$ battery cell) or of a target substance(s)/analyte(s), as they are stimulated by a periodic, quasi-periodic, or more general time-varying electrical excitation. Each of these embodiments is discussed separately and in detail below.

Target Substance(s)/Analyte Evaluation

In a first embodiment, the target substances (hereinafter referred to as "analytes") are generally biological molecules that either exhibit detectable electrical responses to time-varying electrical excitation, or are complexes of such analytes with suitable marker molecules that serve to facilitate, enhance, or otherwise alter response(s) to excitation(s).

As schematically depicted in FIGS. 1A and 1B, the test apparatus comprises a test chamber 6 (sample holder) suitable for containing the Sample Under Test (SUT) 5 comprising an analyte or analyte/marker complex, which chamber is equipped with at least two or more electrodes 1, deployed such that an electrical excitation may be applied to SUT 5, and such that the electrical response of the excited sample may be detected and measured. Sense 2, collector 3 and emitter 4 electrodes (as described in more detail below) are arranged in the test apparatus such that sensitivity is optimized. Although, the electrodes may preferably be disposed in a co-planar arrangement, as shown in FIG. 1A, it is contemplated that non-co-planar arrangements, as shown in FIG. 1B, may also be used without deviating from the scope of the invention. The electrical excitation may be either a voltage-mode or a current-mode signal, and the resultant response will accordingly be in the 'conjugate' domain, that is, appear either as a current or a voltage, respectively. Thus, if the excitation is provided as a current signal, the response will arise as a voltage and vice versa.

Figure 2:
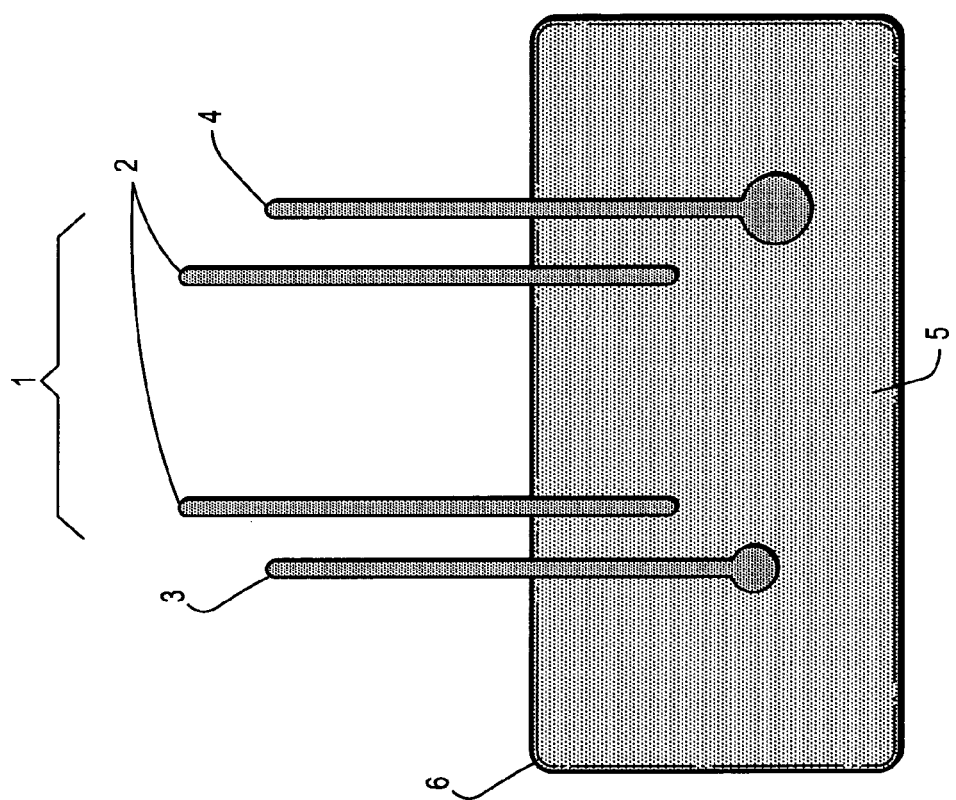
FIG. 2 shows a test chamber having a collector electrode and an emitter electrode.
Figure 3:
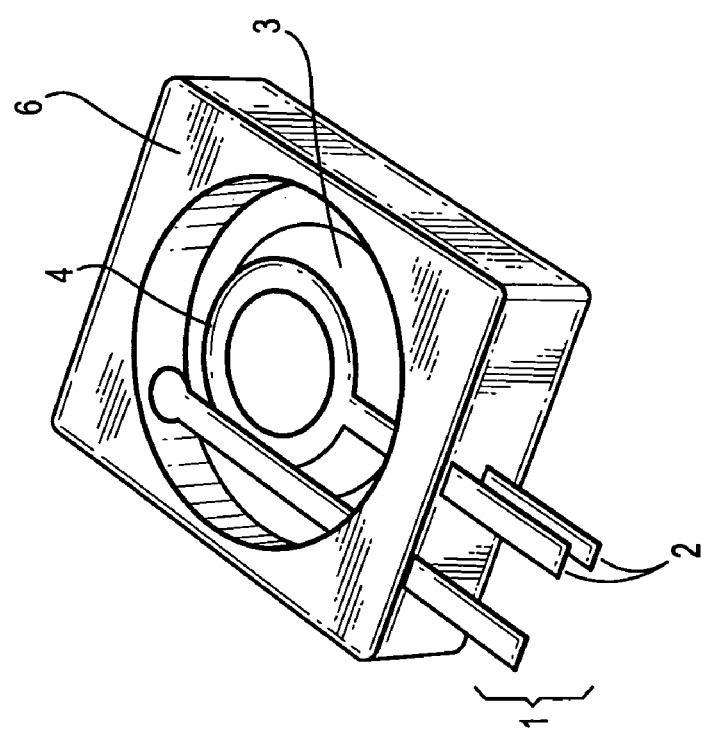
FIG. 3 shows a test chamber having multiple electrodes.
Figure 4:
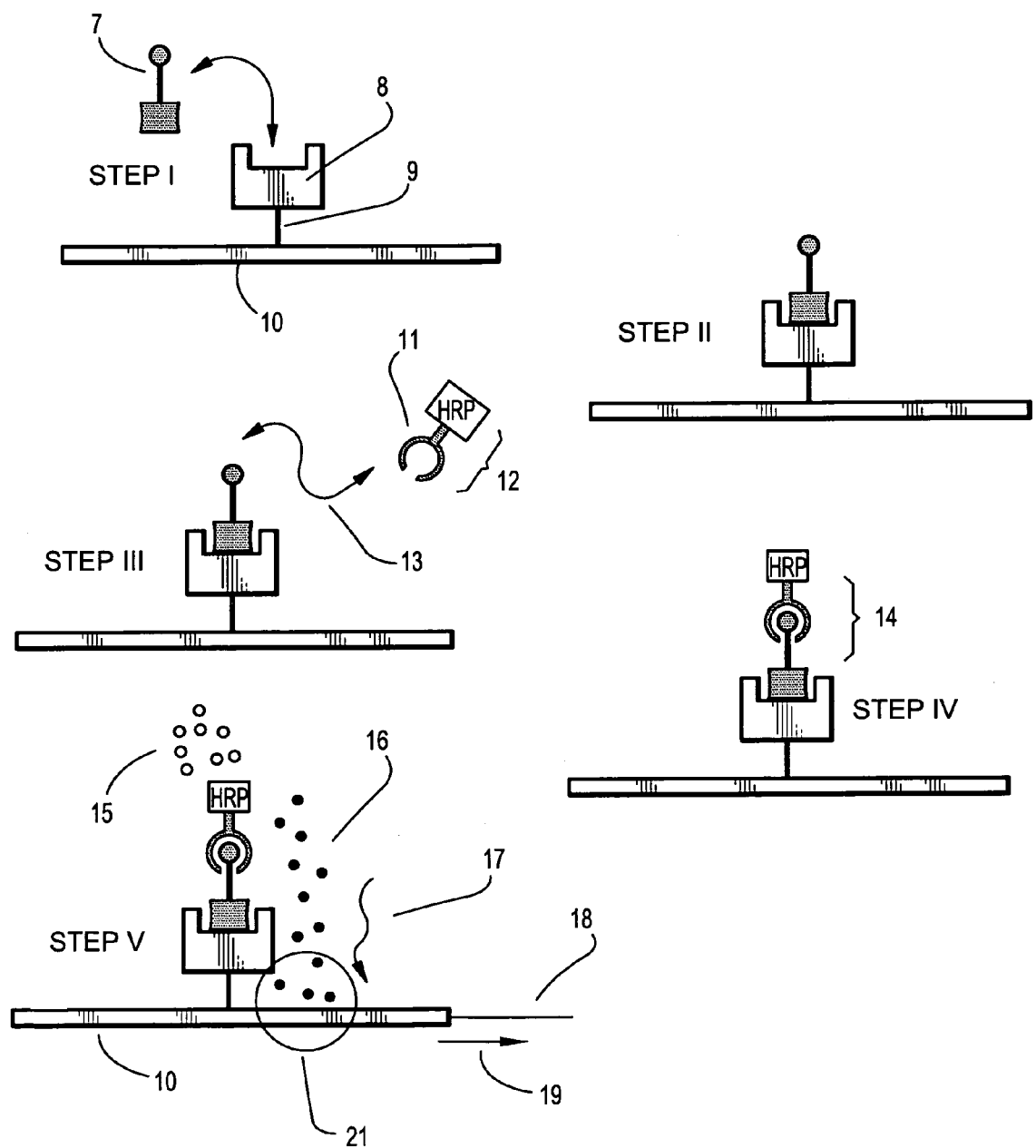
FIG. 4 shows a typical potentiostatic-based biosensor used in immunoassays.

According to the existing well known techniques, the SUT 5 is prepared within the test 6 chamber to appear as or within a distinct layer formed substantially parallel to one electrically conductive surface, known as the collector electrode, as shown in FIGS. 2, 3 and 4. The chamber 6 contains at least one additional electrically conductive electrode or set of electrodes 1, which in these figures are referred to as the emitter 4 and collector 3 electrodes. The collector 3 and emitter electrodes 4 are connected to an external excitation drive device, which may selectably function either as a controlled voltage source or as a controlled current source. It is contemplated that in an alternate embodiment, a plurality of emitter and collector electrodes may be employed, wherein all of the emitter electrodes are effectively coupled in parallel with respect to the drive device, and similarly, all of the collector electrodes are connected in parallel with respect to the drive device. It is also contemplated that additional reference and sense electrodes may be employed whereby the reference electrode has a stable electrochemical potential (constant) and is used to accurately measure the electrode potential of the collector electrode.

A conformal medium such as a fluid electrolyte (or a similar charge-carrying substance) is added to the test chamber such that it comes into intimate contact with both the sample to be tested, and with every electrode within the chamber. The conformal medium has a composition, which permits the flow of electrical current from the emitter electrode(s) through the SUT to the collector electrode(s), whenever a suitable potential is impressed between the emitter and collector electrodes by the external drive device.

The geometry of the test chamber and the positions of the electrodes are preferably arranged so that substantially all of the excitation current will pass through (rather than 'around') the SUT. This ensures that there will be minimal leakage current flow from the emitter electrode(s) to the collector electrode(s) along pathways that bypass the SUT. This is desired because any such leakage current would tend to reduce the sensitivity and accuracy of the measurement. Depending on the specific application, either or both the emitter and collector 'electrode' may actually consist of more than one physically discrete electrode elements as mentioned above. FIG. 3 shows one example of a test chamber 6 having a suitable emitter 4, collector 3 and additional electrodes 1, 2. Similar to FIG. 1B, this example depicts a non-co-planar electrode configuration.

When a sufficient electric potential is applied between the emitter and collector electrodes, current will flow from one to the other, thus passing through the SUT. Electric or electrochemical reactions (e.g., ionization reactions, reduction/oxidation reactions, decomposition reactions, electrical polarization effects and the like) occurring within the sample will tend to affect the voltage response arising in response to the passage of current, and hence impart a distinctive signature to the detected response. The electrical response may be detected (sensed/measured) by a suitable electronic detector/sensor, typically a high impedance differential input preamplifier (or an array of such preamplifiers), that may be connected to the excitation electrodes, or alternately, that may be connected to some combination of the excitation electrodes (e.g., the collector and emitter electrodes) and/or one or more separate detection/sensing electrodes. In the case wherein the detector/sensor is not connected to either excitation electrode and at least two separate detector/sensor electrodes are employed, the configuration is conventionally known as a Kelvin connection.

In FIG. 2, separate electrodes are provided for the drive and sense functions, so that a Kelvin configuration can be achieved by connecting the drive device to electrodes 3 and 4, while the sense preamplifier device is connected to sense electrodes 2. As is known in the art, a Kelvin connection is often preferred over other arrangements to provide a more accurate determination of the electrical response. The SUT 5 is tested using this configuration.

Various sample preparation methods are commonly employed when performing biological identification/detection as outlined in this embodiment. Several of these preparation methods and their resultant sample structures are described below in examples 1–4.

EXAMPLE 1

Enzyme Detection—General

Enzymes are found within biological systems, where they serve to enable, facilitate or otherwise improve the efficiency of important chemical reactions. Enzymes serve as catalysts for chemical reactions; where they dramatically increase the rate and/or efficiency of the reaction, while in other cases the presence of the enzyme is essential for the reaction to occur at all. For example, an enzyme may cause one of the reactants (note: reactants are conventionally referred to as "substrates") to assume a particular proper physical shape (confirmation) whereupon it can then (and only then) undergo the desired reaction. Another characteristic of certain enzymes is that they have specific affinities for certain target molecules: when the enzyme encounters its specific target molecule, it immediately binds to it (the subsequent disassociation of the enzyme from the target may often be achieved by a separate reaction); this behavior is useful when it is desired to attach an identifiable 'marker' to a target molecule.

When investigating enzyme mediated biological reactions, it is often useful to be able to detect either the presence and/or the concentrations of specific chemicals (and/or enzymes) in a sample; this sort of qualitative or quantitative determination is conventionally performed using a biological assay (i.e. test protocol).

Conventional assays often include direct measurement of the concentration of the products and reactants (substrates). In reaction (3), measuring the concentration of glucose would constitute an assay. In reaction (3), b-galactosidase acts as the catalysis. Another more common method of following reaction (3) would be to use a substrate such as 4-chloro-3-bromo indole or o-nitro-phenol that produces a colored reaction product.

lactose→glucose+galactose (3)

By following the color change, using either the naked eye or optical spectroscopy, enzymatic reactions can be closely monitored. In this example, no electrochemical technique is applied. When optical methods are employed, the assay is often handicapped in that the calculated concentrations of both the products and reactants are limited by the optical detectability (for example—the absorbance) of the reaction product(s).

If very low concentrations (picomolar) of reaction product are to be optically detected it is often necessary to have very clear (ultra-pure) analyte solutions. This requires a filtration step which is time consuming and costly. Consequently, immunoassays that employ electrochemical detection instead of optical methods have received considerable attention.

EXAMPLE 2

Immunoassays—Overview

The key components of any immunoassay are the following: 1) an antigen to be tested, 2) the antisera (serum containing antibodies) to this antigen, and 3) some system for detection. The detection system may be integrated into the test protocol.

Three of the most basic immunoassays include: 1) Competitive Immunoassays, 2) Immunosorbant Assays, and 3) Immunometric Assays. In these assays it is most often the cast that the antibody binds the antigen, which is labeled with some detection system.

Optical detection systems are commonly employed where monoclonal antibodies, proteins, etc., are attached to a fluorescent dye molecule such as Fluorescein isothiocyanate (FITC), Peridinin chlorophyll protein (PerCP), Allophycocyanin (APC) and others and detected optically.

In some immunoassays, Horse Radish Peroxidase (HRP) or Alkaline Phosphate (AP) is used for the detection system. Enzymes such as these are typically selected because they exhibit good stability and have a high turnover number (a catalytic constant that is a measure of the catalytic efficiency—specifically the number of reaction processes catalyzed per enzyme site per unit time). In this regard, the enzyme effectively acts as both an amplifier and detection beacon. Detection is accomplished when substrate is added and the enzyme produces some secondary product that can be optically detected either directly or after reaction another substance.

One example of a potentiostatic-based biosensor used in immunoassays is as follows: An enzyme is used that catalytically converts non-active analyte into some secondary product that can be oxidized or reduced at an electrode surface. If the electrode is biased at a specific potential with respect to another electrode, current is produced due to the oxidation or reduction of the secondary product. The anodic (negative) or cathodic (positive) current is proportional to the concentration of the secondary produce, which is in turn proportional to the original analyte concentration. Enzymes such as Horse Radish Peroxidase (HRP) and Alkaline Phosphatase (PA) are typically used in this type of biosensor.

There are commonly a number of steps involved in transforming the secondary product into the actual detectable species. For purposes of simplification, these intermediate steps have been omitted from this discussion. FIG. 4 is an illustration of one such enzyme detection system assay with its respective sample structure. In this example, STEP I—a protein or some other biomolecule to be detected 8 is attached 9 to a sensor surface 10, after which another biomolecule 7 (i.e. protein) specific antibody is loaded onto the attached biomolecule (protein). In STEP II, the antigen 11 is attached (usually prior to the bio-assay) to an enzyme (HRP in this case) to form and antigen/enzyme-attached pair 12. In STEP III, Attachment 13 of the conjugate to the biomolecule specific antibody 7 is performed after which the completed structure 14 (STEP IV) is ready for electrochemical detection. In STEP V, non-active analyte (primary product) 15 is introduced into the system, which is consumed by the enzyme (HRP) producing detectable material 16 (secondary product). Secondary product migrates 17 to the sensor surface where a charge transfer reaction 21 occurs. The charge transfer reaction causes current 19 to flow in the external circuit 18 and is detected by the external test apparatus outlined in FIG. 10.

EXAMPLE 3

Electrochemical Sensor Characterization

Most electrochemical-based biosensors undergo some form of pretest characterization to ensure that the sensor is functioning properly. An analogy in the electronics industry is, prior to final packaging of printed circuit boards (PCB); diagnostic testing is performed to ensure proper operation. Often times an electrical test fixture is developed that rapidly tests all of the operation of the PCB.

With an electrochemical biosensor, each step leading up to final detection (washing, mixing, hybridization, incubation, etc.) can be monitored using the present apparatus. Most often, these monitoring steps must be noninvasive, in that they should not perturb the system under test.

Figure 5:
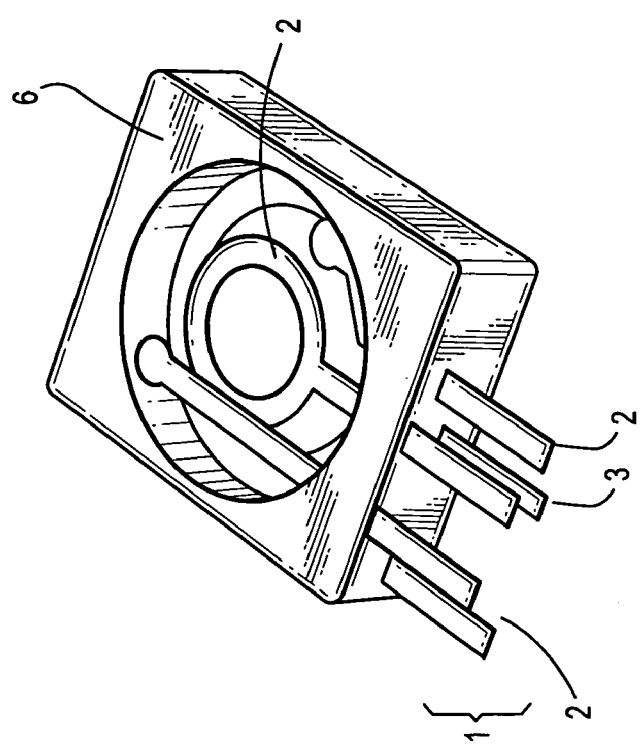
FIG. 5 shows a biosensor having multiple electrodes.

The invention may also be used to drive a reaction prior to detection. This would be an invasive technique. For example, cell lysing or denaturation can be accomplished using the invention. Additionally, calibration of the sensor prior to commencing an assay can be rapidly performed. FIG. 5 is an illustration of a biosensor fabricated with sample holder 6, where any number of electrodes 1, 2, 3 may be used to perform the biological protocol and subsequent detection/sensing. Microelectrodes (micro-biosensors), similar to those shown in FIG. 5, are commonly used in electrochemical detection because of their minimal potential drop in comparison to macroelectrodes. Consequently, low conductivity solvent, non-polar solvents and a host of other mediums can be uses with microelectrode-fabricated biosensors.

EXAMPLE 4

Other Biological Specimen Characterization

Figure 6:
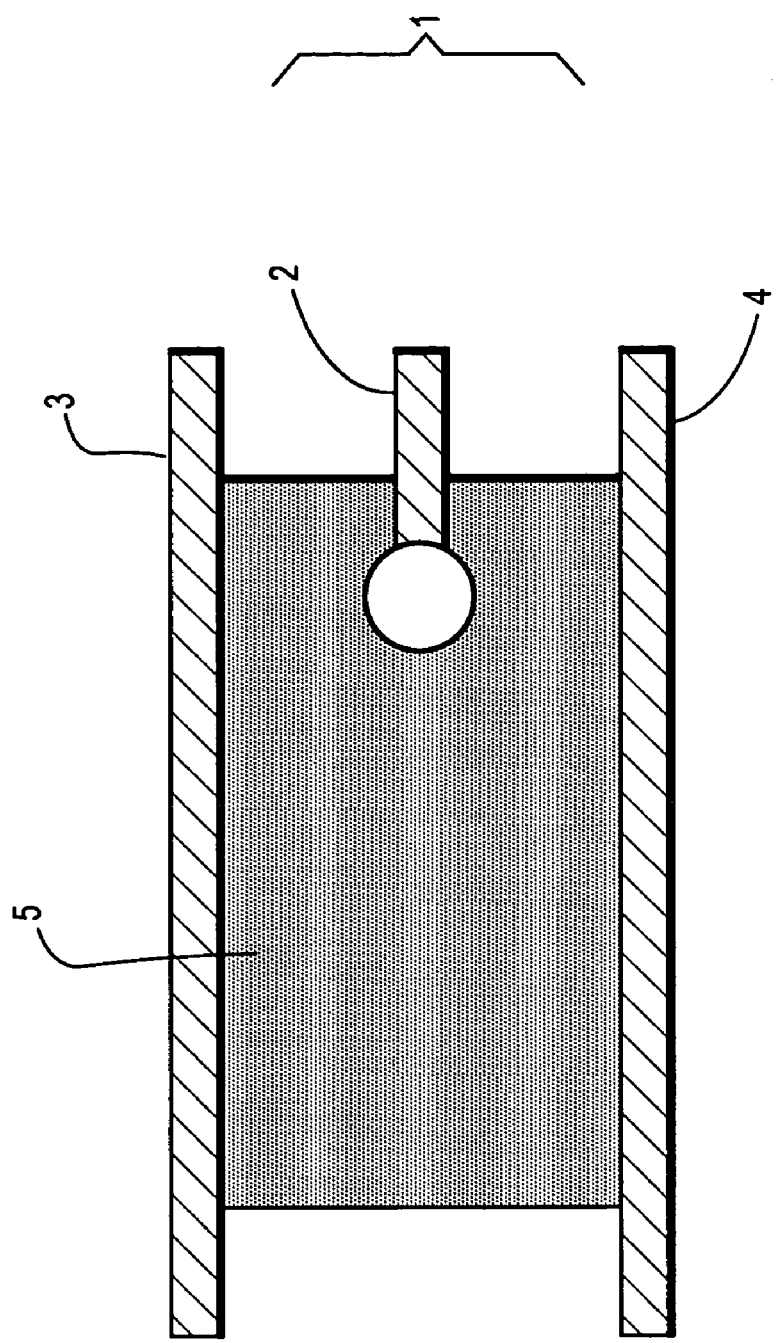
FIG. 6 shows a general specimen.
Figure 7:
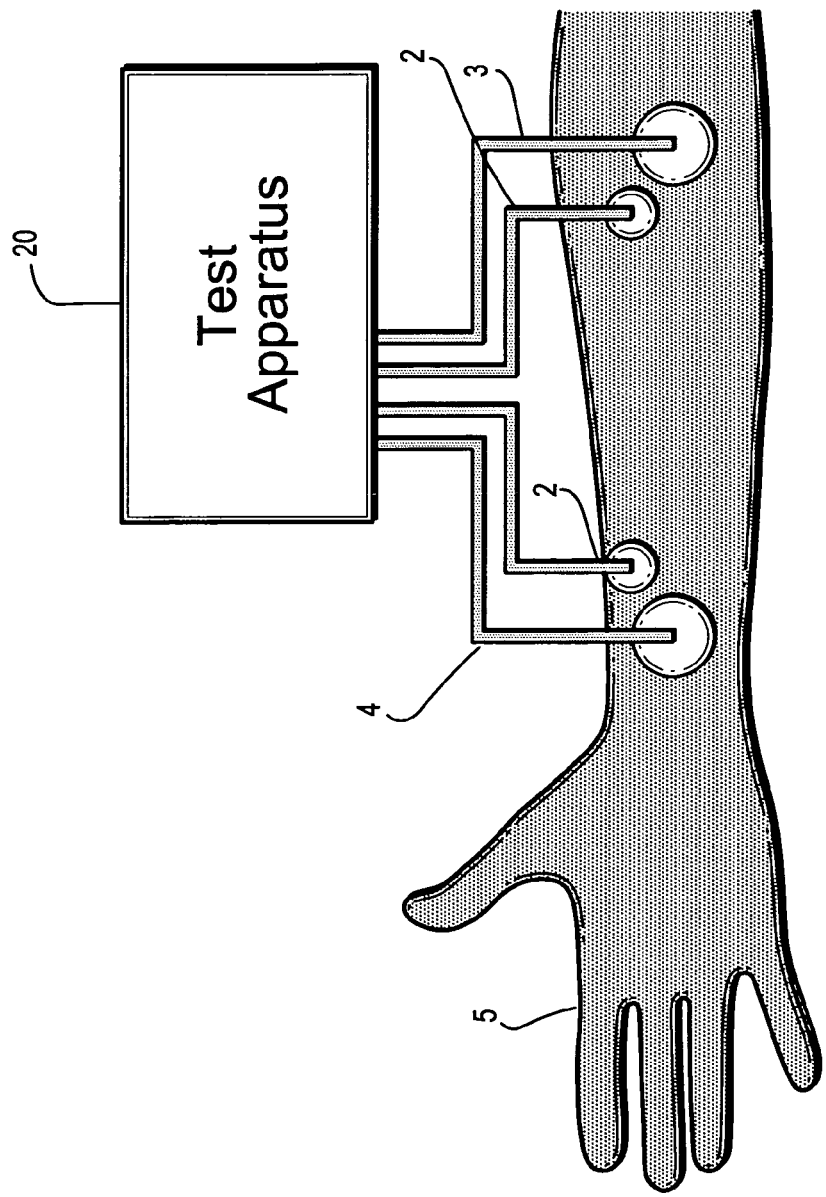
FIG. 7 shows a human body part specimen.

The present invention (apparatus) may be employed as a detection technique for a wide variety of biological systems. These systems (specimens) include blood specimens (metabolites and electrolytes—Potassium, Sodium, Chloride, pH and $pCO_2$, Glucose, Creatinine, $pO_2$, Hermatocrit, Bicarbonate, Hemoglobin, Lactate, Ionized Calcium, and other serum electrolytes, metabolites, and blood gases) and other, tissue specimens, various human and animal body parts (FIG. 7) as well as a host of other samples. In FIG. 7, a human arm 5, is stimulated using an emitter 4 and collector 3 electrodes with their respective sense 2 electrodes. The test electrodes are connected to the test apparatus 20. FIG. 6 illustrates a very general test system, where the SUT 5 is stimulated by emitter 4 and collector 3 electrodes with only one sense (reference) 2 electrode.

EXAMPLE 5

DNA/RNA Detection

Figure 8:
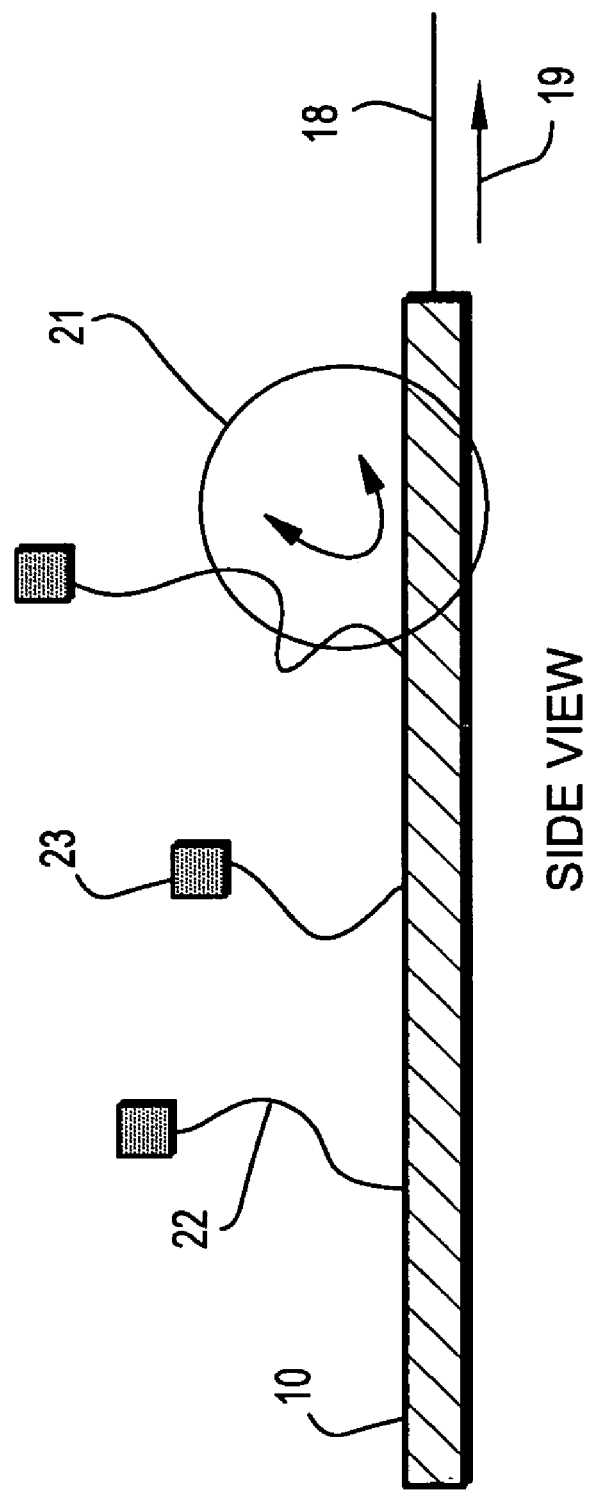
FIG. 8 shows a basic electrochemical DNA/RNA detection scheme.

Similar to EXAMPLES 1 and 2, DNA and RNA can be detected using both optical and electrochemical techniques. In the case of optical detection, typically a fluorescent dye molecule is attached to DNA or RNA that has been anchored to a sensor surface and detected using an optical sensor (Photo-multiplier tube—PMT). With electrochemical detection, an enzyme is typically attached to the anchored DNA or RNA sample and detected using a conventional electrochemical detection scheme. FIG. 8 illustrates a very basic electrochemical DNA/RNA detection scheme where a sensor surface 10 is cover with some biological specimen (e.g. DNA/RNA strands) 22. Similar to EXAMPLE 2 (FIG. 4), secondary product, produced by the signaling enzyme 23, is detected at the electrode surface in a charge transfer reaction 21. Current 19 is detected in an external circuit 18. Additionally, electronic conduction (transport of electrons and holes) through the DNA base pairs is another way in which charge may be passed.

Figure 9:
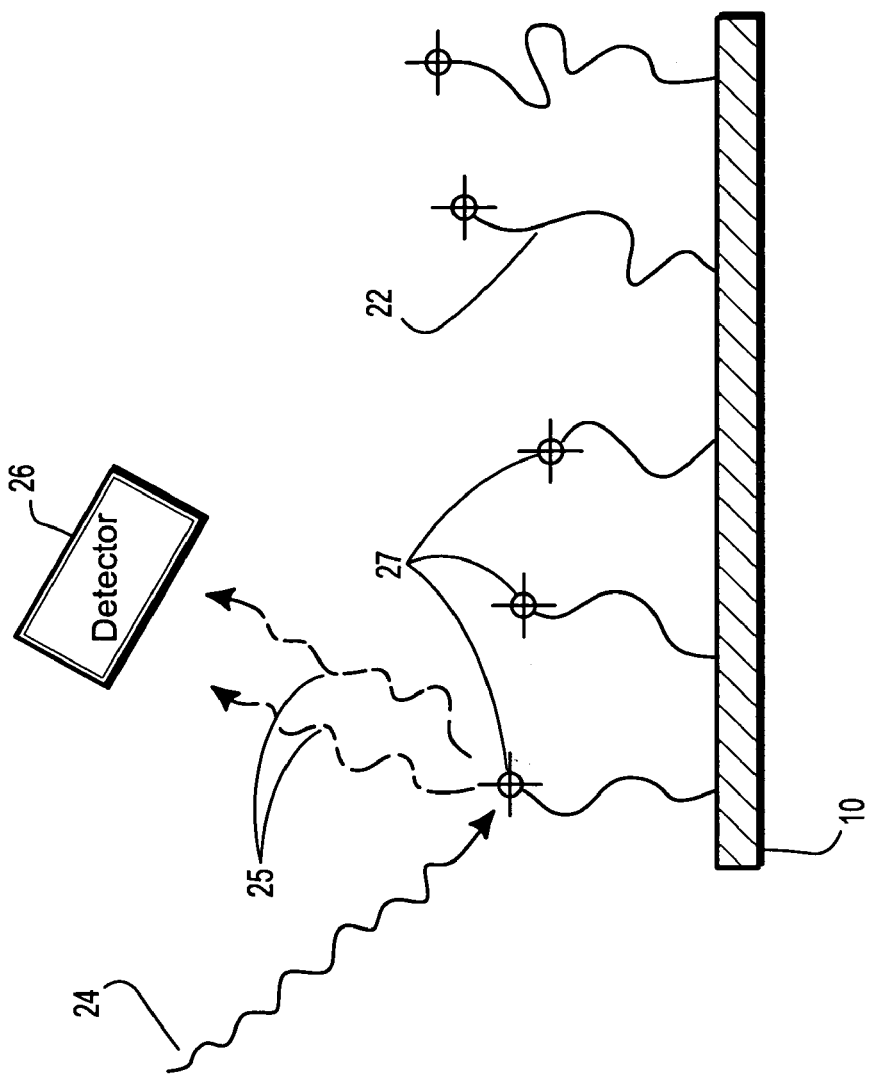
FIG. 9 shows the components of a typical optical measurement scheme.

Both qualitative and quantitative information can be realized from the amount of current measured (flowing) resulting form the electrochemical reaction. FIG. 9 illustrates the components of a typical optical measurements scheme. Once again, biological specimen 22 is attached to a sensor surface 10. Optical dye molecules 27 are attached to the biological specimens after which, an excitation signal 24 (light) is used to stimulate the optical dye molecule. The emission from the optical dye molecule is detected using a detector 26 (typically a PMT).

Discussion of Excitation Protocols

The various preferred excitation signals may be usefully distinguished according to several key characteristics. By convention, a single excitation "cycle" may be described as a time varying signal that exists for a fixed (and finite) duration, and exhibits at least two or more distinct amplitudes during the cycle; the signal may be characterized either as a voltage or a current. Whenever a signal exhibits more than one amplitude value, it is know as an "AC" signal. Excitation signals may be generated by conventional analog circuitry means, such as fixed or adjustable oscillators, or by digital means that embody digital-to-analog converters whose output voltage amplitude may be changed in discrete steps under external control such as may be provided by a microcontroller or other logic device. In the preferred embodiment, a reference clock may be provided as well, to serve as a phase reference (with respect to the excitation), so that various types of data acquisition and analysis techniques may be properly applied.

A single cycle of an AC signal may either be unipolar or bipolar. Within a unipolar signal, all of the amplitude values have the same relative polarity, with respect to a common reference point, called the "ground" reference point, or simply "ground," with the understanding that the set of amplitudes of unipolar signals of either polarity includes zero with respect to ground (that is, may appear at the common potential). Thus, a signal that alternates, say, between some positive (or negative) value and common value (where amplitude is exactly "zero") is also to be considered a unipolar signal.

In contrast, the polarity of a bipolar signal will undergo one and only one change of polarity within each whole cycle; in this case, a single signal cycle must exhibit one portion that is positive (that is, above ground) and another distinct portion that is negative (that is, below ground).

Figure 10:
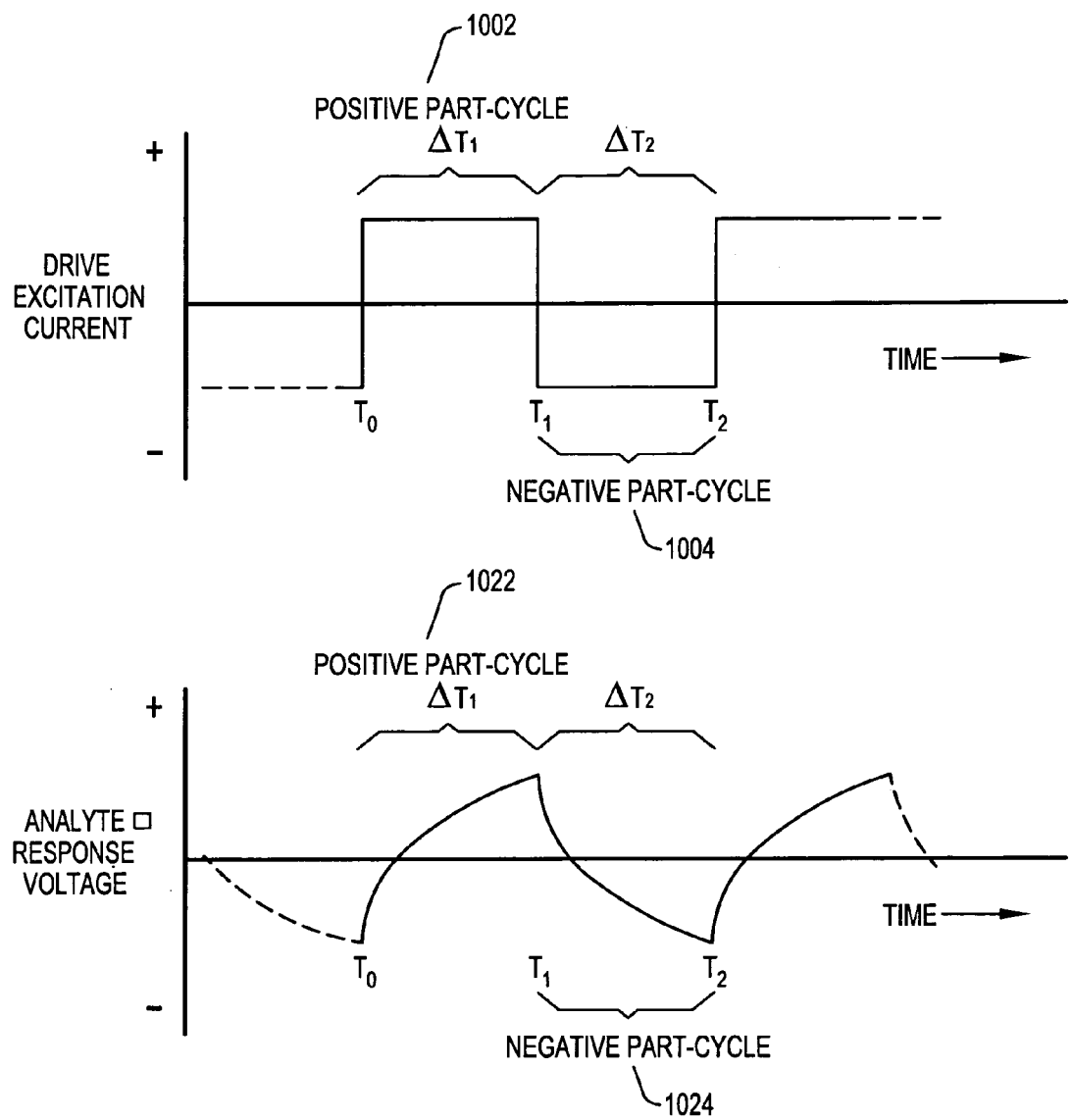
FIG. 10 shows a block diagram of an apparatus.

By convention throughout this specification, a single AC cycle, irrespective of its particular shape, will be understood to comprise two parts, and is depicted schematically in FIG. 10; these parts will be referred to as "part cycles". A typical single cycle of the excitation waveform (indicated as a current-mode signal in the example) comprises positive part-cycle 1002 and negative part-cycle 1004; correspondingly the response waveform (indicated as a voltage-mode signal in the example) comprises positive part-cycle 1012 and negative part-cycle 1014. A special case obtains when the first part of a cycle has the same duration as the second part, such that the cycle exhibits a 50% duty cycle (that is, the mark/space ratio is exactly one). The juncture at which part-cycles meet, corresponds to the boundary point between said part-cycle portions, and as such serves both to define the end of the leading waveform portion, and the beginning of the trailing waveform portion.

Common examples of a single cycle excitation signals include a sine wave, a square wave, a triangle wave, and a unipolar step (wherein the signal amplitude executes an abrupt transition between two otherwise constant amplitude values). When a plurality of identical cycles is seamlessly joined together in time, the result is referred to as a periodic signal; if several periodic (but dissimilar) signal segments are added together, the resulting sum is a quasi-periodic signal. Other useful types of excitation may include a rectilinear waveform, exhibiting a leading edge that constitutes an abrupt amplitude transition, followed by a substantially constant-amplitude portion, followed by another abrupt amplitude transition representing a trailing edge; or a ramping waveform comprising, in either order, an abrupt amplitude step representing an abrupt amplitude and a portion whose amplitude varies with time in a linear fashion (an so may be characterized as a ramp), thus exhibiting a constant, but non-zero, first derivative with respect to time.

AC (that is, time varying) excitation signals may either exhibit a time-averaged value of zero (over any integer number of whole cycles), or may have a net bias, wherein the average value is not zero for some or all of the duration of the excitation (which itself is understood to comprise one or more whole cycles). When a net bias is present, it should be understood that the Device Under Test will thereby by subjected to an overall charging or discharging event, for a positive or negative net bias, respectively. Note that any AC signal that exhibits a net bias may be decomposed into two or more independent components, one of which may be (but not necessarily) a DC component.

In order to clearly apprehend the method, a specific example will be presented in detail; however, it should be understood that this example should not be construed to limit the scope of the invention, which scope is only limited by the appended Claims.

Response Measurement and Data Sampling Method

Figure 11:
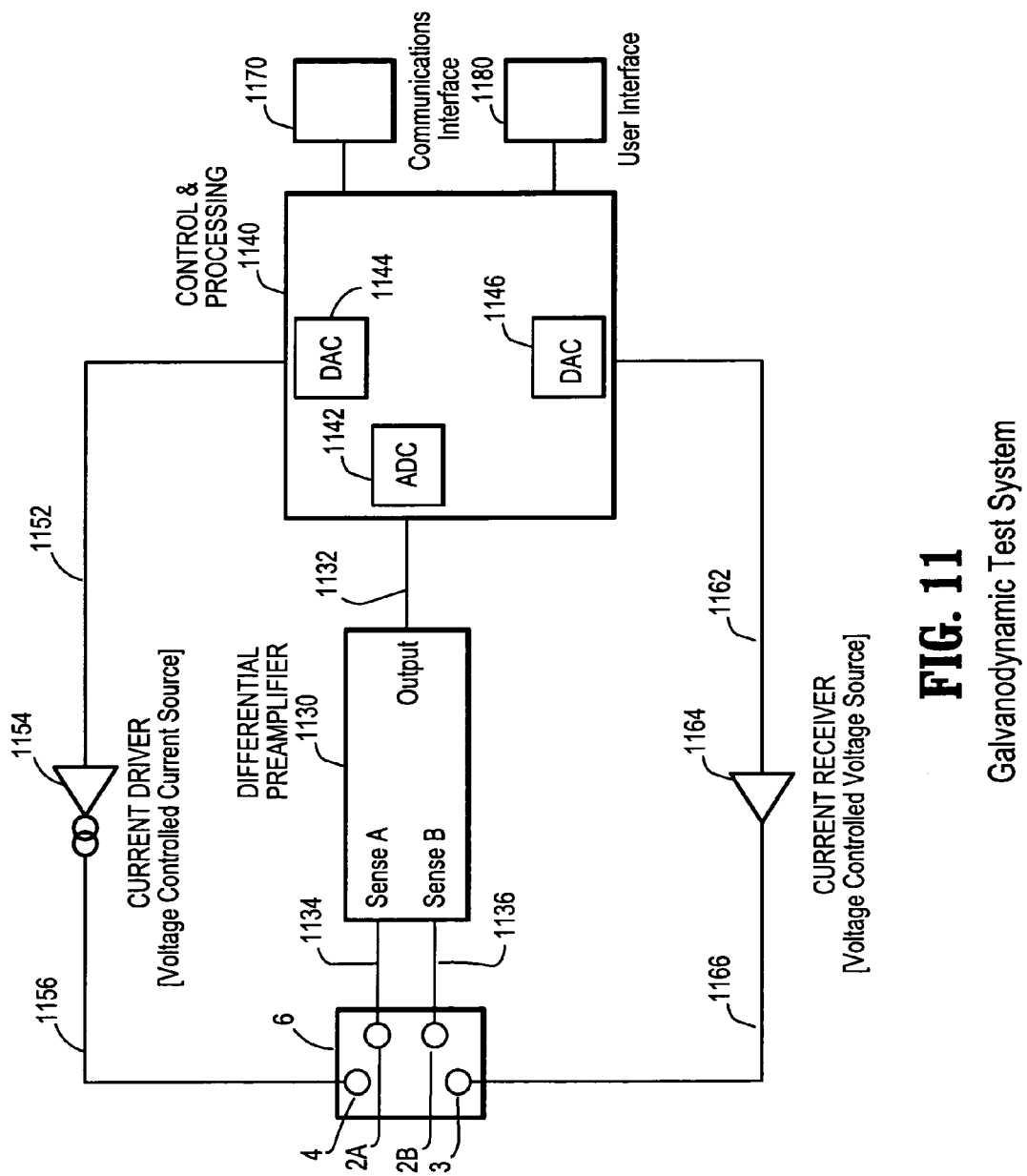
FIG. 11 shows a galvodynamic test system.

A schematic representation of a test unit suitable for performing electrochemical tests on samples of interest is provided in FIG. 11. The system comprises Control/Processing Unit 1140, Communications Interface 1170, User Interface 1180, an excitation delivery sub-system employing Current Drive 1154 and Current Receiver 1164, and a response-sensing Differential Preamplifier 1130. Test Chamber 6, suitable for containing a Sample Under Test and containing a plurality of electrodes, is connected to both the excitation sub-system and the preamplifier. In operation, a current-mode AC (e.g., galvanodynamic) excitation is applied across a Sample Under Test, which is located within the test chamber, and the resulting time-varying voltage response is detected and analyzed to determine specific characteristics of the sample. In alternate embodiments, the circuitry may be re-configured such that a voltage-mode excitation may be employed while the time-varying current response may be measured.

Communications Interface 1170 serves as a means whereby control information may be input to the Test System and response data may be output, while User Interface 1180 serves both as a means for the user to input test and control parameters and as a means for providing a visual display of process parameters and other information.

A current-mode excitation signal, created by Digital to Analog Converter (DAC) 1144 under the control of controller 1140, is applied to chamber through emitter electrode 4 and is returned to collector electrode 3 which is conventionally maintained at a fixed potential, nominally ground, by DAC 1146); these electrodes are suitably disposed to cause the current to flow substantially through the Sample Under Test located within the chamber. The electrical response invoked by the excitation current signal appears as a time-varying response voltage between pairs of sense electrodes 2A and 2B located within test chamber 6. As described previously, these sense electrodes are preferably positioned within the test chamber so that the voltage that appears between them reflects the voltage that is developed across the Sample Under Test during the test event.

The response voltage is conveyed via connections 1134 and 1136 to the inputs of a high impedance differential preamplifier 1130. The output of the differential preamplifier is conveyed via connection 1132 to Control and Processing Unit 1140, wherein, in known fashion, the analog signal is converted to a digital representation by means of Analog to Digital Converter 1142, and is subsequently routed to other elements (not shown) within the Control & Processing Unit for analysis.

The Analog to Digital converter (ADC) is used to sample or transform the time-varying analog voltage into the digital domain for subsequent storage and numerical analysis. As is known in the art, an ADC may be placed under the control of a sampling clock signal, whereby the ADC is commanded to take a single brief sample of the voltage presented at its analog input port during a particular point in each clock cycle (typically, at a rising or falling edge), and then immediately convert the analog voltage into a corresponding digital representation. By varying the temporal schedule of the sampling clock, the relative 'position in time' of consecutive samples may be adjusted as desired. This ability to manipulate the precise sampling schedule of an ADC allows a virtually infinite number of sampling protocols to be used as needed.

In the preferred embodiment synchronous sampling techniques may be employed. A variety of synchronous sampling methods have been developed by one of the authors and disclosed in U.S. Pat. No. 6,411,098 and in pending application # 09/122,181 (Evaluation of Lithium Sulfur Dioxide Cells), which are herein incorporated by reference in their entirety. More specifically, when the excitation consists of a periodic signal comprising a plurality of AC waveform whole cycles, the sampling schedule may be defined such that the number and relative temporal position (relative to the first part of each part-cycle) of the successive data samples taken of the response voltage within each part-cycle is identical for each part-cycle of the same relative polarity and duration. Typical sampling schedules include: constant $\Delta\tau$—sampling, wherein every interval between successive samples within a half-cycle remains constant; logarithmic sampling, wherein the interval between successive samples within a part-cycle increases in an exponential fashion; and "a priori scheduled sampling", wherein the temporal offset of each successive sample with respect to the onset of the present part-cycle is predetermined according to a previously established list of values, which list of values may or may not be derived from a simple mathematical function. The sampling schedule may also be determined during testing, as a function of, or algorithm applied to measured variables, or variables derived from measured variables. For example, the sampling rate may be made to depend on the rate of change of a measured response voltage (or current), so that a relatively large number of samples are taken when the response voltage (or current) is rapidly changing. In this case the sample times are recorded. In all cases, the sample timing information or data is considered an integral part of any time-series data. Clearly, these methods may be generalized to allow for the synchronous sampling of waveforms that exhibit duty cycles of other than 50%; in such case, it may be desirable to provide substantially different sampling schedules for each part cycle of the waveform.

By manipulating the sampling schedule, any desired degree of temporal resolution may be obtained (subject, of course, to the intrinsic performance limitations of the particular ADC employed). Once the sampled data is available in digital form, a variety of analysis techniques may be immediately applied.

For example, when a linear sampling schedule (that is, constant $\Delta\tau$) is specified, the resulting time domain data may be analyzed using conventional linear methods as well as the familiar Fourier and Laplace integral transforms (whereby time domain data may be transformed into the frequency domain). When non-linear sampling schedules are used, the analysis methods must be designed specifically or appropriately for each case.

Figure 12:
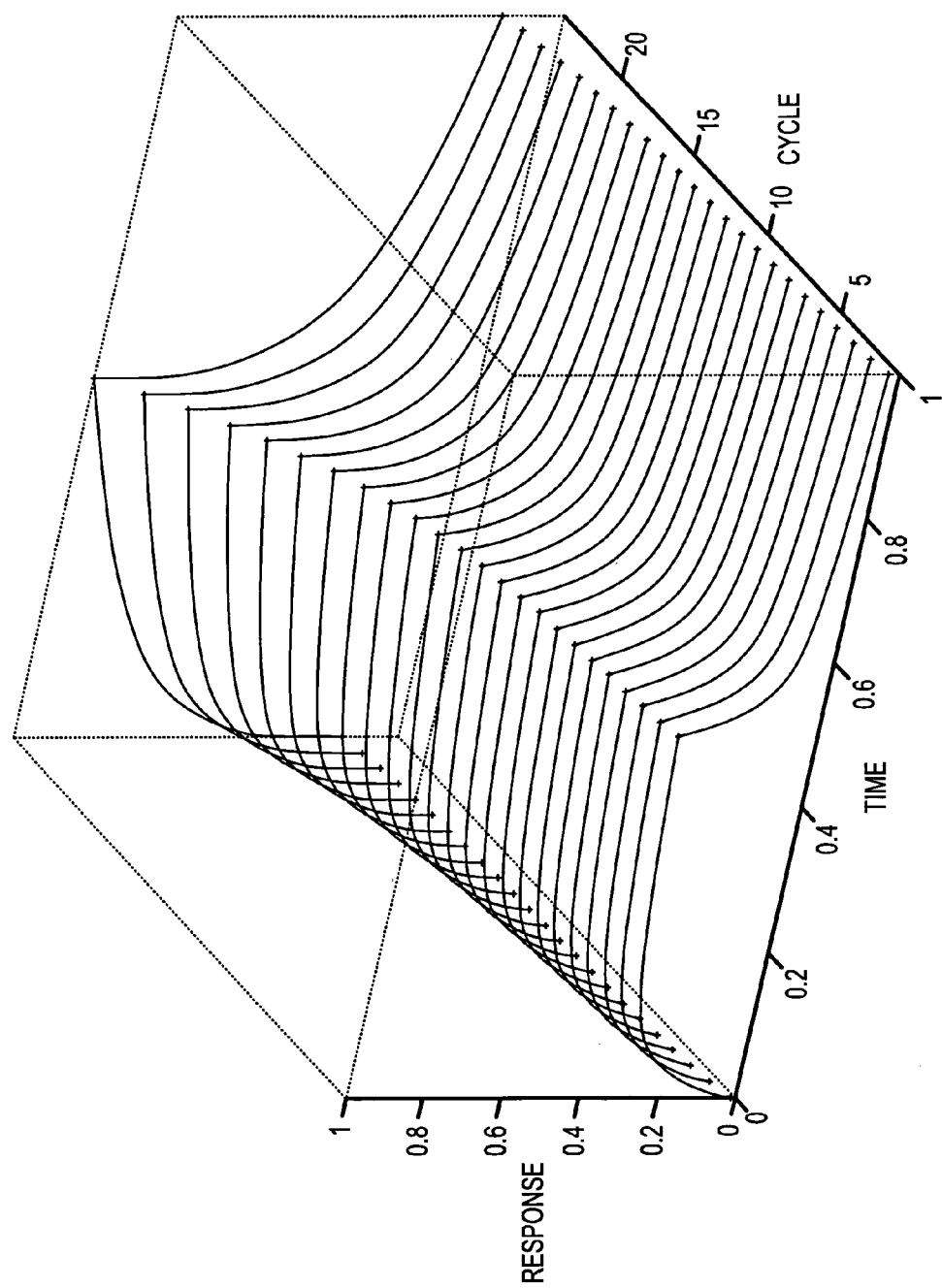
FIG. 12 shows an XYZ response curve to a current-mode excitation.
Figure 13:
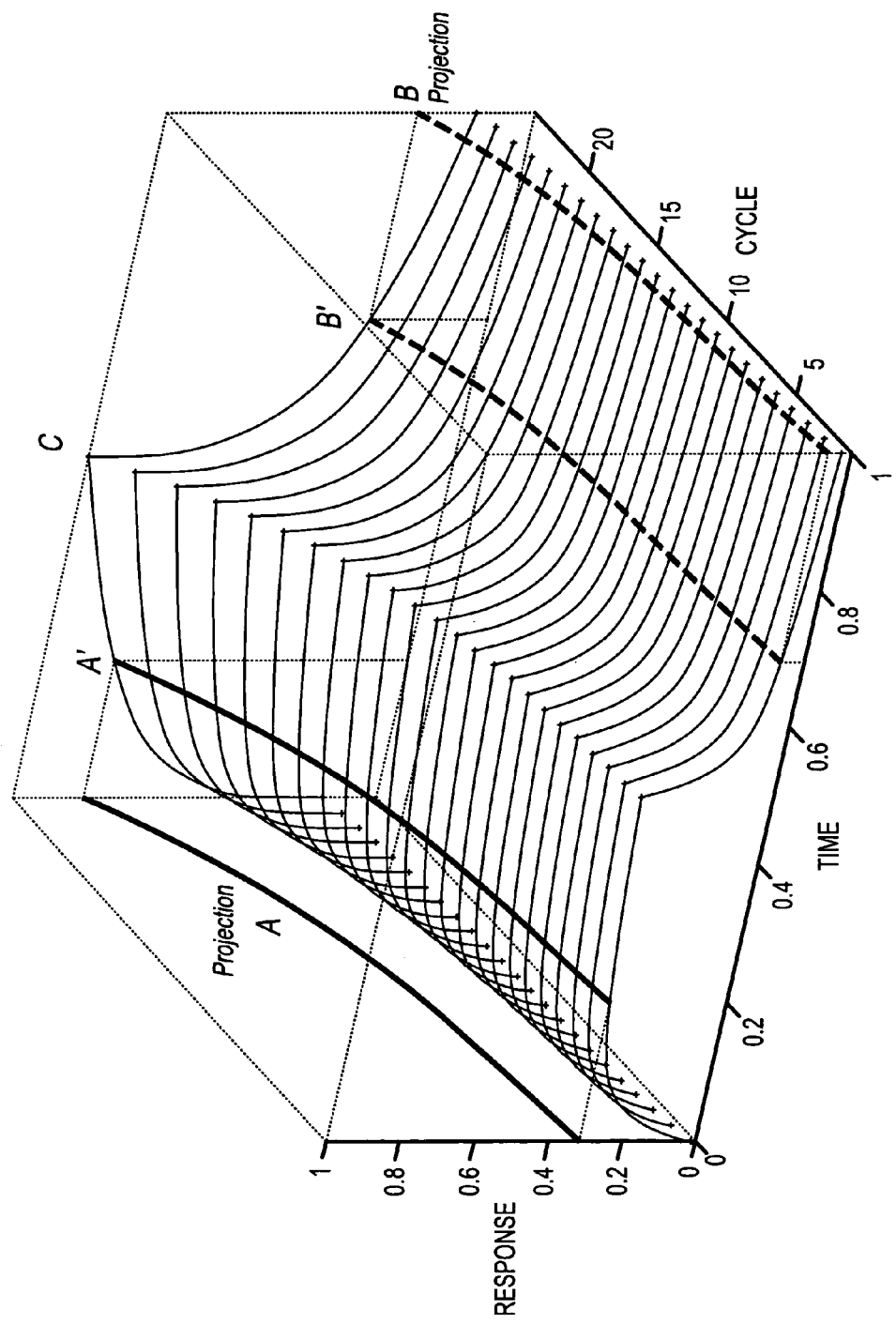
FIG. 13 shows an XYZ response curve with projections to a current-mode excitation.
Figure 14:
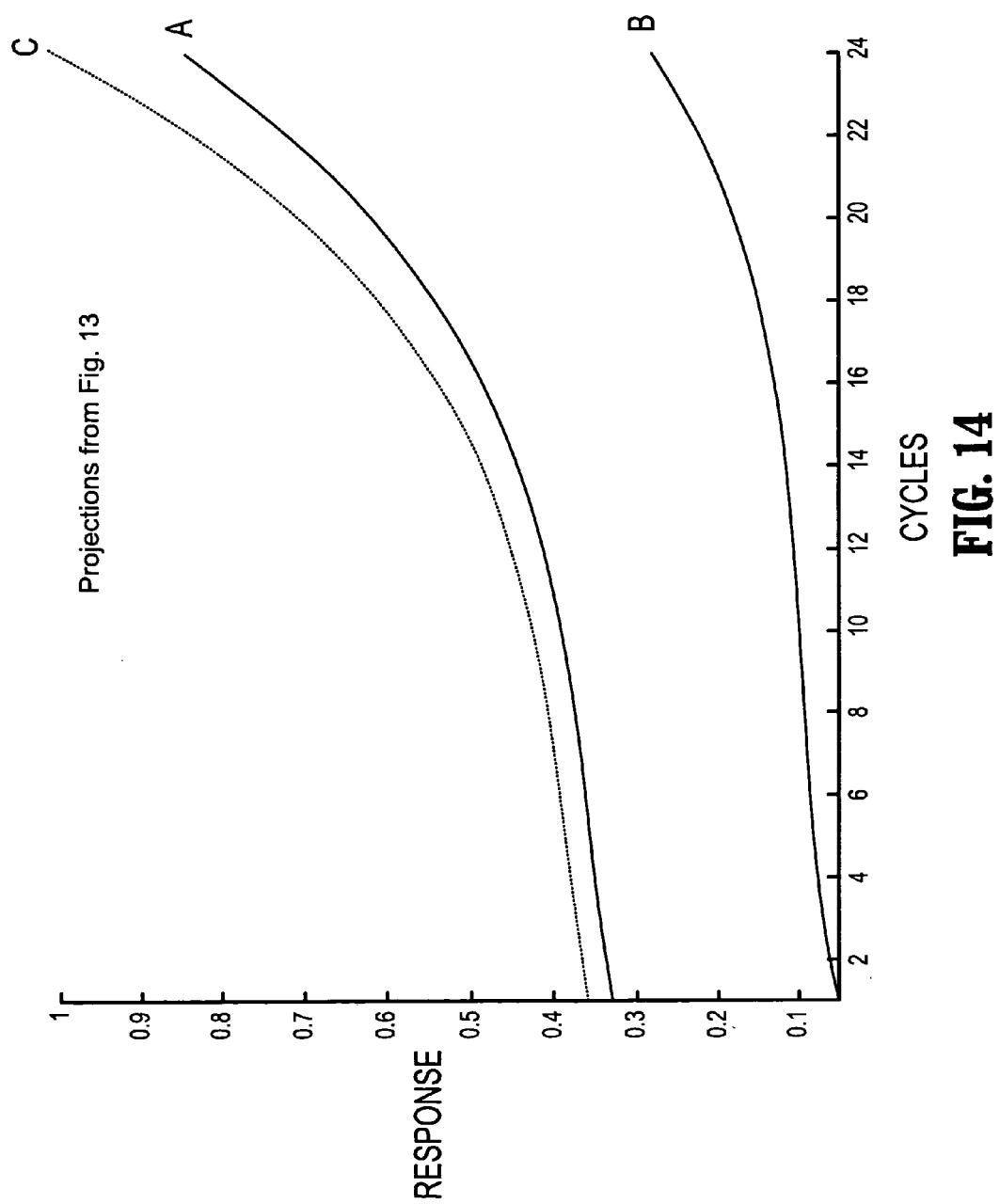
FIG. 14 shows an XY projection of the XYZ response curve of FIG. 13.

FIG. 12 illustrates the response signal from a current mode excitation signal applied to a DUT. The X, Y and Z-axes represent Time, Response Signal Amplitude and Cycle Number respectively. FIG. 13 is the exact data presented in FIG. 13 with the addition of four (4) constant-time projection lines (A, A', B and B'). The response maxima (peaks) for each response signal cycle are also illustrated as a projection line C. FIG. 14 illustrates these projection lines in a two (2) axes format where the X and Y-axes represent Cycle Number and Response Signal Amplitude respectively. Projection lines of this nature and other plotting techniques, applied to linear and nonlinear sampling schedules, can be used for data analysis and system state evaluation.

Symmetric Square Wave Current-Mode Excitation Test Protocol

A specific example of a symmetric excitation waveform (and the typical response waveform for are depicted in FIG. 10. The excitation is provided in the form of a periodic, symmetric alternating current waveform, specifically, a 50% duty cycle (where $\Delta T_1$ equals $\Delta T_2$) amplitude-symmetric square wave comprising one or more pairs of part-cycles similar to 1102 and 1104; by virtue of the amplitude and temporal symmetries, this waveform will exhibit a an time-average value of zero (e.g., has no DC offset component). A SUT exhibiting complete electrical and electrochemical reversibility (viz., at least for excitation amplitudes below some critical threshold) typically yields a response similar to the lower waveform shown in FIG. 10, wherein the shape of each half-cycle of the response resembles an exponentially decaying curve. In actual tests, however, the shape of the response half-cycles may be considerably more complex, and may appear as compound curves comprising multiple "features," or segments, each characterized, for example, by different slopes and curvatures.

Since each half cycle of a symmetric square wave represents a period of constant current excitation, any deviations in the voltage response from an identically shaped voltage-mode square wave will, in a well designed system, be due primarily to the dynamic electrochemical behavior the analyte (e.g., substance under test). A variety of analysis techniques may be employed to provide both qualitative and quantitative measures of the waveform deviations attributable to the effects of the analyte; thence, characteristics of the analyte may be inferred. The symmetry conditions afforded by the use of a 50% duty-cycle square wave excitation permits the use of a number of valuable data analysis methods that have been developed to characterize both the half-cycle response behavior as well as the reversibility characteristics of the SUT.

These data analysis methods may be described as follows. A first analysis type applies time domain response model-based fitting, or parameter estimation, methods to best fit (according to some error measure such as least squares) response data to a response model for each half-cycle. Examples of types of models include but are not limited to the sum of exponentials, series RCL circuits and other linear and nonlinear circuit analogs. In the case of the sum of exponentials, the parameters that are estimated would be coefficients of exponentials and coefficients of the exponents. In linear, and certain nonlinear cases, time constants associated with process in the SUT may be estimated by such methods. Inflection points in particular indicate dramatic variation in processes over time.

A second analysis type involves the frequency domain counterpart of the first analysis type. Transform time series data, or some subintervals or such data (e.g. half cycles), into the frequency domain by numerical or analog Fourier, Laplace, or other transform methods, and apply fitting, or parameter estimation methods, to best (according to some error measure such as least squares) fit a frequency domain response model to the frequency domain data. Frequency domain response models may be based on, but are not limited to, the frequency domain counterparts of time domain models, such as for example sum of exponentials, series RCL circuits and other linear and nonlinear circuit analogs domain analogs of time domain models listed in Analysis Type 1. The frequency domain models may be linear or nonlinear, empirical or mechanistic, etc.

A third analysis type involves investigating congruence (or the lack thereof) between positive and negative half-cycle response(s). To see this graphically, invert the half-cycle response, and plot it together with the positive half-cycle response: any lack of congruence points to process hysteresis effects.

A fourth analysis type involves synchronous cycle-by-cycle sampling allows trend analysis of corresponding $\Delta\tau$ sample points across consecutive cycles; this yields the temporal contour line plots. Analyses similar to Analysis Types 1–3 above may be performed on this trend-line data (to see trends with a single contour, and to compare evolving differences across families of contours). Specific extrema and interior amplitude envelope curves (for corresponding points in consecutive cycles) may be developed.

A fifth analysis type involves investigation of the "low frequency component" of response signals, as may be estimated, for example, by applying a moving-window average over integer numbers of cycles to calculate the "local" average of a response signal for each cycle. The time-series data resulting from such a moving-window average would provide an estimate of the low frequency, or slow transient, component of a response signal. The low frequency component of the response may be called the "bias trend".

In accordance with a sixth analysis type, an improved signal-to-noise ratio is obtained by applying a cycle-by-cycle single-point data averaging technique, whereby corresponding synchronously sampled data points, obtained from equivalent positions within substantially identical consecutive response cycles, are averaged to obtain a single cycle of averaged data that exhibits a reduction in noise proportional to the square root of the number of raw data points used to obtained each of the average data point values. Provided that there is no slowly time-bias-trend (i.e., at frequencies much lower that the frequency of the excitation) detected within the raw data, it may be assumed that the analyte has achieved a state of electrochemical equilibrium, then the point-to-point averaging technique may be applied directly. If, however, a bias trend is detected, then a correction adjustment must be applied to the raw data before noise averaging can be achieved. Provided that the trend of the time-varying bias component of the response exhibits a substantially linear characteristic over a plurality of cycles, it may be quantified and a suitable correction factor may be subtracted from each raw data point to remove the effects of the bias, whereupon the point-by-point averaging technique may be applied to this corrected data, to achieve an improvement in the signal-to-noise ratio proportional to the square root of the number of data points included within each of the averaged values. Another aspect involves a seventh class of analyses, whereby the first and second time derivatives may be calculated for sets of data points with a cycle; similar time derivates may be obtained for data that has been subjected to the noise-reduction averaging technique described previously. By a related eighth method, the values of data samples taken via synchronous sampling at corresponding points in consecutive response cycles may be used to create trend lines representing "constant $\Delta t$ value" contours. Additionally, various geometric methods of characterizing or analyzing curves and/or surfaces (e.g. curvature, torsion, and others) may be employed. A ninth analysis type involves a test protocol(s), which may consist of (a set of) several excitations with different parameters (e.g. amplitudes, intervals, and others), analysis may be based on the comparative variation/deviation of the response characteristics, for example, the transition from the linear time-invariant-response regime to the nonlinear regime with increases in excitation amplitude can be determined. In general, the degree of "reaction reversibility", as indicated by some form of non-linear response, that is exhibited by a system or device being tested will depend strongly on the amplitude of the excitation: for sufficiently small excitations, many systems may experience no irreversible changes (the non-invasive test method), while for sufficiently large excitations, irreversible changes will necessarily be wrought on the system (the invasive test method). All regimes of excitation (e.g., very small, intermediate and very large) may be prescribed within the inventive method.

Electrical System Evaluation

An alternative embodiment, again based originally on chronopotentiometry, is provided by the following set of methods, wherein complex pulse-type current excitation signals are applied to a cell and the concomitant time-varying cell polarization voltage information is measured. The shape (i.e., the magnitude and curvature) of the curves, obtained when the polarization voltage response is plotted as a function of time, provides information about the state or characteristics of the cell. To assess the condition of an unknown cell, its excitation-response profile(s) (e.g., generally the time domain response data) is obtained and evaluated in comparison with previously obtained benchmark data for the particular cell/battery type, via look-up table, logic, or data processing algorithms. The results of this evaluation can be presented either with results displayed via an illuminated 'GO/NO-GO' indicator, quantitatively as percent state or charge, or with a specific indication of probably health condition or failure mode.

This technique may be applied in laboratory instrumentation, field test units, factory (cell/battery manufacturing) inline tests, as embedded subsystems for power system diagnosis, battery charger control and uninterrupted power systems (UPS) applications. In many cases, cost effective embodiments of the technique (for specific applications) may be achieved by integration directly in silicon.

The Lithium Sulfur Dioxide Primary Cell

The $LiSO_2$ cell employs lithium as the anode and sulfur dioxide as the active cathode material. The electrolyte is typically an organic solvent such as acetonitrile containing lithium bromide to provide ionic conductivity. During discharge, the lithium is oxidized to $Li^{+1}$ to release an electron to the load circuit. Two lithium ions then migrate toward the cathode area where they combine with two sulfur dioxide molecules, along with a pair of electrons (from the load via the cathode circuit), to form lithium dithionate ($Li_2S_2O_4$). In cells where lithium is the stoichiometrically limiting electrode, discharge terminates when it is all consumed. Otherwise, discharge ceases when the cathode becomes blocked by the precipitation of the discharge product.

When the $LiSO_2$ cell is left in an open circuit condition, the discharge reaction proceeds directly at the anode, forming a thin coating of lithium dithionate that serves as a highly effective passivation layer. This prevents further reaction and self-discharge, leading to exceptional shelf life. After extended storage times, the cell's terminal voltage, when first connected to a load, appears somewhat depressed (the 'voltage delay' effect). As the discharge current removes the passivation layer, the terminal voltage soon recovers to its expected value. It should be noted that the open circuit voltage of a fully 'passivated' cell can rise more than 50 millivolts higher than its nominal value.

A fully charged cell in normal use exhibits a nominal open circuit terminal voltage of about 2.95V. Upon connection to a load, the terminal voltage first undergoes a rapid drop, followed by a recovery during the next several minutes as it climbs back to a constant value determined by the load current. The value of the 'recovered' loaded terminal voltage remains exceptionally constant (for a given load current) throughout the useful life of the cell, and not provide a good indicator of state of charge. Upon cessation of the load current, the open circuit voltage (OCV) will rise, eventually approaching the nominal value very closely. Thus, OCV is not suitable as an indicator of state of charge.

Synopsis of the Technique

According to the original time domain spectroscopy method, a symmetric, bipolar square wave current (that is, of alternating positive and negative sign) is impressed on an electrochemical cell (or battery of cells) and the resultant time dependant polarization voltage response is measured. The excitation signal current is properly adjusted to elicit a very small voltage response (typically 0.1% of its nominal voltage) with respect to the physical and chemical characteristics of the cell. Due to the symmetry of the excitation (both in the time and amplitude domains) the method is fundamentally non-invasive, in that the net energy state of the cell is not significantly altered by the test process itself. Thus, such a test can be repeated many times with virtually identical results. Since the excitation signal is periodic, with constant peak-to-peak amplitude, the response also will exhibit constant peak-to-peak amplitude response throughout the entire test protocol duration. The information contained in the response signal represents the actual time domain response of the electrochemical system, and may be manipulated (via suitable mathematical transforms) to yield frequency response information. In addition, values for the elements of an equivalent electronic circuit model can be calculated. Finally, the characteristics of specific electrochemical processes often can be derived directly from graphical analysis of the time domain response plots.

When it is desirable to quantitatively evaluate the state of charge of a $LiSO_2$ (single use) battery, an extension of the excitation-response method is employed. A pulsed unipolar excitation signal is employed, with the amplitude scaled up to ensure a non-linear 'non non-invasive' response. In this case, both the wave shape as well as the amplitude envelope of the resultant polarization voltage response vary as a function of time, and using these data conjointly allows an accurate determination of the characteristics of cell condition and state of charge.

The excitation signal (FIG. 15) is a 50% duty cycle rectangular square wave current, comprised of equal duration periods of constant discharge current and zero current (e.g., open circuit), so that the average amplitude of the excitation wave form is equal to one half the peak current value. A test protocol commences with a discharge pulse of $\Delta t$ seconds, followed by a rest period of $\Delta t$ seconds, and so on for a number of repetitions, ending with the last rest period of $\Delta t$ seconds. The duration of the pulse depends on the particular cell type tested, and must be sufficiently long to ensure polarization of the electrochemical interface. For example, the pulse duration may range from 0.1 to 5 seconds. The amplitude of the current is sufficiently large to produce a slight net discharge of the cell (about 0.1% of its nominal capacity) during a single test. In practice, suitable current levels fall between $C_{1\text{-}hr\text{-}rate/2}$ and $C_{1\text{-}hr\text{-}rate/8}$, where $C_{1\text{-}hr\text{-}rate}$ is the nominal amp-hour capacity of the cell.

Figure 16A:
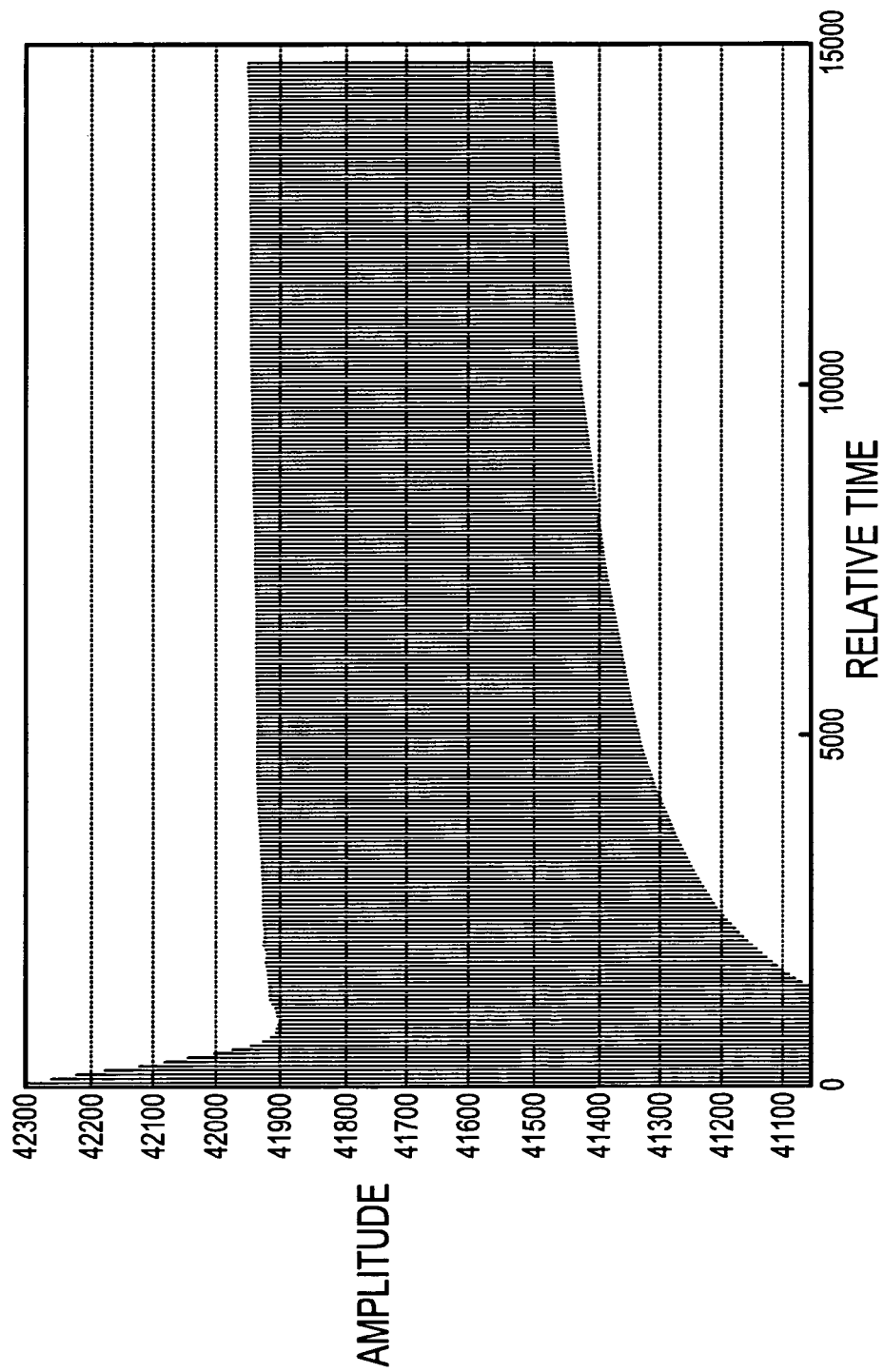
FIG. 16A shows a plot of test protocol data for 255 cycles.
Figure 16B:
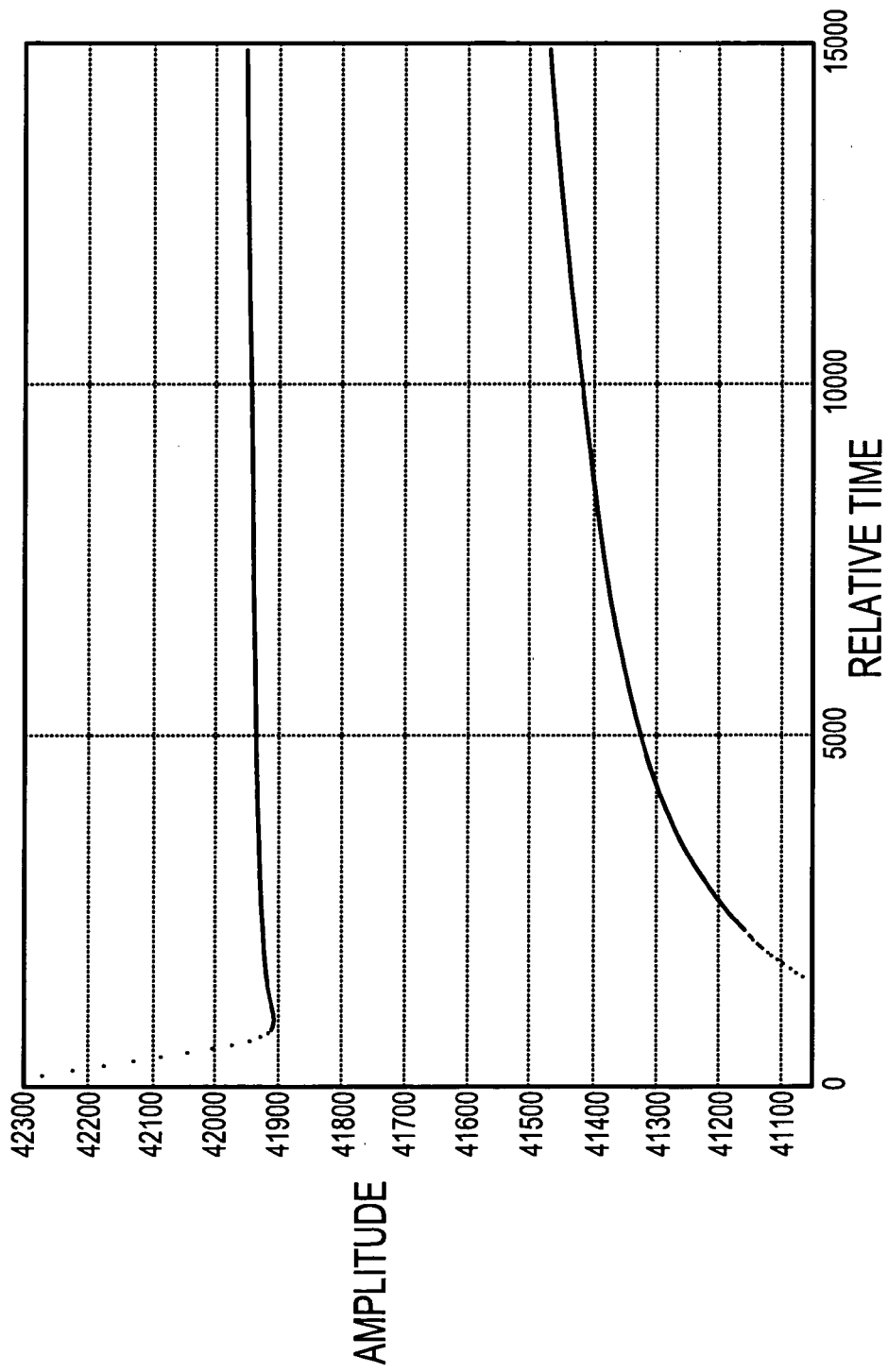
FIG. 16B shows a plot of extrema points.
Figure 16C:
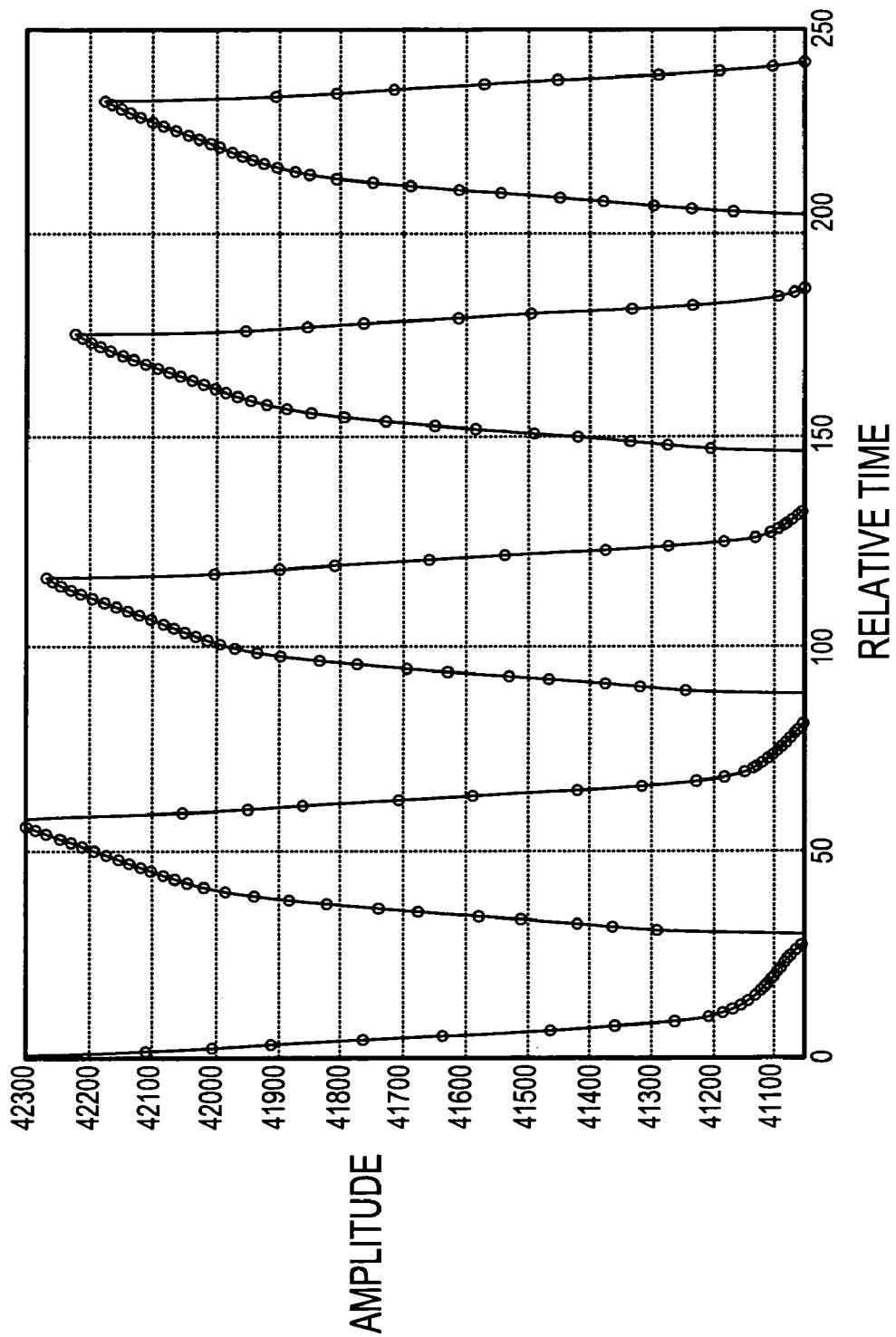
FIG. 16C shows overall envelope amplitude plots.
Figure 16D:
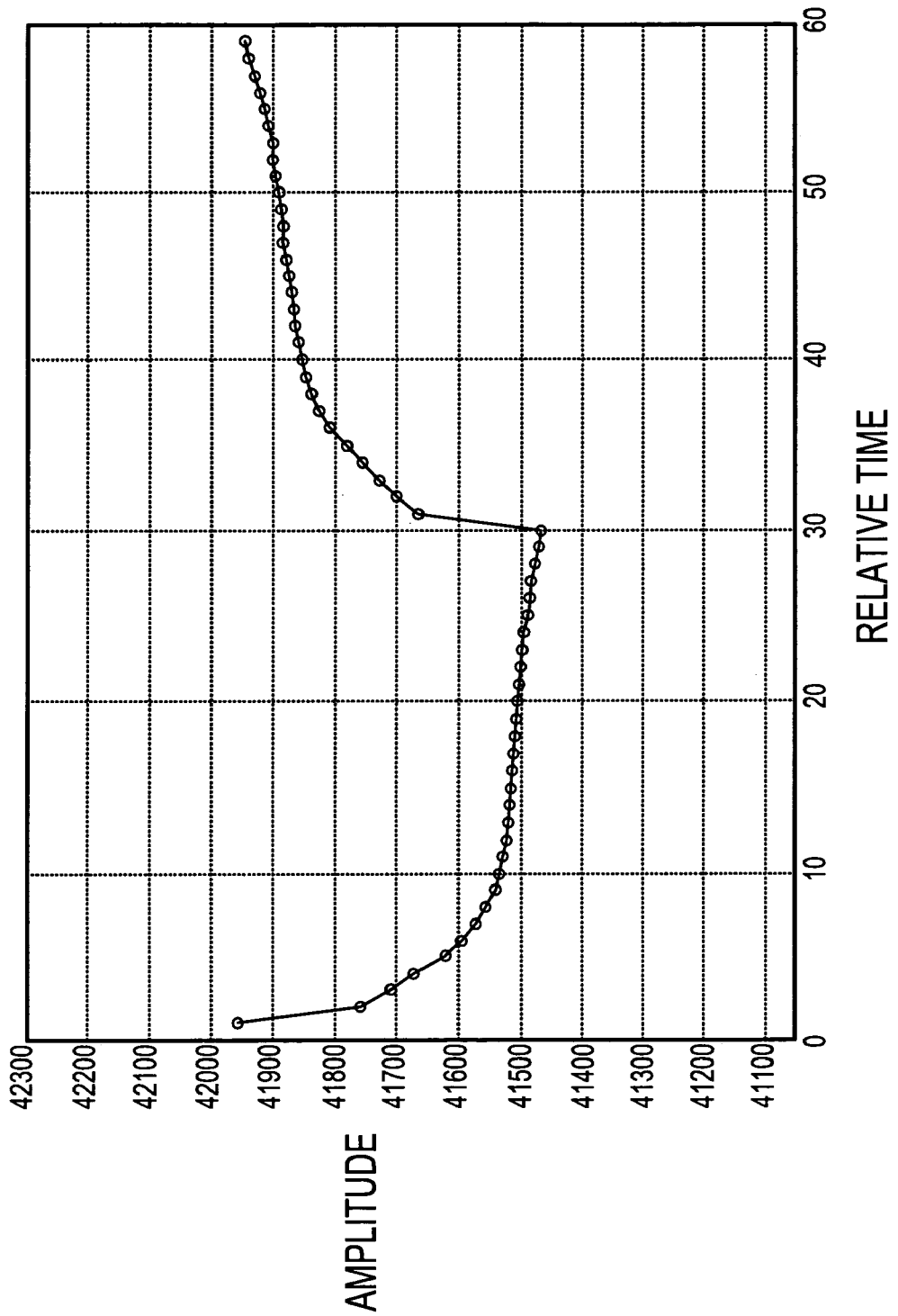
FIG. 16D shows overall envelope amplitude plots.

The duration of each pulse is very well controlled (e.g., the variation between consecutive one second pulses is less than 2 nanoseconds, equivalent to $\frac{1}{500}$ ppm), allowing synchronous data sampling techniques to be used. The cell's voltage during each charge and rest pulse is sampled under an identical sampling schedule. Thus, for all pulses, the $N^{th}$ sample in each pulse is taken precisely k microseconds after the beginning of the pulse. This allows 'equivalent' points in consecutive pulses to be directly compared. FIG. 16A provides a plot of the data (for all 255 cycles) obtained in a typical test protocol. Of particular importance are the overall waveform extrema (i.e., the maximum values of positive and negative excursion during each pulse event), which are readily obtained by this method. When the extrema points alone are plotted in FIG. 16B, the result is the amplitude envelope signature of the cell. The overall envelope amplitude (that is, the peak-to-peak cell voltage excursion), as well as the shape of each individual response waveform, changes considerably during the course of the test protocol (see FIGS. 16C and 16D). By direct inspection of this type of plot, the relative condition and state of charge of the cell can be estimated. Suitable algorithms, employing previously obtained baseline information (extracted by various means and applied to a full range of 'charge state' data from the target cell type), can be employed to automate the measurement/analysis process. In addition, detailed analysis of the raw data provides considerable insight into the behavior of the cell, and allows individual electrochemical processes to be identified and precisely quantified.

Description of the Time Domain Spectrometer Device

The method applies well-controlled current pulses to the cell. To permit observation of the fast electrochemical events that occur at the onset of discharge current excitation, the rise time of the current pulse is significantly shorter than the response time of the fastest process of interest. For example, a pulse rise time on the order of one microsecond may be used for small cells that exhibit low inductance. For larger cells this criterion may be relaxed by at least an order of magnitude, since the internal inductance of large cells is significant and overwhelms the observable response arising from the very fast initial processes. To avoid errors, particularly when smaller cells are tested, the output-offset current should be not greater than 0.01% of the pulse amplitude. The current driver itself is preferably embodied as a precisions voltage controlled current source, operating to ensure pulse shape accuracy in the neighborhood of zero current. A simple switched current source (of, bipolar transistor with scaled emitter current-setting resistor) will suffice for large cells, where the inevitable errors (pulse overshoot or ringing) at turn-on and turn-off become unimportant.

Pulse amplitude accuracy is ensured through the use of a low skew, programmable waveform generator that incorporates a very stable voltage reference. For laboratory applications, this reference should provide a very low noise output, with less than 0.5 ppm/degrees centigrade drift. For less demanding commercial applications, this criterion may be relaxed by an order of magnitude. The pulse amplitude is parametrically adjustable, and can be changed to any value for each successive pulse. This feature is useful for cells, which require a substantial depolarizing event (one or several higher amplitude pulses) at the beginning of a test protocol.

Proper pulse generation for precision duration/sequence time is critical to accurate measurement. Nanosecond duty-cycle skew is achieved through the use of high-speed logic and sub-nanosecond, balanced analog witching techniques. Pulse durations and the overall protocol sequence are programmable.

To measure the cell's response, a 16-bit high-speed analog-to-digital converter is employed. The sampling schedule may be either constant rate (fixed sampling interval), or parametric-by-pulse. In the latter case, each pulse is sampled according to the same non-linear schedule whereby the intersample time delay increases between successive points: an exponentially increasing series of sample intervals is preferred, but other types of schedules may be employed for specific applications. A useful parametric-by-pulse sampling schedule provides many samples just after the onset of each pulse where fast events tend to occur, and less samples later on as the responses of slow electrochemical processes dominate, which can significantly reduce data processing and storage requirements. For particular applications (e.g., integrated electronic circuit implementations), a very few data points may suffice for effective determination of cell state and condition, allowing inexpensive sampling methods to be used.

To allow batch mode operation, the devise is equipped with an internal micro controller that supports the user interface (display and parameter input) and provides real time process control including serial communications to an external computer.

Description of the New Measurement Technique

When allowed to stand in an open circuit condition, $LiSO_2$, cells spontaneously develop a layer of lithium dithionate on the surface of the anode. Once formed, this layer provides surface passivation, retarding further self discharge. An addition effect of this layer is manifested as an initial 'voltage delay' when a load is connected: The cell's terminal voltage undergoes a short 'dip' and recovers to its expected value within a short time, as the passivation is removed. When a passivated cell is measured by traditional means, its observed electrical characteristics does not accurately reflect its condition and state of charge. Both the apparent impedance of the cell, as well as its open circuit voltage exhibit elevated (and indeed fairly similar) values over a broad range of charge states. Therefore, before any meaningful measurement is possible, the passivation problem must be disrupted (de-passivated).

De-Passivation is achieved by subjecting the cell to a brief interval of relatively strong discharge current; whereafter parameter measurement yields useful data. The simplest technique employs a constant current discharge event for several tens of seconds, followed by an open-circuit (relaxation) period. By measuring the progressive changes in the cell's terminal voltage during both periods, a reasonably accurate measure of condition and state of charge can be obtained. To achieve effective de-passivation, however, the initial current must be a substantial fraction (about one quarter) of the $C_{1\text{-}hr\text{-}rate}$. While this is satisfactory for new and 'healthy' cells, should such a substantial current be applied to a severely depleted unit, it can cause the cell to become totally polarized (zero terminal voltage) and sometimes in fact, reverse biased. Under these conditions, lithium metal can appear at the cathode, leading to the rapid evolution of sulfur dioxide gas (venting), and possibly cell rupture as a result of a rapid exothermic reaction at the cathode.

The present method employs a repetitive series of discharge pulses separated by equal duration 'rest' periods where the cell current is zero. A typical test protocol consists of a first 1 ampere discharge pulse lasting 655 milliseconds (equivalent square wave frequency=0.762 Hz), followed by a 655 millisecond rest: this charge/rest pattern is repeated 255 times. A 16-bit, 50 kHz sampler is synchronized with the excitation pulses, so that 65536 equally spaced samples are acquired during each pulse. The first sample for each pulse occurs 20 microseconds after the edge transition (i.e., at the beginning of discharge current, and beginning of 'rest'), while the last sample in each pulse is taken at its very end (that is, at its maximum amplitude point). For specific applications, these critical parameters (pulse current amplitude, pulse duration, protocol sequence length) can be adjusted accordingly.

The raw data (here the sampled cell terminal voltage) consists of a series of points that define waveforms whose shape and magnitude undergo substantial, progressive changes throughout the test protocol. The nature and meaning of the data is discussed below.

General Description of the Time Dependent Polarization Voltage

The electrochemical systems of interest (here, single-use energy storage cells and batteries) rely on several distinct chemical and physical processes for their operation. The actual electric current produced by primary cells results from the transfer of electrons between the two reactive electrode constituents during a Faradaic oxidation-reduction reaction. This reaction causes an electric potential to develop between the cell's terminals, which can drive current (the electrons) through an externally connected load. An intact cell is capable of delivering current until at least one of the necessary chemical species (i.e., the electrodes' active constituents) is depleted or otherwise rendered unavailable for chemical reaction. A cell becomes totally discharged when either one of the species is entirely used up, or one of the electrodes has become 'blocked' (such as by the precipitation of discharge reaction products). The disclosed method enables the details of these reactions to be detected and recorded, allowing full characterization of a cell's condition.

To facilitate immediate comprehension of the information contained in the (potentially) millions of raw data points obtained in a test protocol, it is useful to subject the raw data to a transformation prior to visual inspection and graphic analysis. The transformation consists of decimating the raw data (originally obtained by sampling at a constant, high frequency), to leave only a series of exponentially spaced points. Since each sequential data point is assigned an integer index as it is acquired, it is simply a matter of selecting among the raw data points according to an exponential series of integers (e.g., 2, 3, 4, 6, 8, 12, 16, 23, 32, 46, 64 . . . ) to achieve the desired decimation. This technique serves to provide high temporal resolution early on in each pulse event when fast processes occur, and reduce data volume later on as slow events predominate.

Figure 17A:
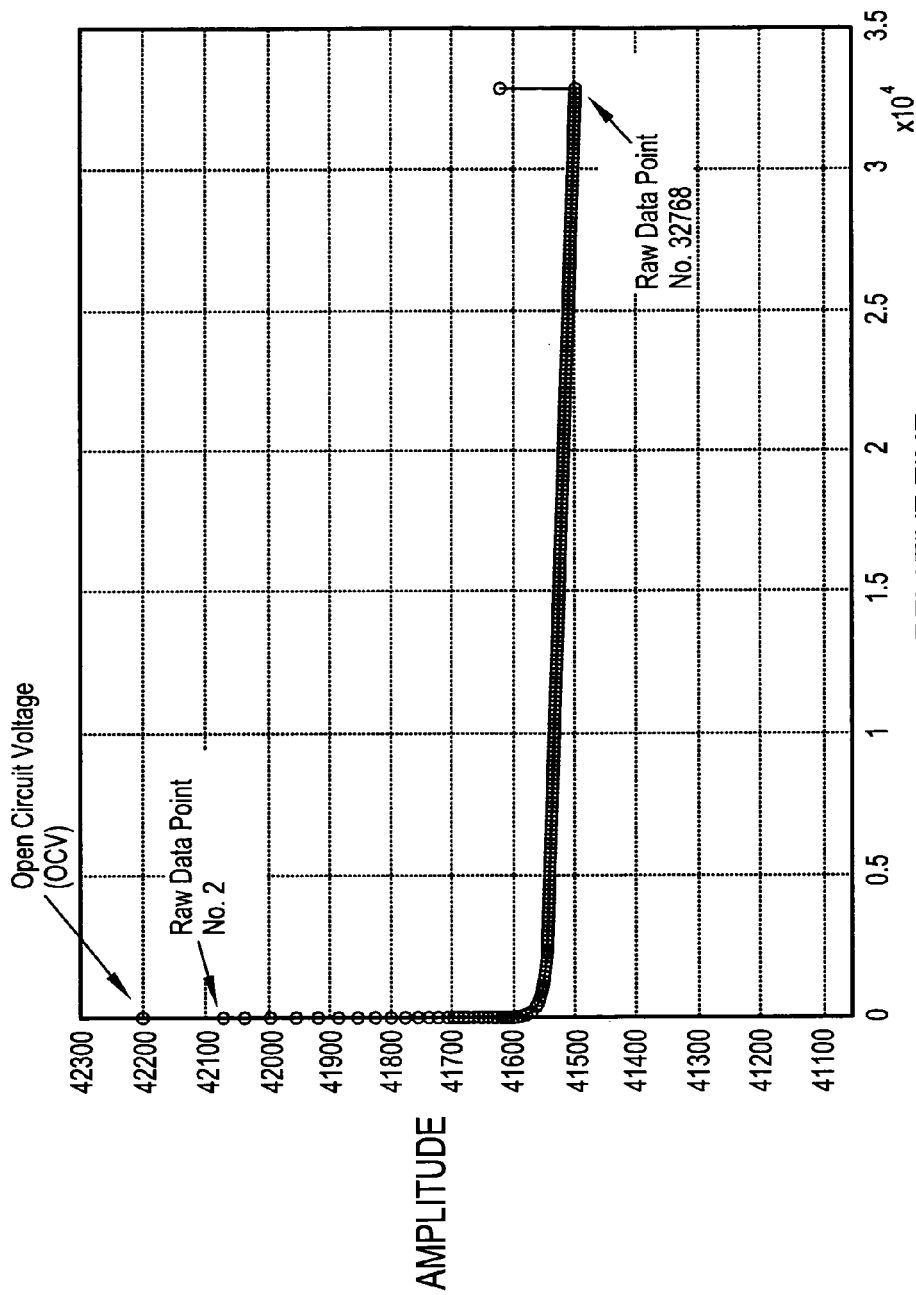
FIG. 17A shows a linear plot of raw data.
Figure 17B:
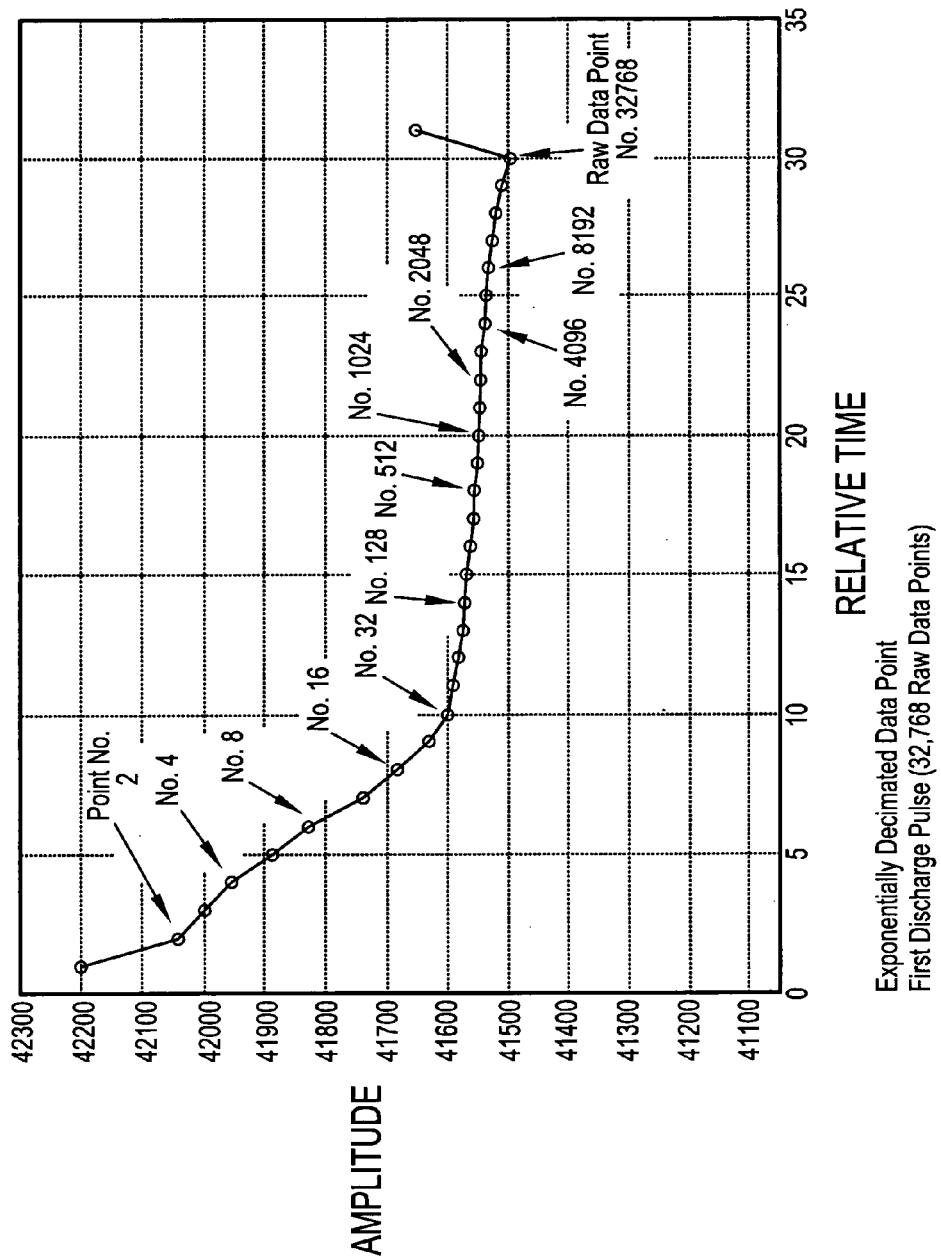
FIG. 17B shows an exponentially decimated data plot.
Figure 17C:
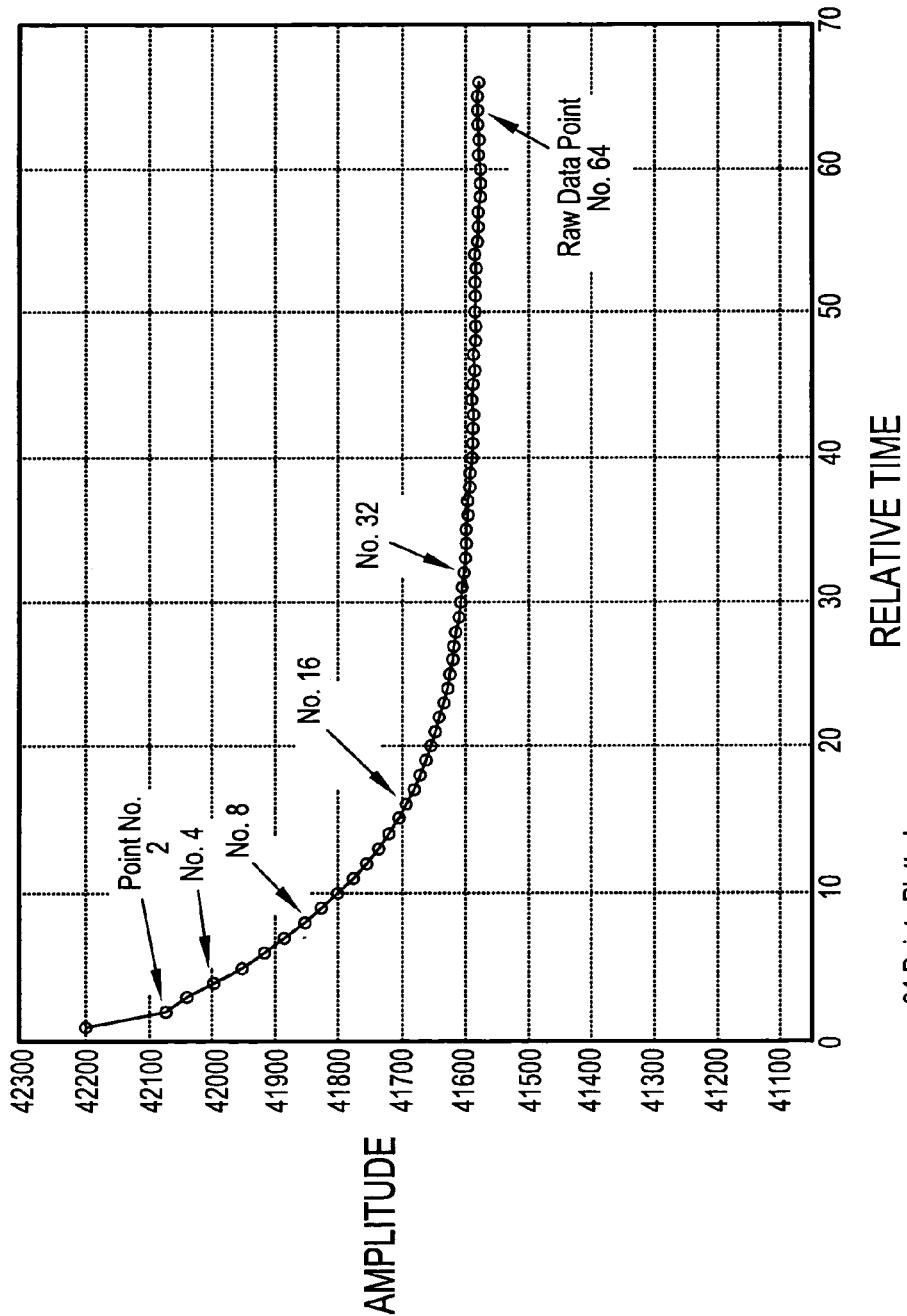
FIG. 17C shows a raw data plot with a linear time scale.
Figure 17D:
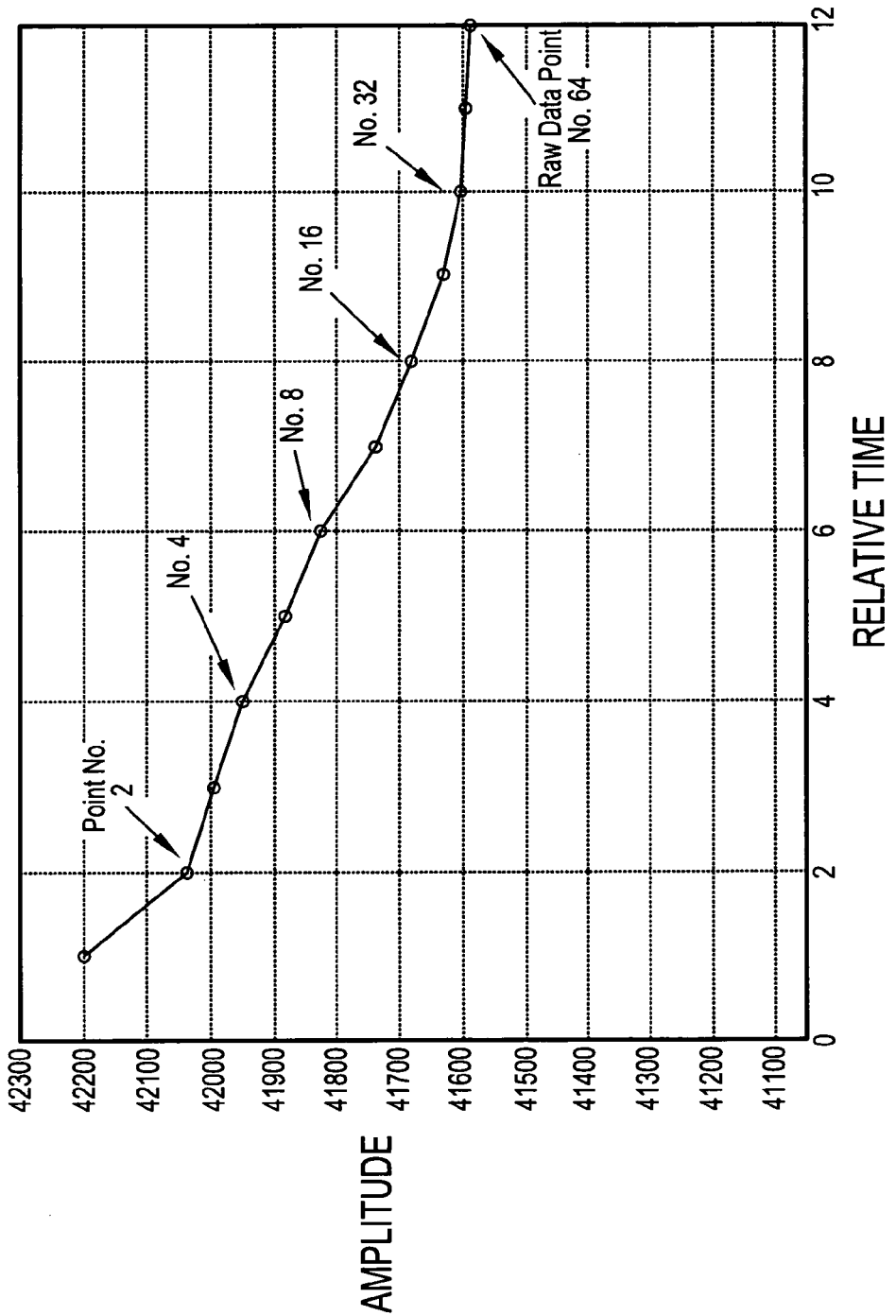
FIG. 17D shows an exponentially decimated data plot.

A direct comparison between linear data plots and an exponentially decimated one is provided by FIGS. 17A through 17D. In FIG. 17A the raw data (32768 points) showing the first discharge pulse appears as a 'tilted-top' rectangular pulse with an almost vertical front edge. However, upon examination of the decimated version, FIG. 17B, the linear slope of the first 32 data points (now plotted in semi-log style) indicates an exponentially decaying function. The fine detail of FIGS. 17C and 17D make this completely apparent. By employing the exponential transformation, electrochemical process details become immediately accessible in a single graph. Referring again to FIG. 17B, the region between points 32 and 8192 appears very straight, indicating a second, longer time constant exponential. Toward the end, a downward curvature appears, indicating yet another process coming into play in the cell. Because of the utility of the exponential transformation, all of the plots provided (except actual raw data, which is plotted on a linear time scale) have been created by this method.

Figure 15:
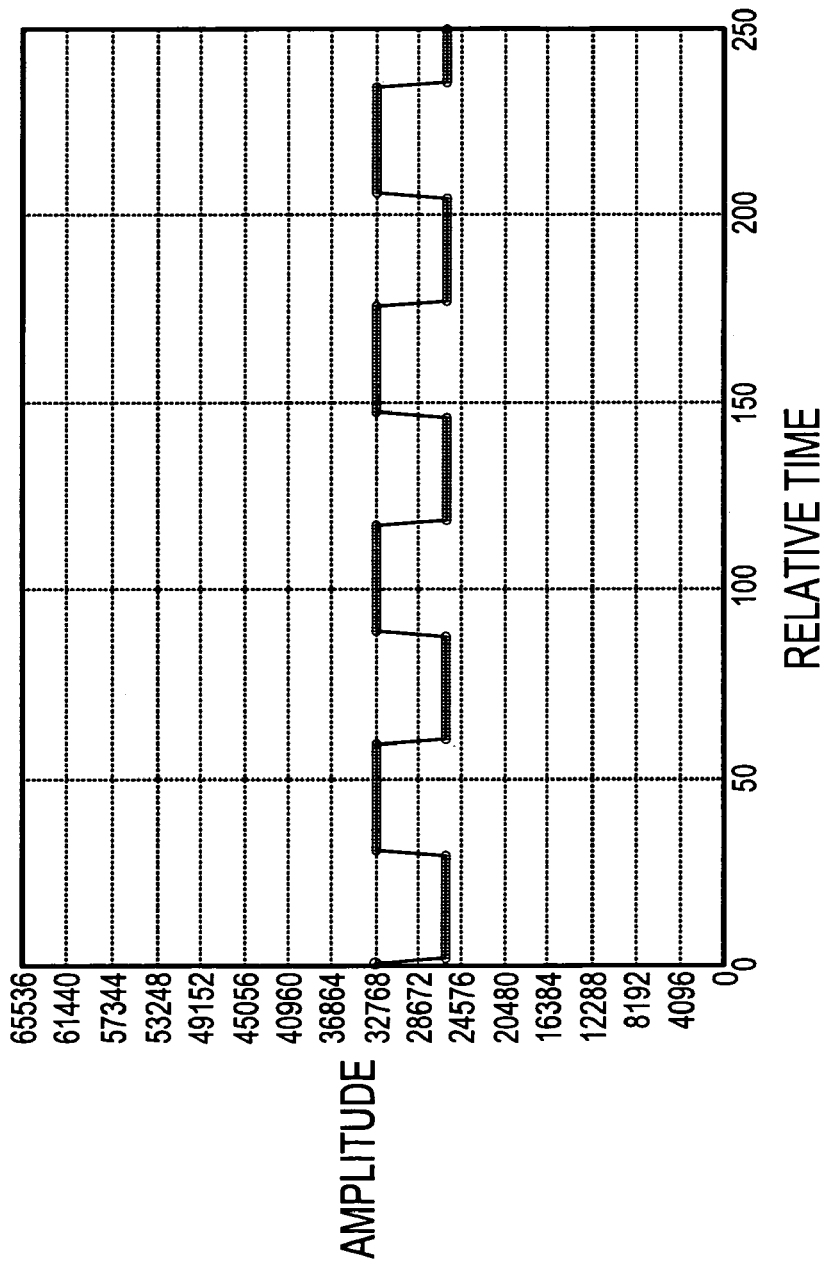
FIG. 15 shows an excitation signal.

The following paragraphs provide a summary of the several distinct processes that determine the shape of the plot obtained from typical test protocols; the data from several actual tests (with various test protocols, as specifically noted) have been used. The important characteristic of each distinct region of the plots is the associated time constant, or more particularly, the precise shape of the voltage-time curve, which is indicative of the predominating electrochemical process. The 'y' values shown on all the plots are 5 digit integers corresponding to a 20 volt scale, where 65536 is 10 volts, 00000 is −10 volts, and 32768 is zero volts. FIG. 15 is a plot of the voltage developed across a 2 Ohm resistor by the rectangular shaped excitation current (0.762 Hz, 50% duty cycle, −1 amp peak).

Figure 18A:
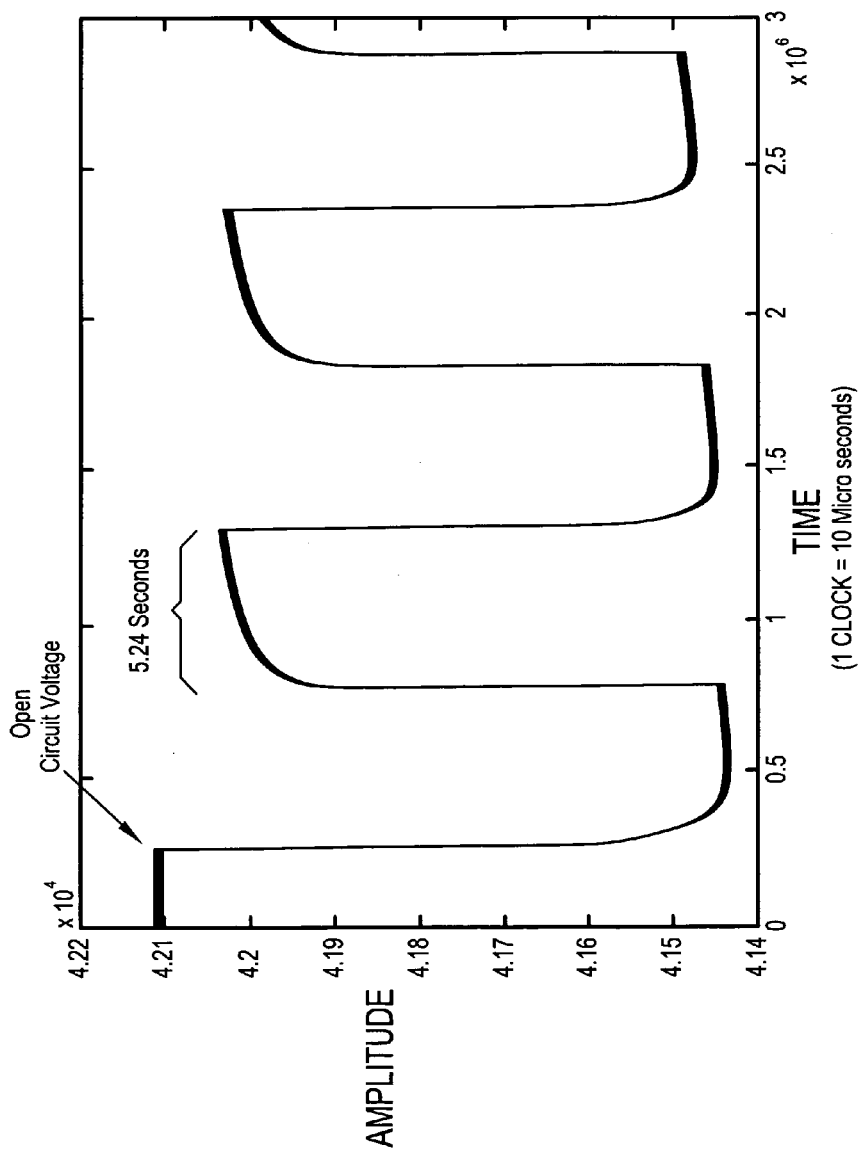
Figure 18C:
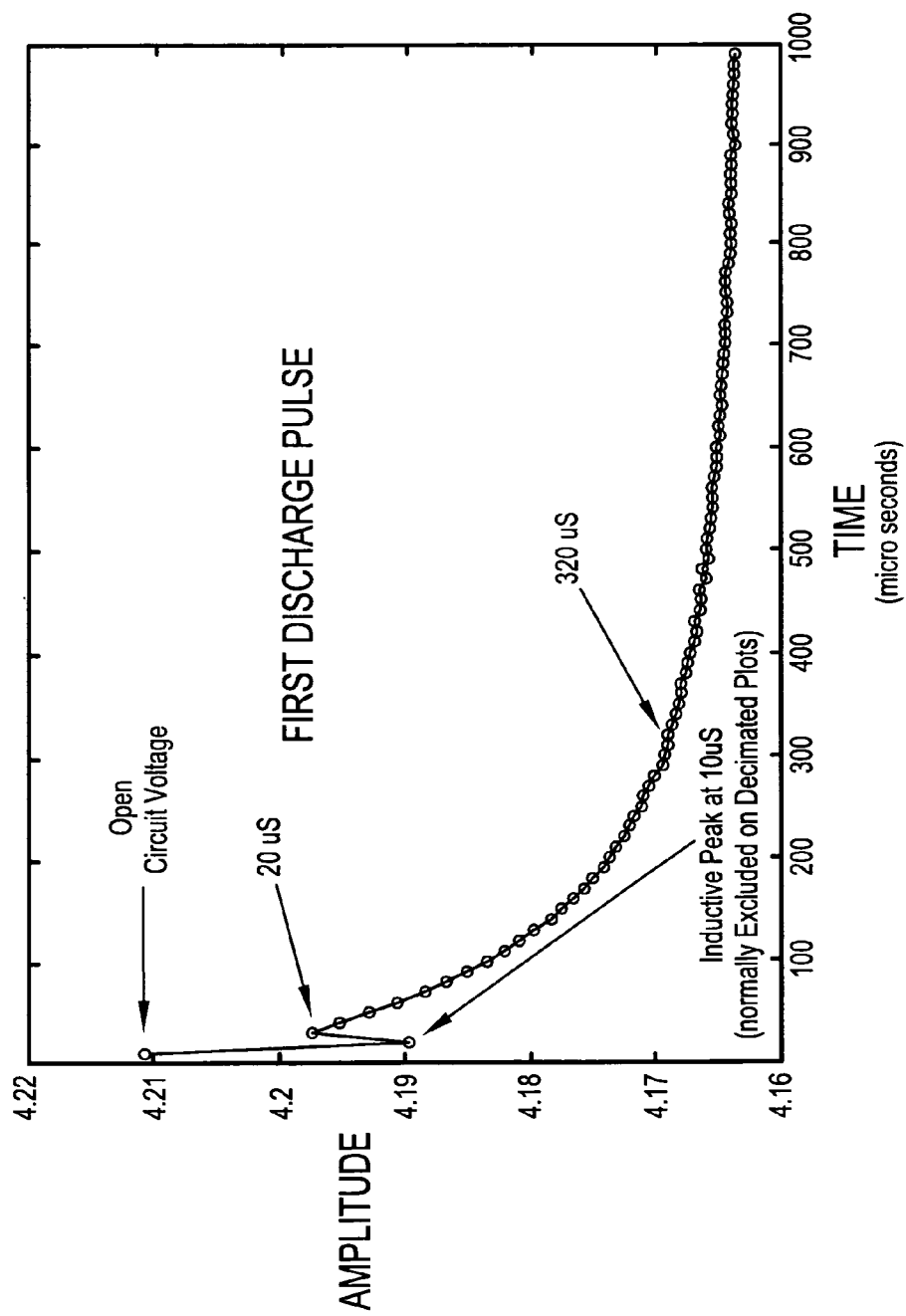
Figure 18D:
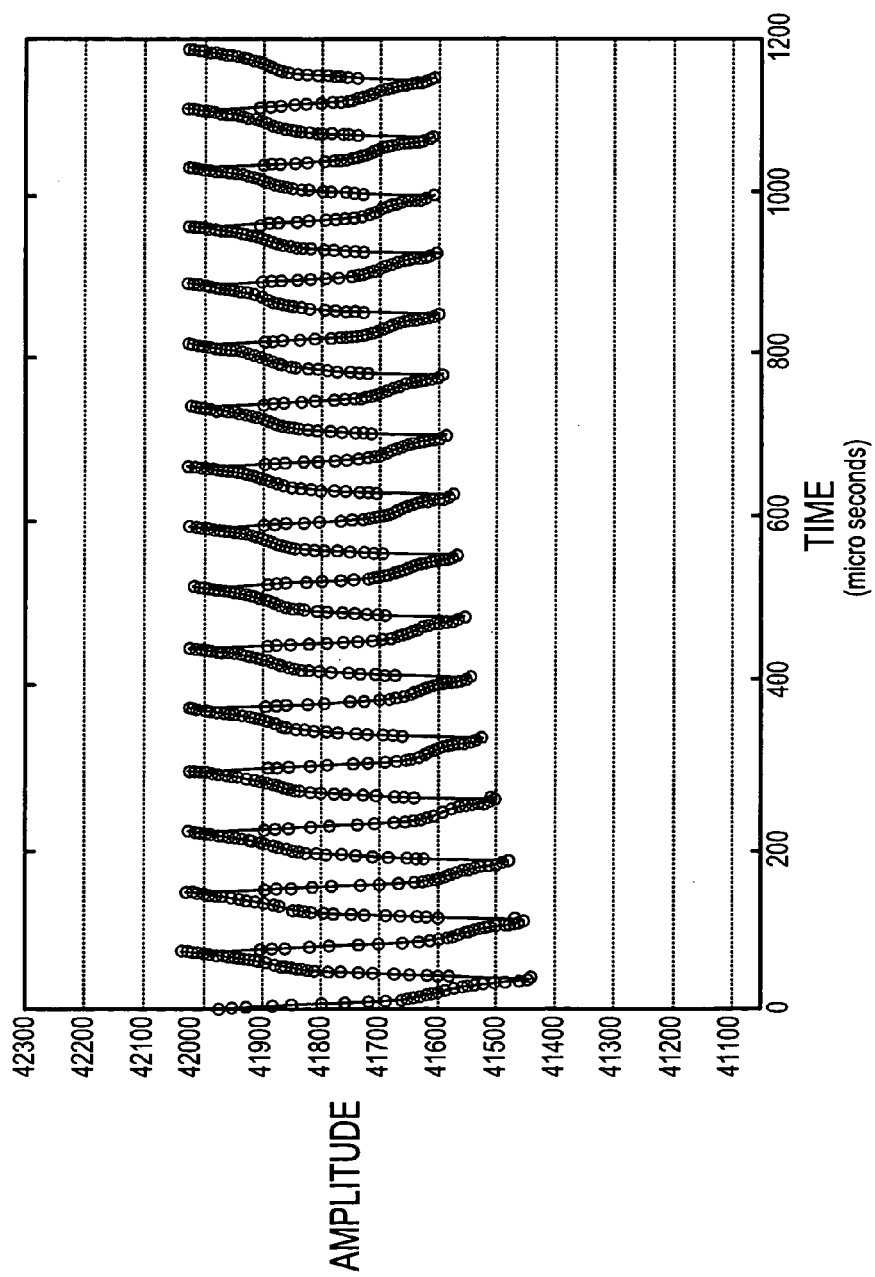
FIG. 18D shows a plot for the entire protocol.
Figure 18E:
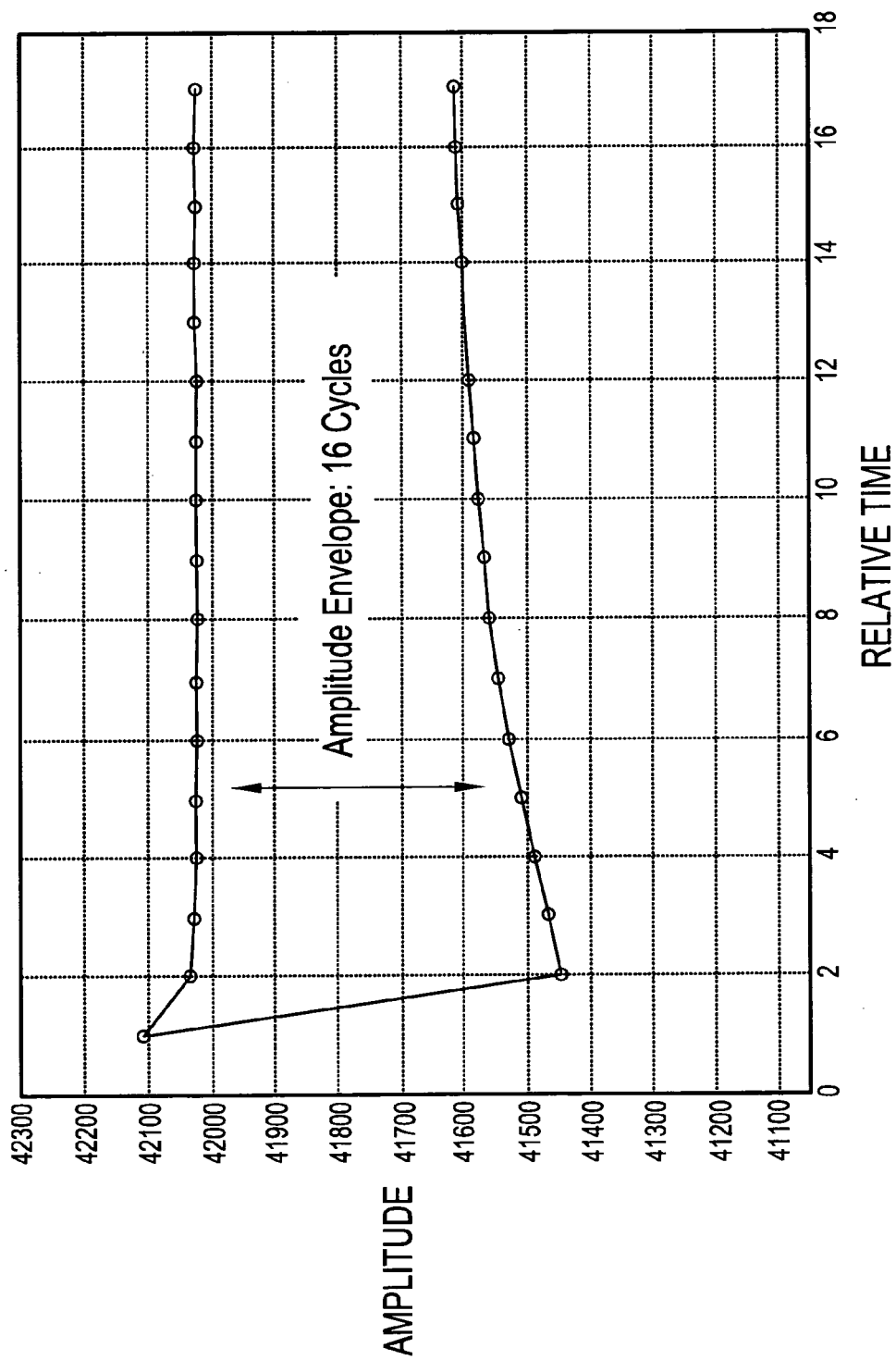
FIG. 18E shows a plot of the amplitude envelop signature of the cell.

The first data to be considered was obtained from a nearly fully charged cell that had been left on 'open circuit' for more than 12 months. The protocol consisting of 16 discharge/rest cycles (at 5.24 seconds per each charge or rest pulse), with a peak discharging current of 1 ampere. A 100 kHz sampling frequency was used to ensure high resolution of fast processes. FIGS. 18A, 18B and 18C provide plots of the raw data at several levels of detail. Note that this cell had not been subjected to a large depassivating event (such as a protracted discharge), so there is still evidence of residual passivation in the rounded leading edges of the raw data waveforms. FIG. 18D provides a plot of the entire protocol, after the exponential decimation has been performed; the 'y' value of the first plotted point represents the open circuit voltage of the cell prior to the onset of excitation. FIG. 18E provides a view of the cell's amplitude envelope signature which is obtained by extracting and plotting only the highest and lowest points of each waveform, with the addition of a first reference point corresponding to the open circuit voltage of the cell prior to excitation.

Figure 18F:
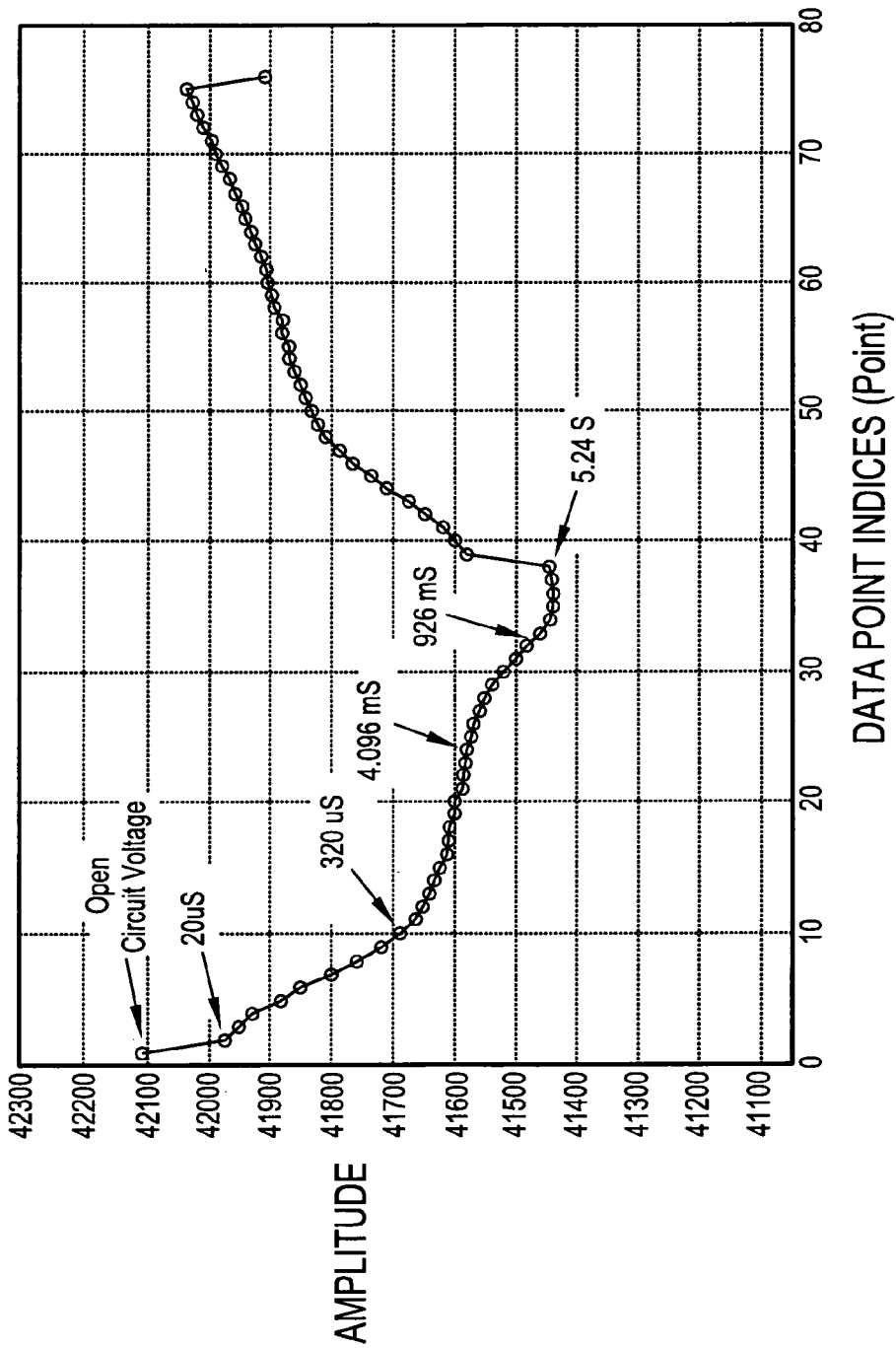
FIG. 18F shows an initial waveform plot of an exponentially increasing inter-sample time transformation.

Recall that (other than in raw data plots) all figures display data that has been exponentially decimated with respect to time. Under this transformation, all the points appear evenly spaced along the 'x' axis, but the elapsed time between adjacent sample points within each pulse event increases by a factor of 1.414 as you move to the right. The net effect is that the plots provide a semi-log representation of the raw data, emphasizing the details of fast reaction processes. Unless otherwise noted, the exponentially decimated sampling sequence begins anew after each step transition. An example of this exponentially increasing inter-sample time transformation is explicitly shown in FIGS. 18F and 18G, which provide close up details of the initial and final waveforms, respectively, of the protocol.

Following the onset of either a discharge or rest pulse, the first important event that is observed is a virtually instantaneous 'step' transition in the overall cell voltage (a brief inductive overshoot is apparent in FIG. 18C, and if present, this first 'outlier' point is omitted from other plots). Because even the most rapid chemical reactions take some time to occur, such a step-wise transition in cell polarization (that is, an event having a time constant very close to zero) is attributable to the voltage drop produced by the constant current flowing through the equivalent Ohmic resistance of the cell (i.e., its real impedance component). As such it is linearly proportional to the current's amplitude. On the plots, the 'step' appears as a distinct, straight-line segment at the boundary between adjacent pulse events. Three of these 'steps' can be seen clearly in FIG. 18F.

Figure 18G:
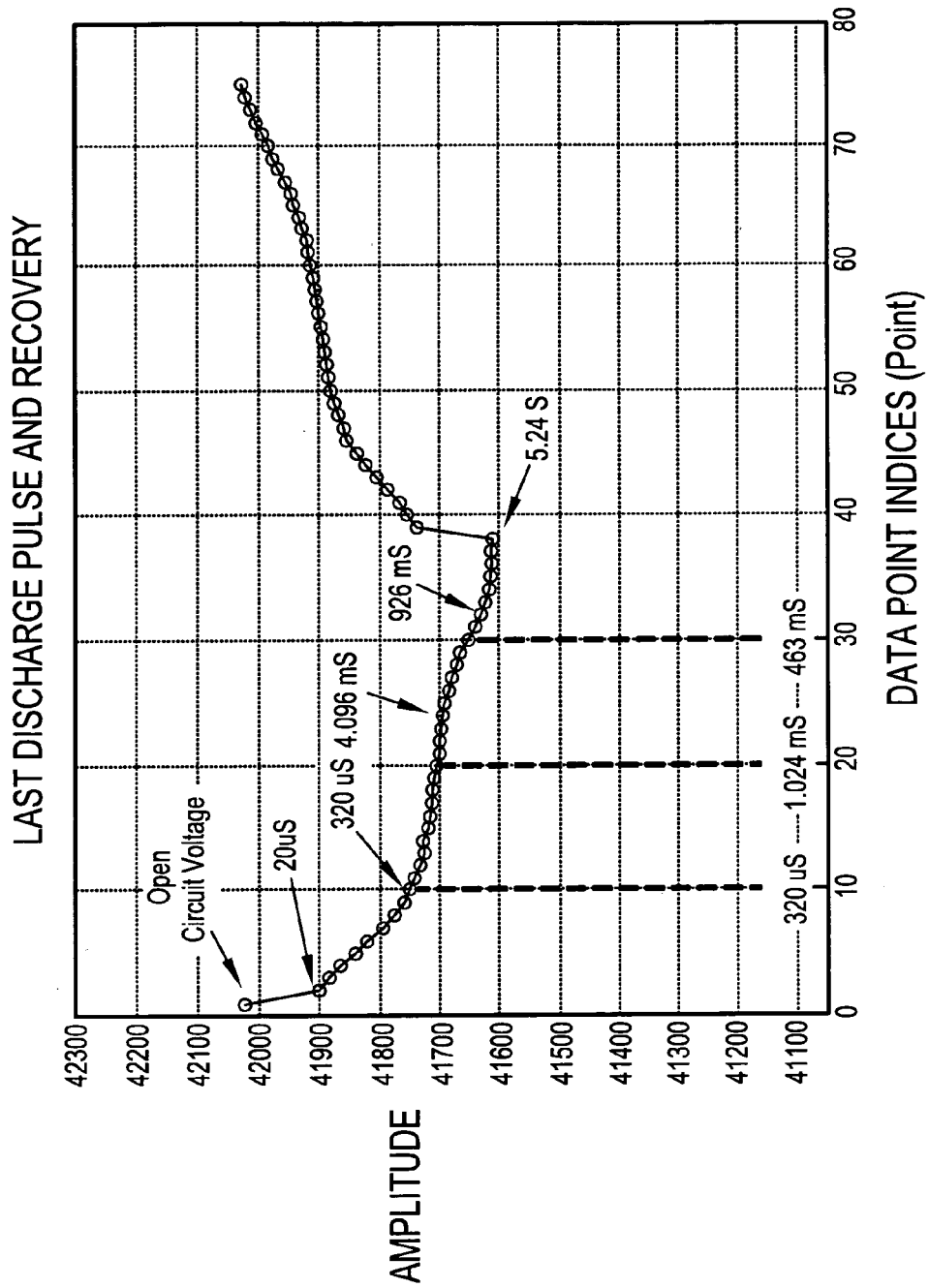
FIG. 18G shows a final waveform plot of an exponentially increasing inter-sample time transformation.

Referring to FIG. 18G, the left-most data point shown (point 1) corresponds to the last sample taken from the previous pulse event, followed by the first sample (point 2) of the current pulse event. The 'y' distance between these points represents the 'step' transition cause by pure Ohmic resistance effects. The last data sample (point 38) of the negative-going wave was acquired 5.24 seconds after the step transition, while its immediate neighbor to the left (point 37) represents a relative Δt of 3.71 seconds. Since the decimation sequence restarts after the 38$^{th}$ point, the elapsed time to its immediate right neighbor (point 39 on this plot) is only 10 microseconds, and the associated 'y' distance between these points represents the next 'step'.

The second important region arises from the initial events that occur within the neighborhood of the electrode-electrolyte interface, encompassing the proximate surface of the electrode, the actual inter-phase region (double-layer), and outward a short distance into the electrolyte solution itself. Provided the physical distance between reactive molecules is small, reactions proceed at high speeds. The distinct shape of the curve in this region (extending to about 320 microseconds) indicate an underlying exponential process exhibiting an 'asymptotic approach characteristic' very similar to a capacitive charging process; this is clearly seen in the raw data of FIG. 18C. While it may appear from the linearly portrayed data of FIG. 18C that this process extends far beyond 320 microseconds, the relatively abrupt change in slope seen in the semi-log FIG. 18F, from about 320 microseconds to 4 milliseconds, indicates instead that this is indeed a distinct region.

The events of the subsequent several milliseconds (320 to 4000 microseconds) are characterized by a tilted but approximately linear portion on the semi-log plot (points 13 to 23 on FIG. 18F), indicating another 'asymptotic exponential data' region (with a substantially longer time constant than region 1). Now, the immediately available reactive components within the interface are running out, giving rise to a chemical potential (concentration gradient) which leads to diffusion of more ions from the bulk electrolyte. Due to diffusion limitations, this interface region (often known as the extended double layer), begins acquiring a charge that is manifest as an increase in polarization voltage.

The fourth and final region of interest begins next (point 28 to 38 on FIG. 18F), exhibiting two distinctly different time constants. The first region spans less than one second and the second region takes tens of seconds (the latter process appears more clearly in data from a 30 minute discharge test. The 'dip' near the end of FIG. 19—in pulse-type testing, however, the excitation changes polarity before this time constant expires). In this region, a short, fast curved section is followed by another flat segment that signals the establishment of an interim diffusion gradient (a dynamic equilibrium) extending from the proximate electrode surface out into the ionic reservoir of the bulk electrolyte.

Figure 19:
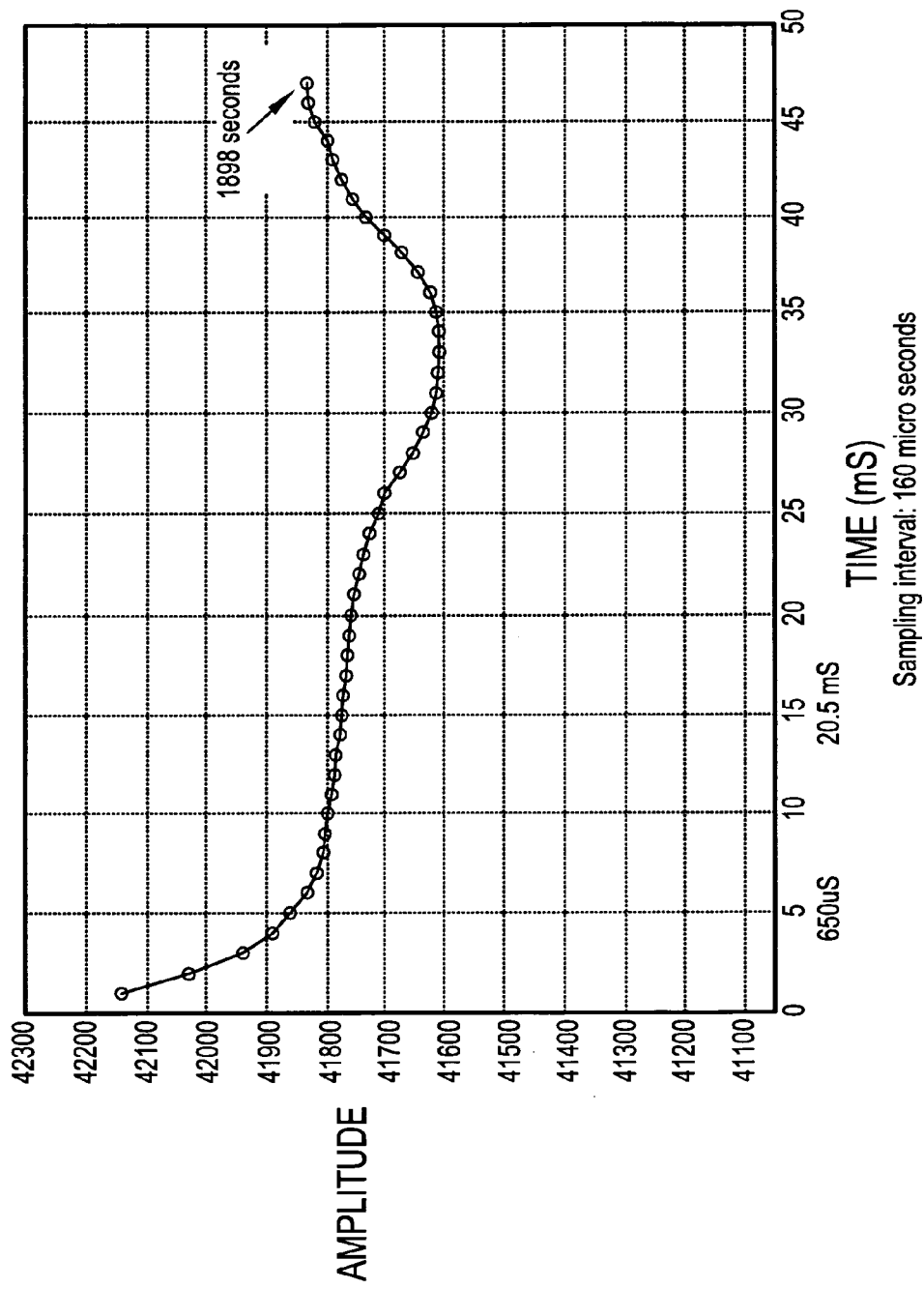
FIG. 19 shows a data plot of discharge test protocol.

It should be noted that in extended constant current discharge tests (see FIG. 19), another effect becomes manifest. In the fourth region, a plateau region is apparent, where the cell voltage appears stabilized. Within about 20 seconds, however, the cell's voltage begins its final slow climb (to several millivolts above the fourth region identified earlier) to a steady state value (fifth region) that is, for a healthy cell, load current dependant. Until the cell is nearing end of life, the value finally attained in the fifth region is relatively flat. This final sustaining voltage is typically achieved well along into discharge. Since only a 30-minute discharge test protocol is shown in FIG. 19, the fourth region stands out clearly, but only the approach to the fifth region is apparent. In much longer tests, at a discharge rate of 400 milliamps, this final plateau is reached after nearly an hour.

Discussion of Individual Test Protocol Data and Analysis Techniques

A brand new 7.5 amp-hour lithium sulfur dioxide cylindrical cell was subjected to a series of equal duration discharge events (400 ma for 2 hours), at 24-hour intervals. The standard test protocol (0.762 Hz, 50% duty cycle, 1 amp peak, for 255 consecutive cycles) was employed, and the cell was tested immediately prior to each discharge event.

FIG. 16A shows the exponentially decimated data (all 255 discharge/rest cycles) from the first test protocol. Since there are 29 data points in each pulse period (a pulse period is equivalent to one half cycle of the 50% duty cycle excitation waveform), individual points cannot be easily resolved in the plot. Several important features of the cell's behavior are immediately apparent, and are more clearly visible in FIG. 16B, which provides the amplitude envelope signature of the cell. Here the extrema points of the amplitude envelope appear individually, without interconnecting lines. Recall that, while the data points within each pulse event are exponentially decimated, the overall plot appears linearly rendered with respect to time, such that each complete discharge/rest cycle has the same width (duration) in the plot. Thus, the overall variations and trends seen in the envelope plot reflect their true temporal evolution.

Figure 20A:
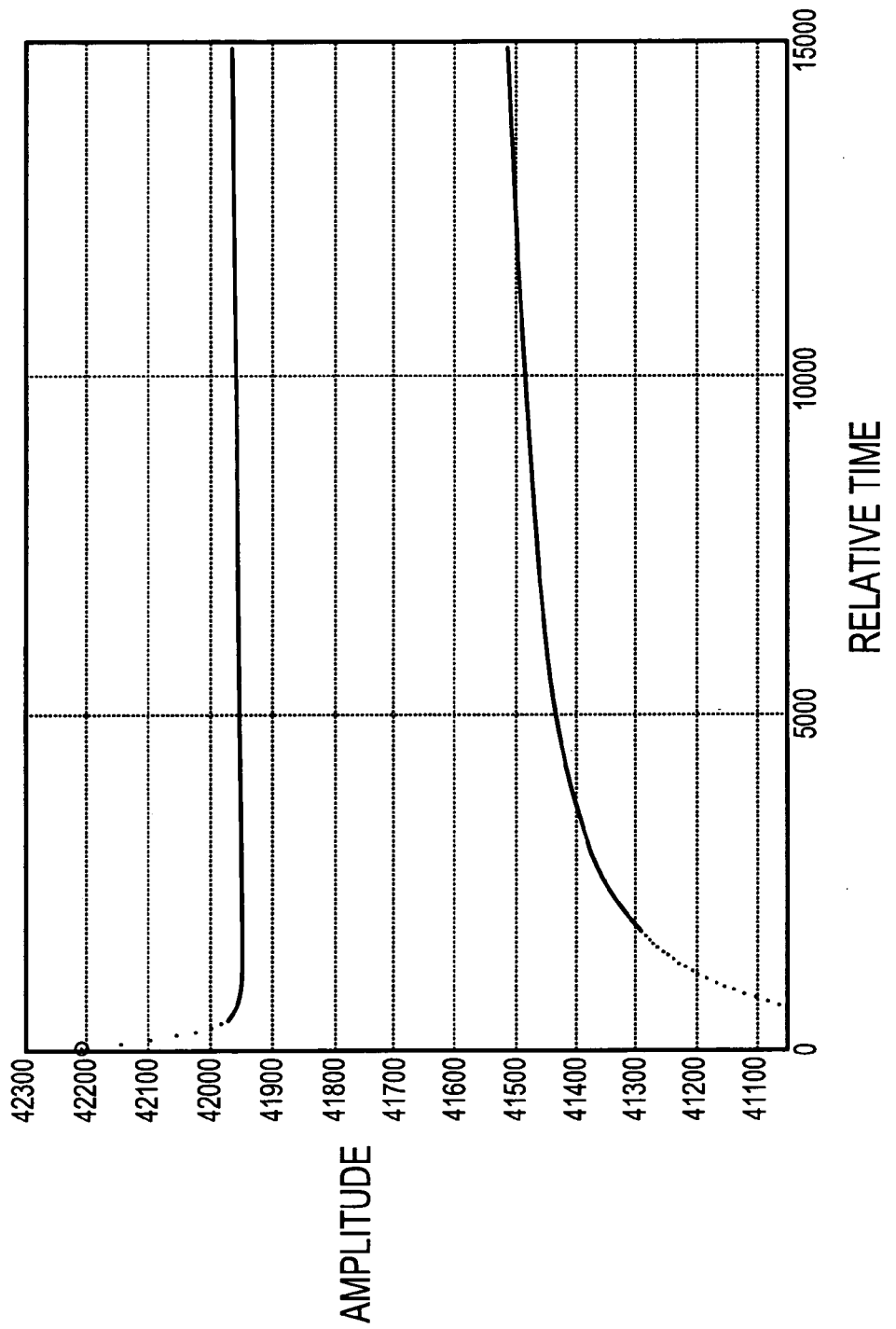
FIGS. 20A–20C show data plots 24 hours after a final discharge event.
Figure 20B:
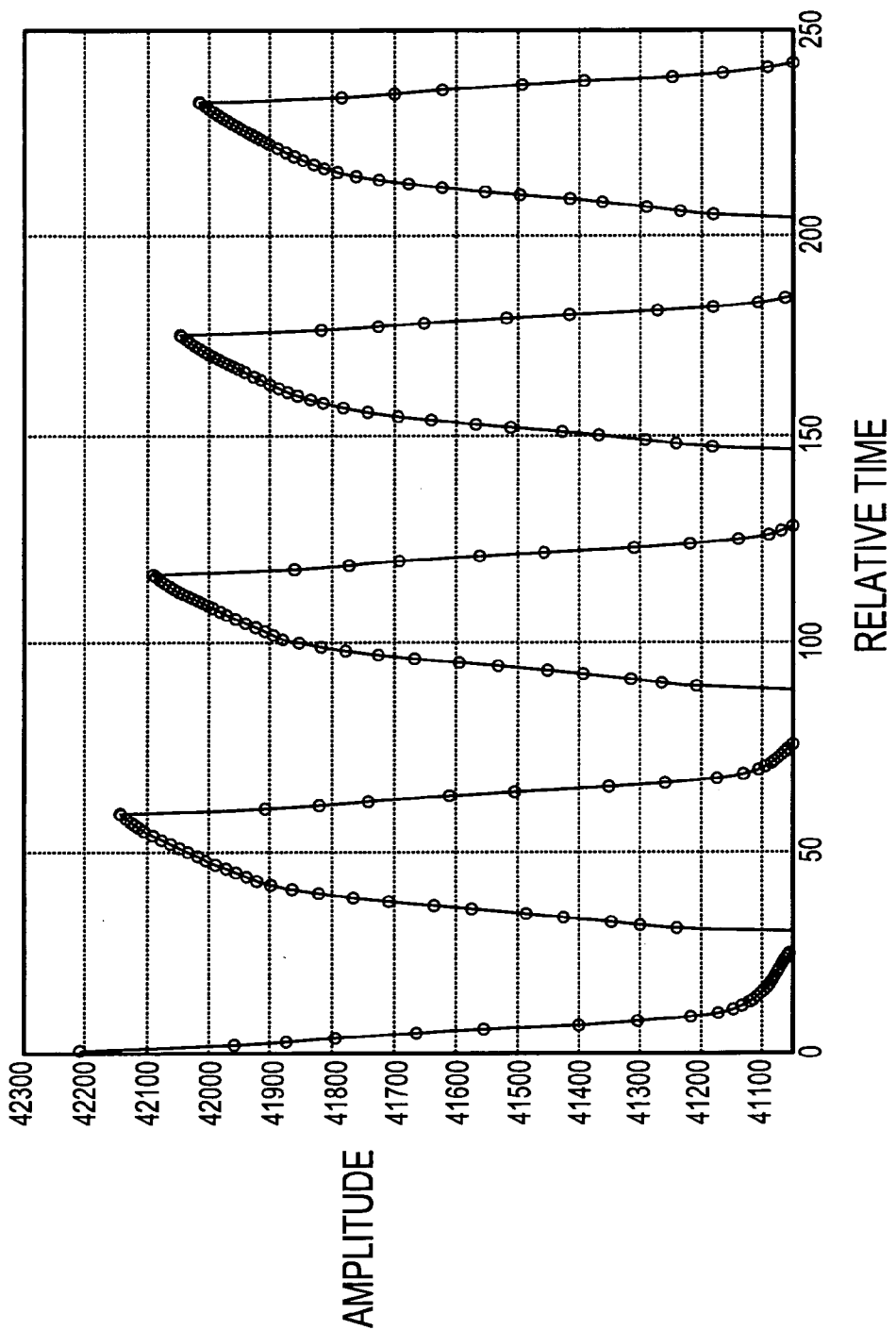
Figure 20C:
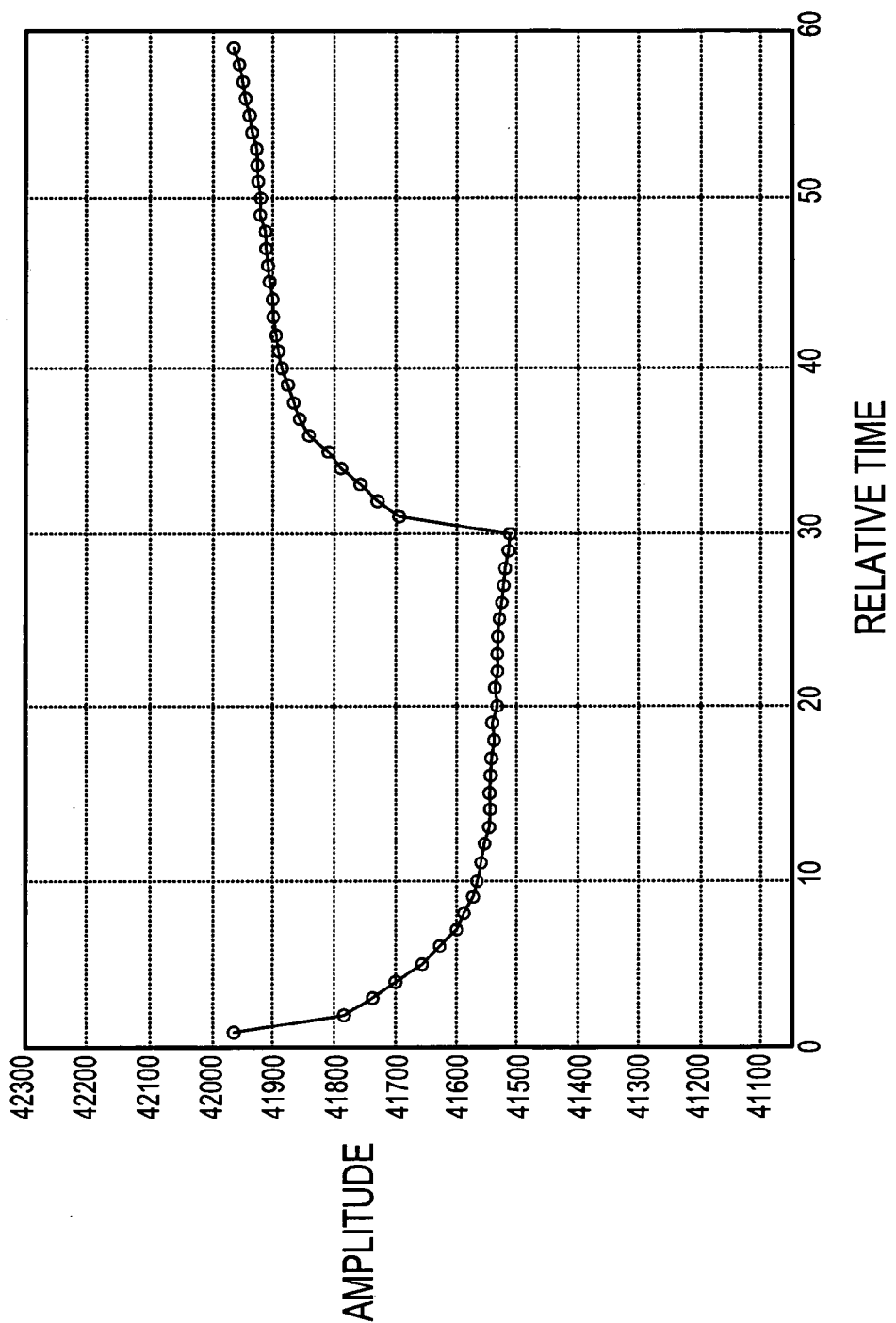
Figure 21A:
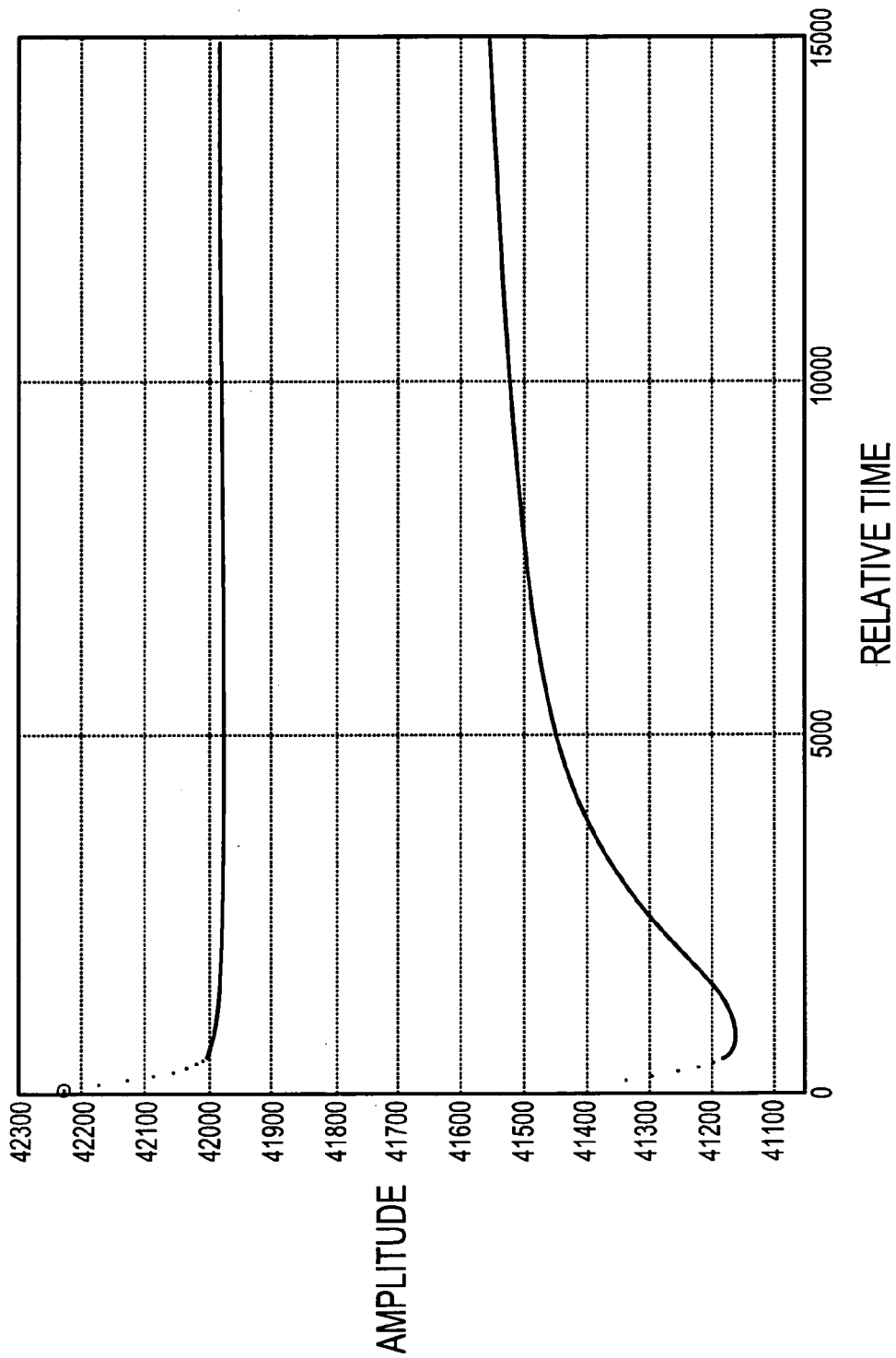
FIGS. 21A–27C show data plots.
Figure 21B:
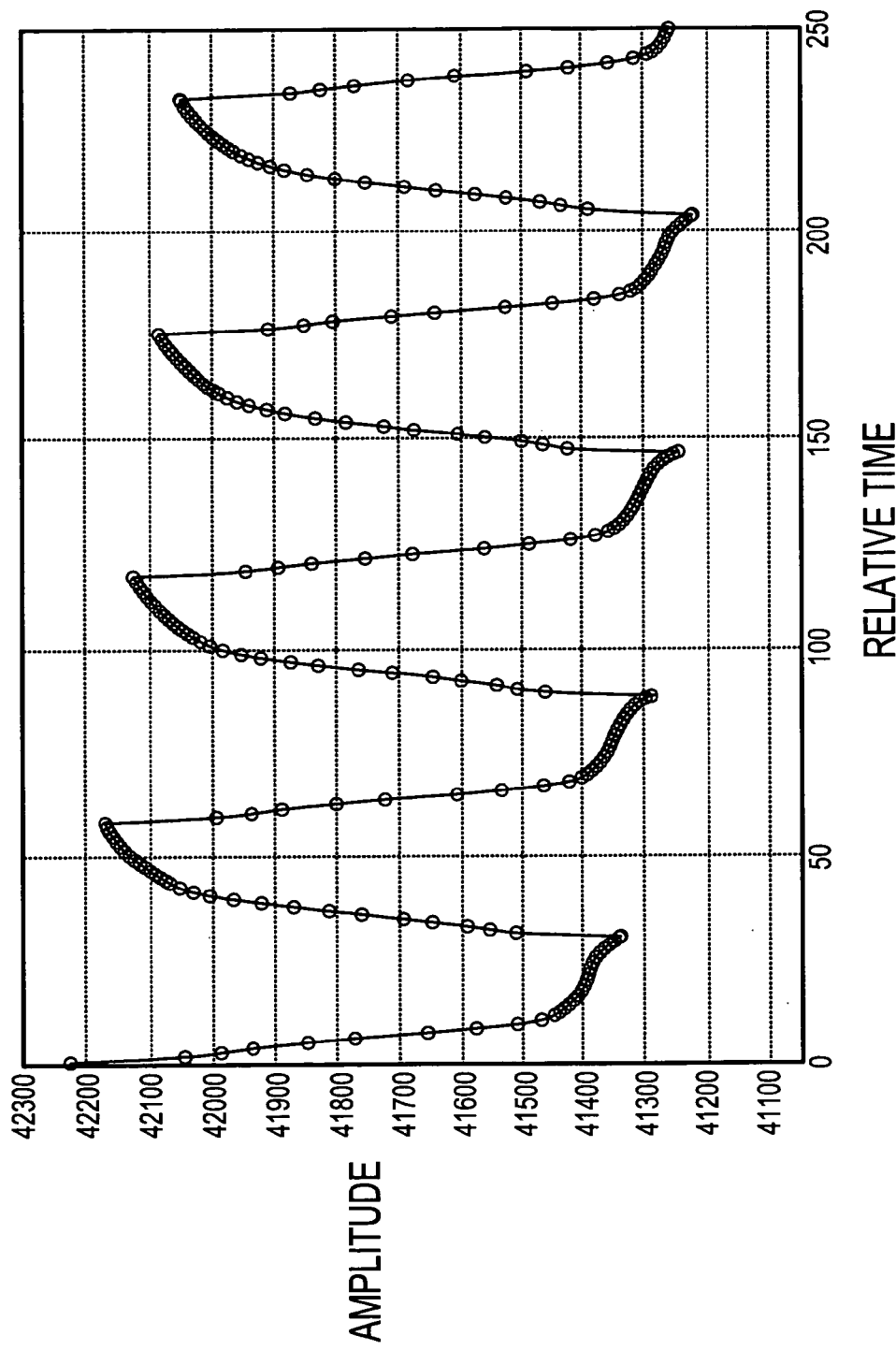
Figure 21C:
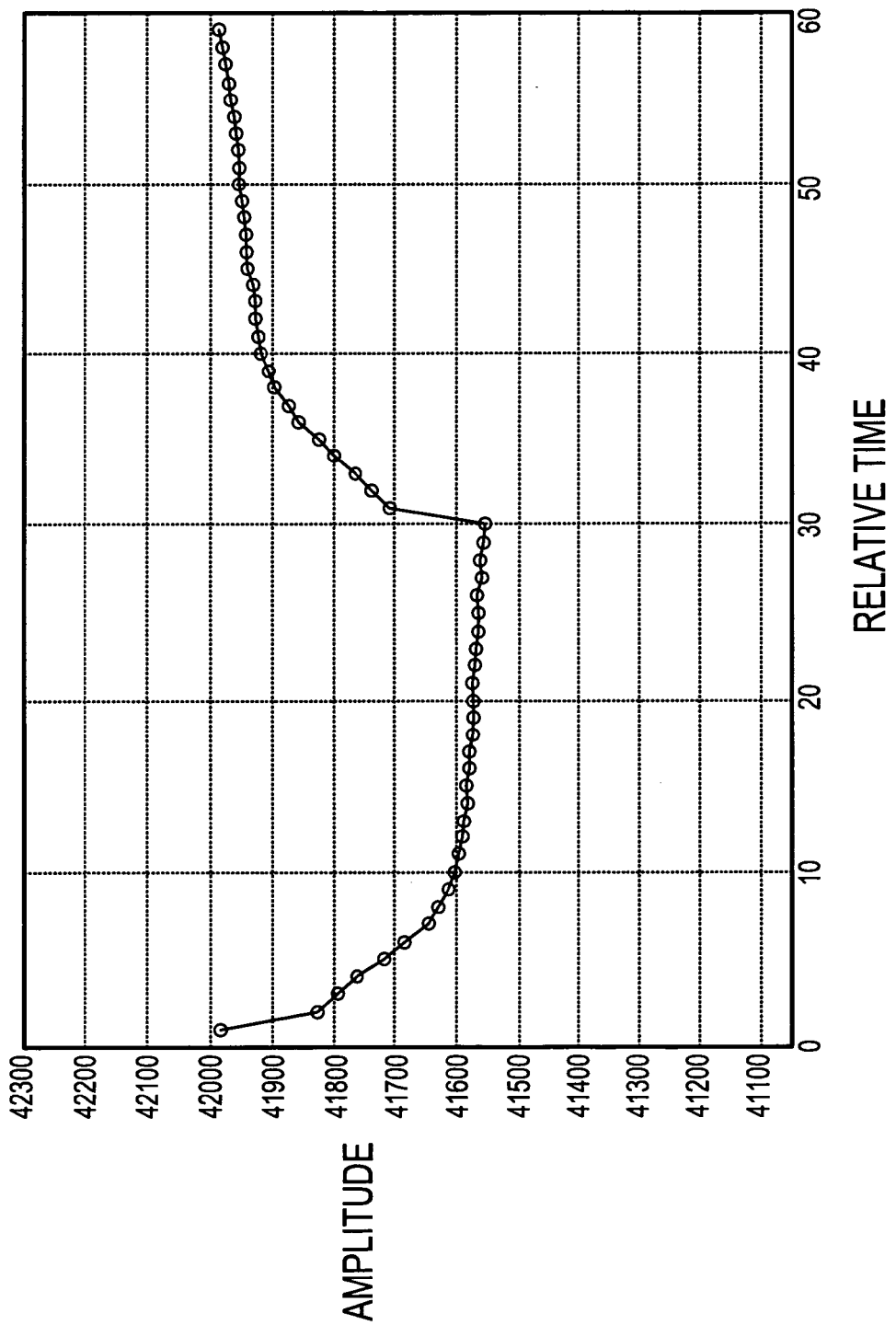
Figure 22A:
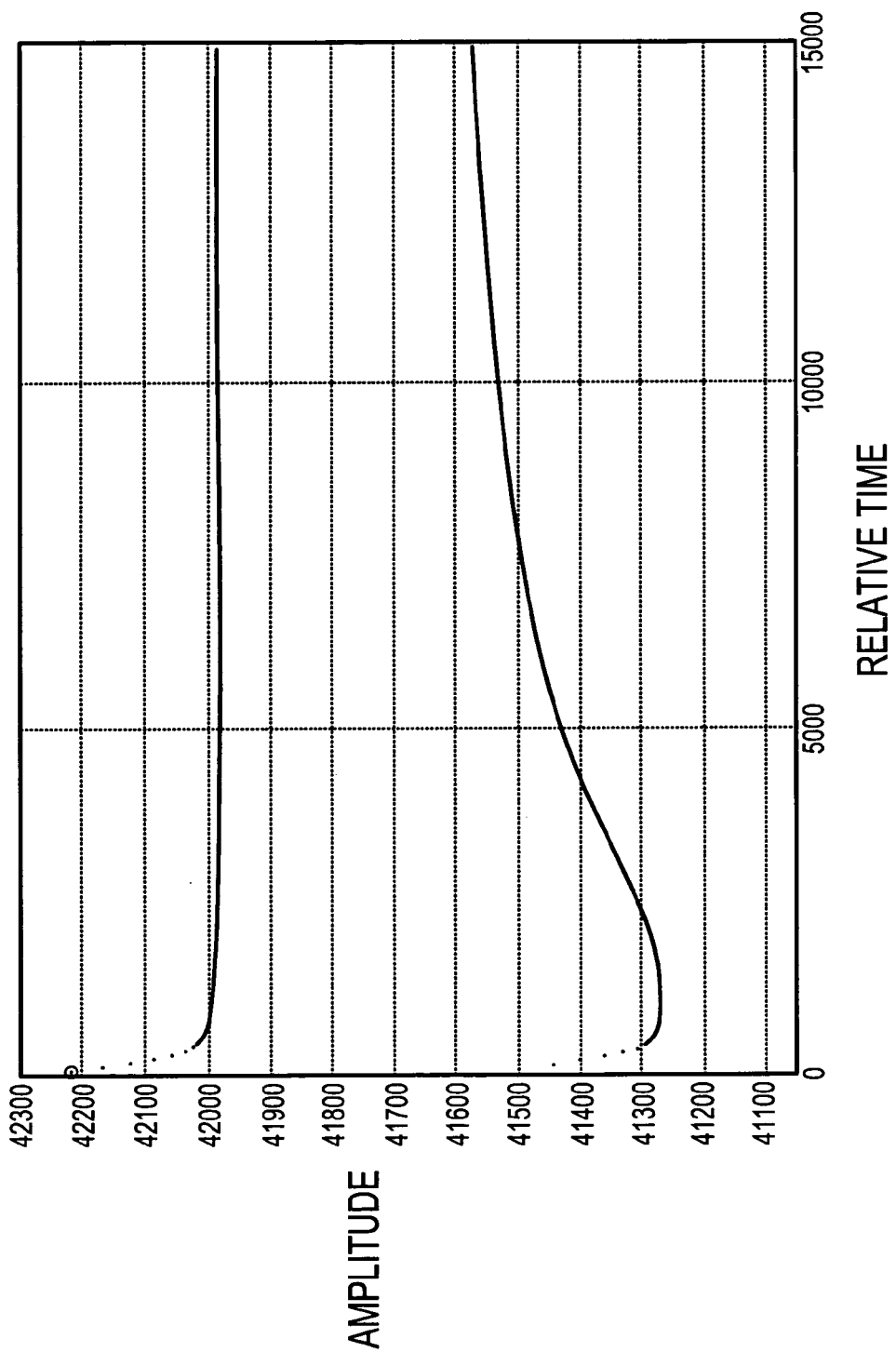
Figure 22B:
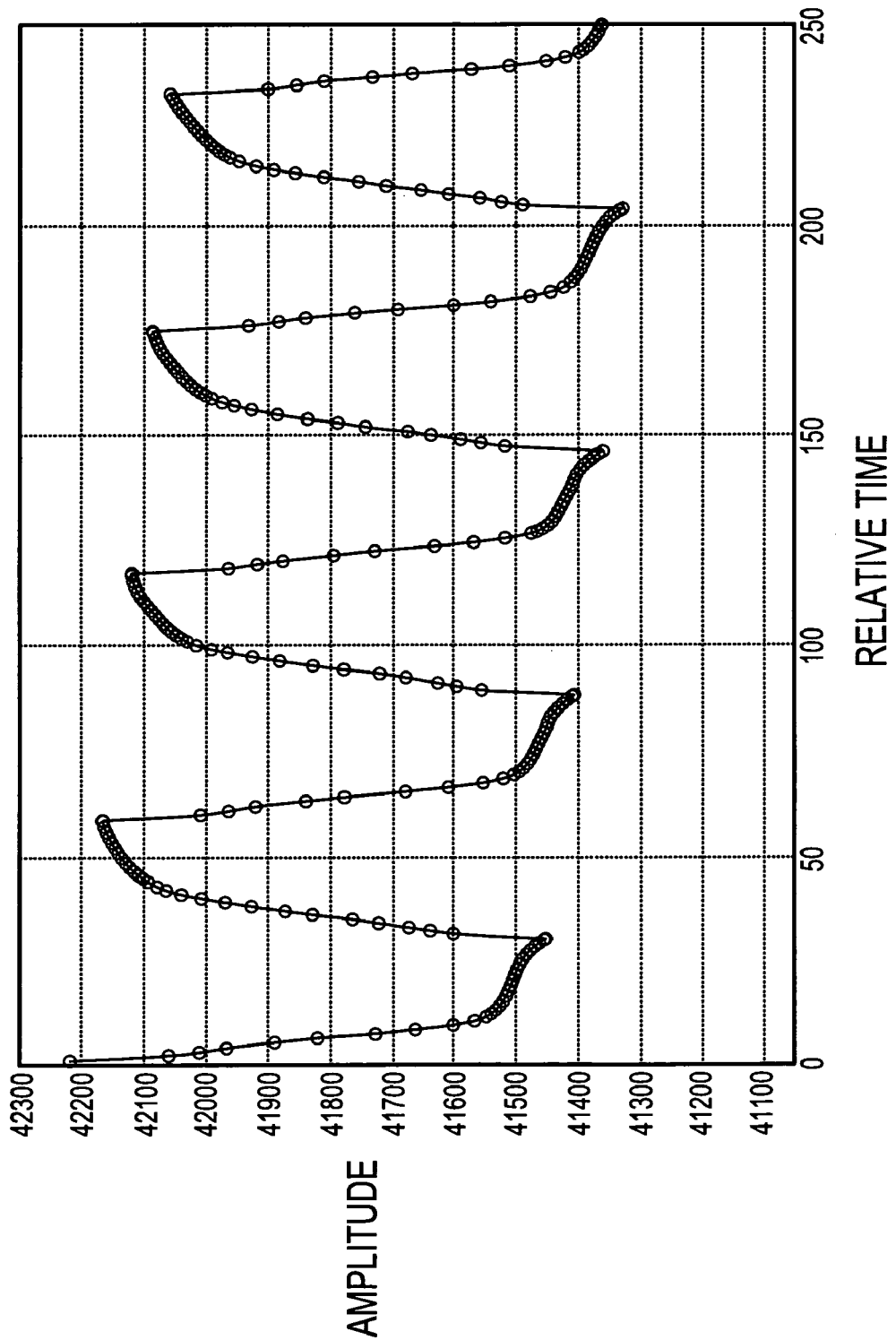
Figure 22C:
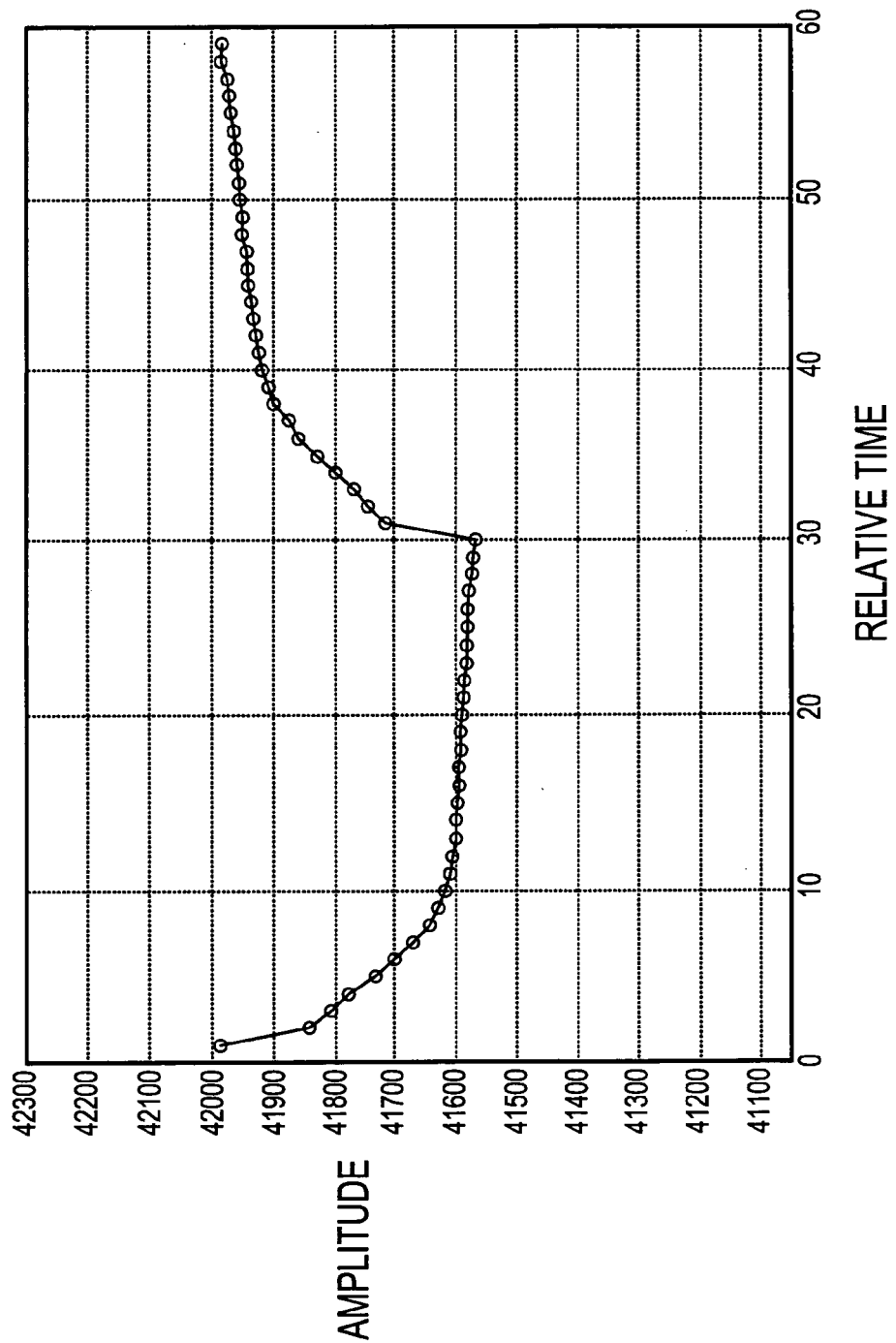
Figure 23A:
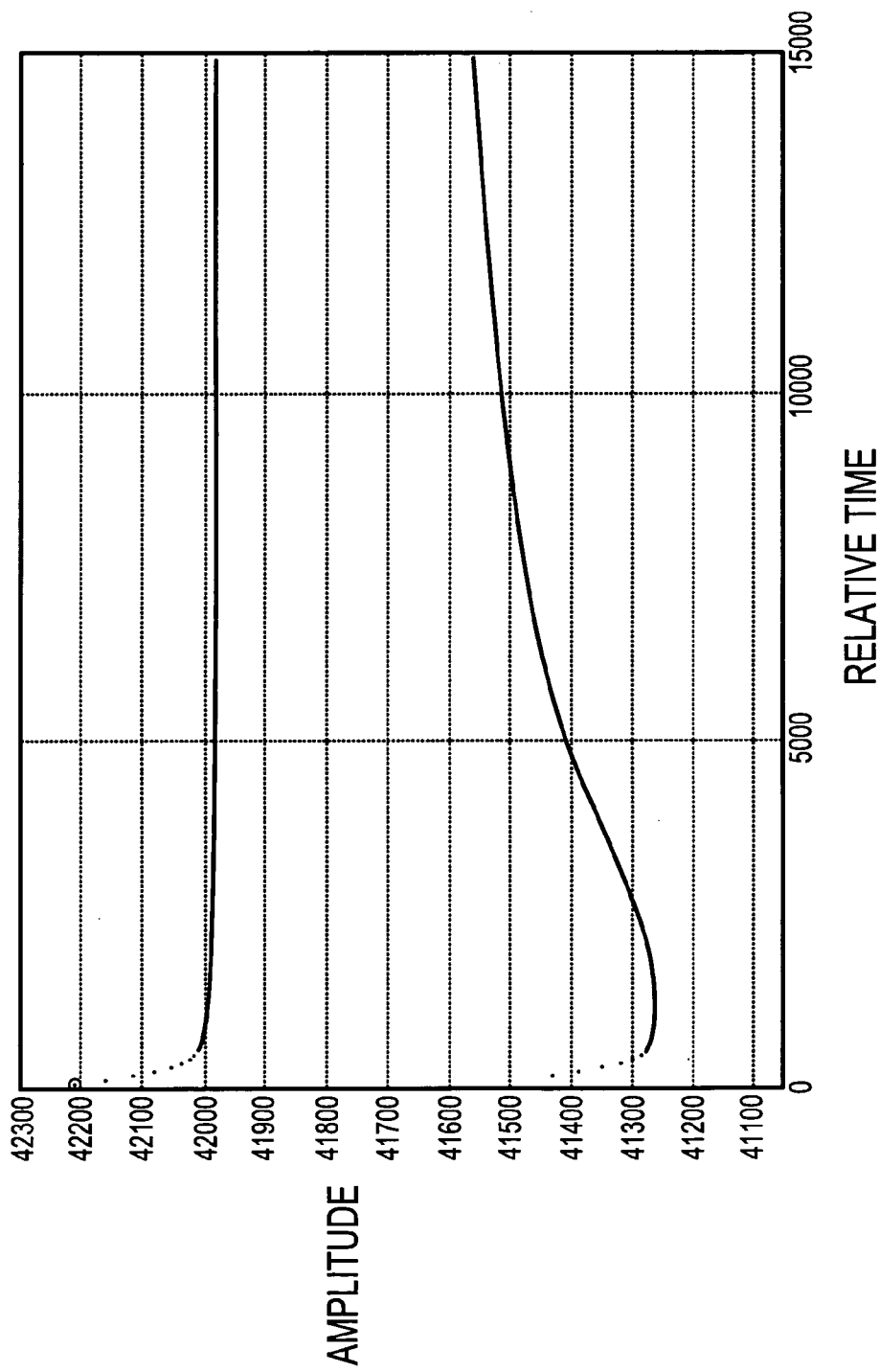
Figure 23B:
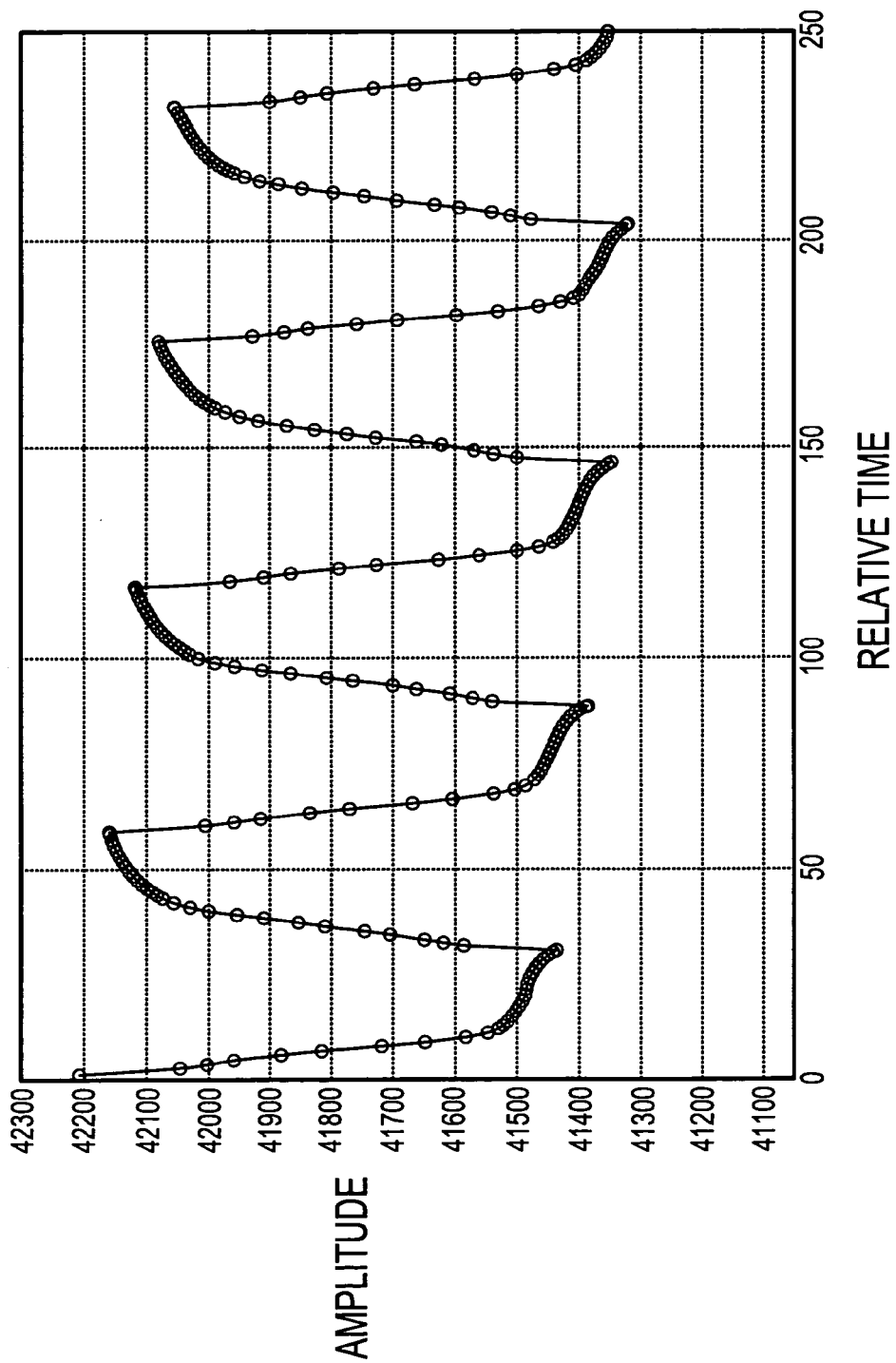
Figure 23C:
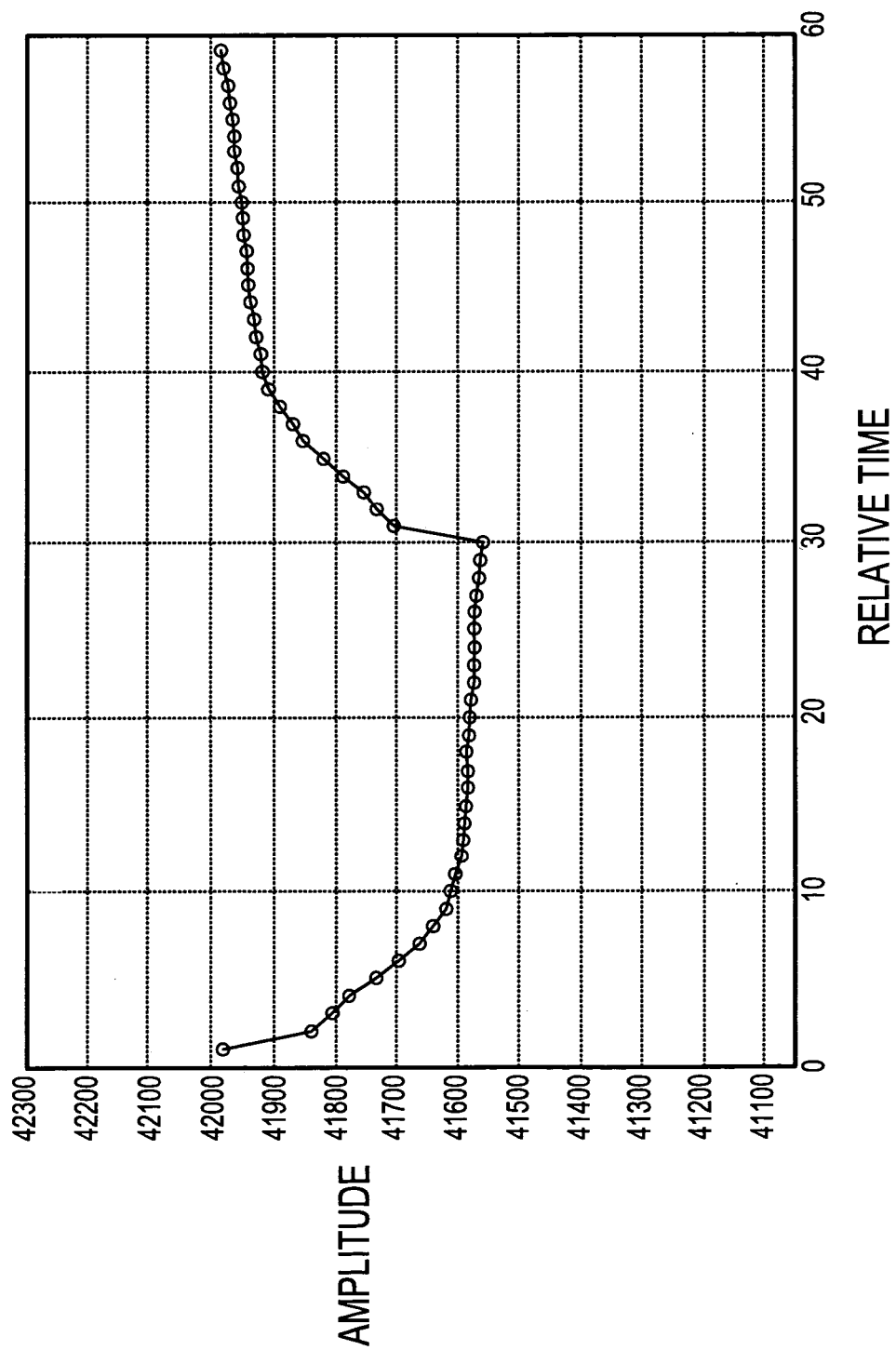
Figure 24A:
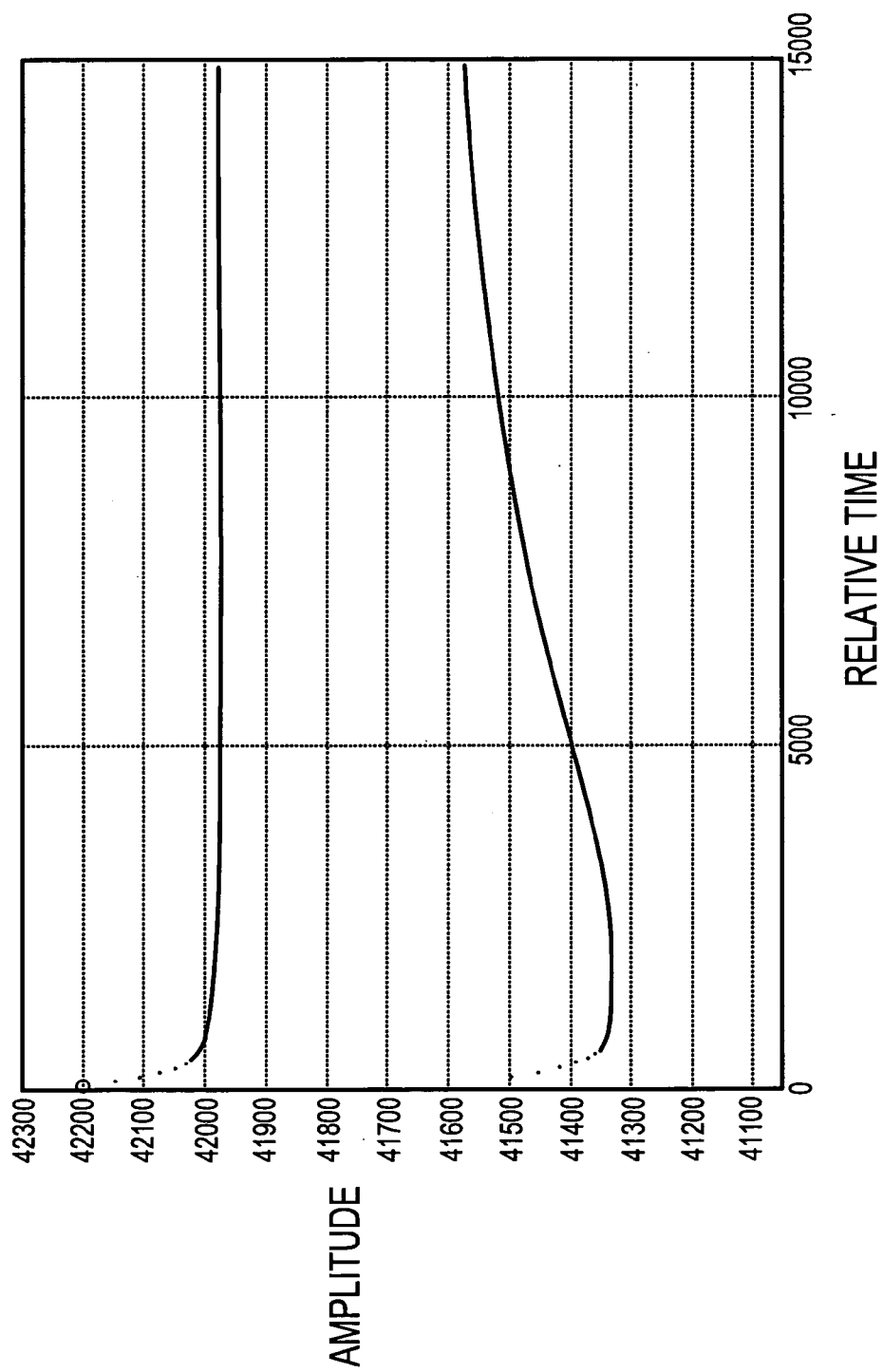
Figure 24B:
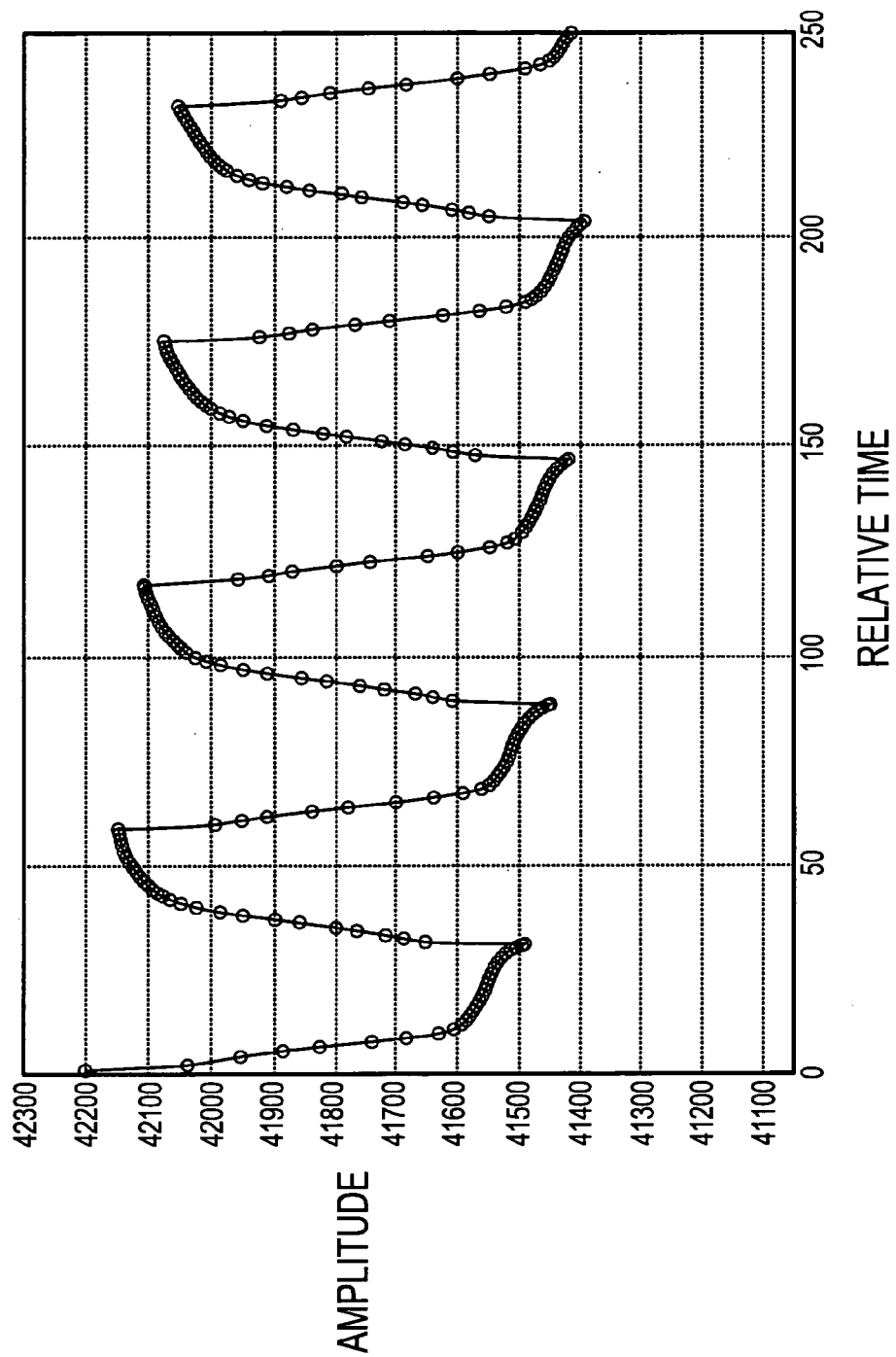
Figure 24C:
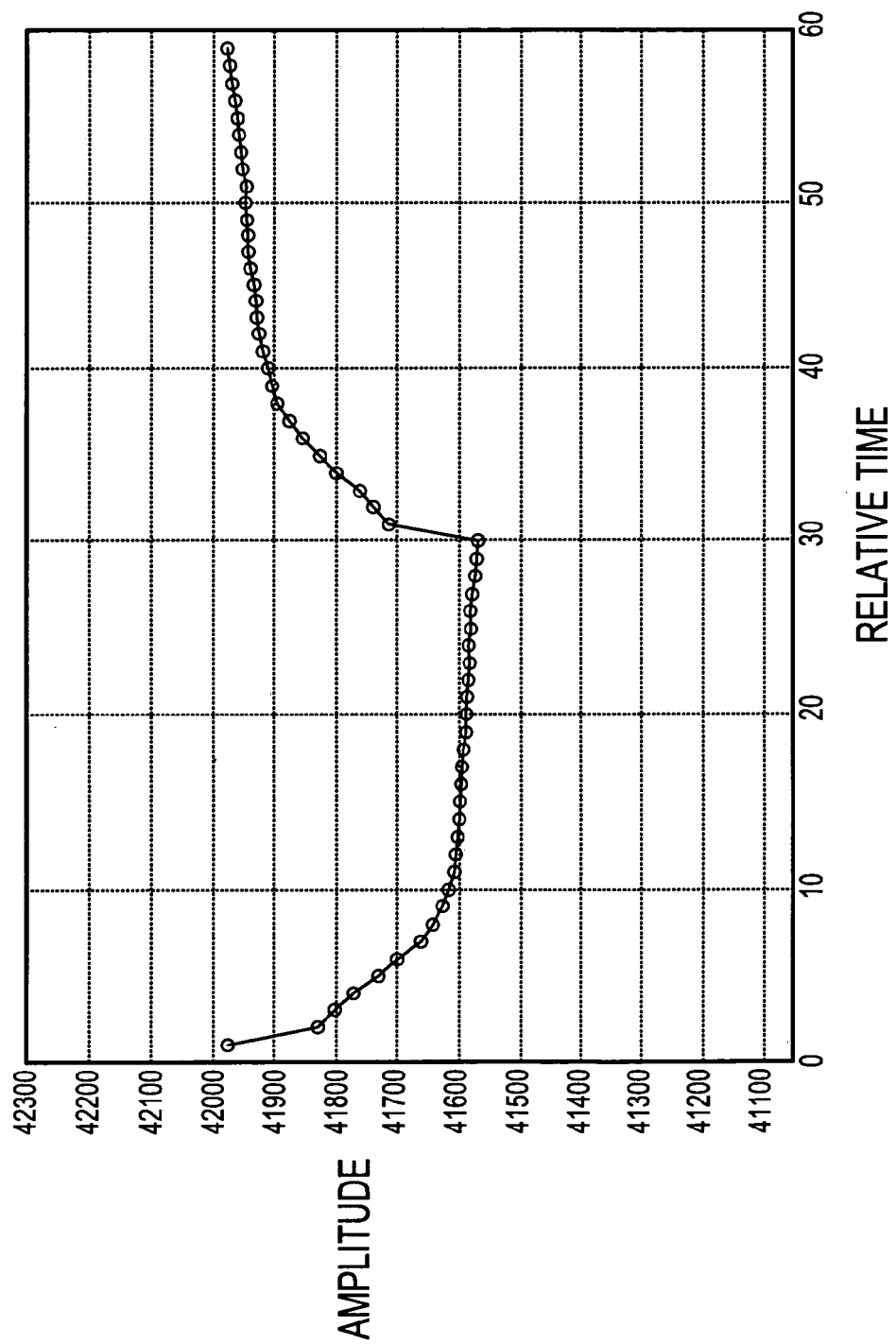
Figure 25A:
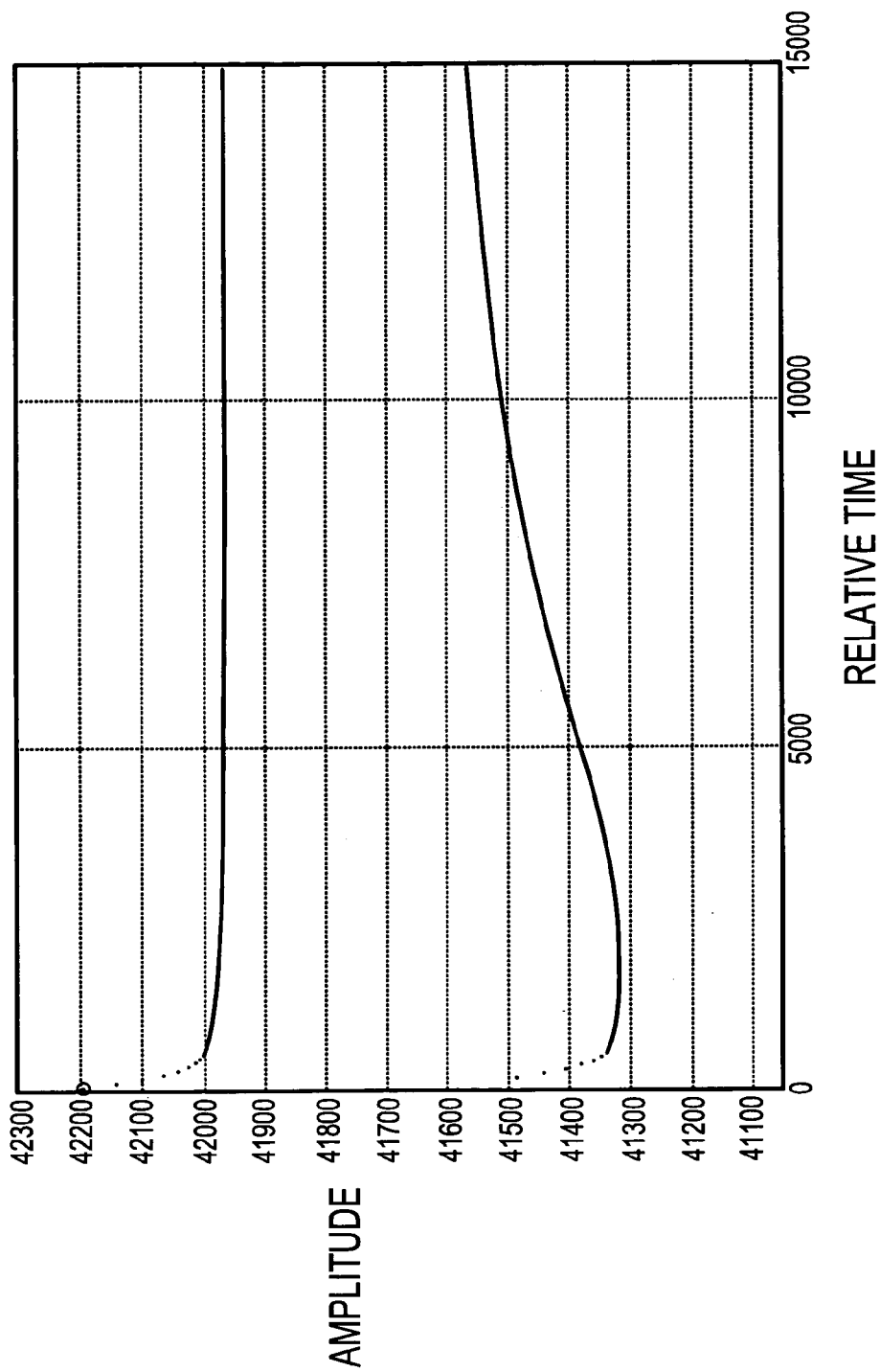
Figure 25B:
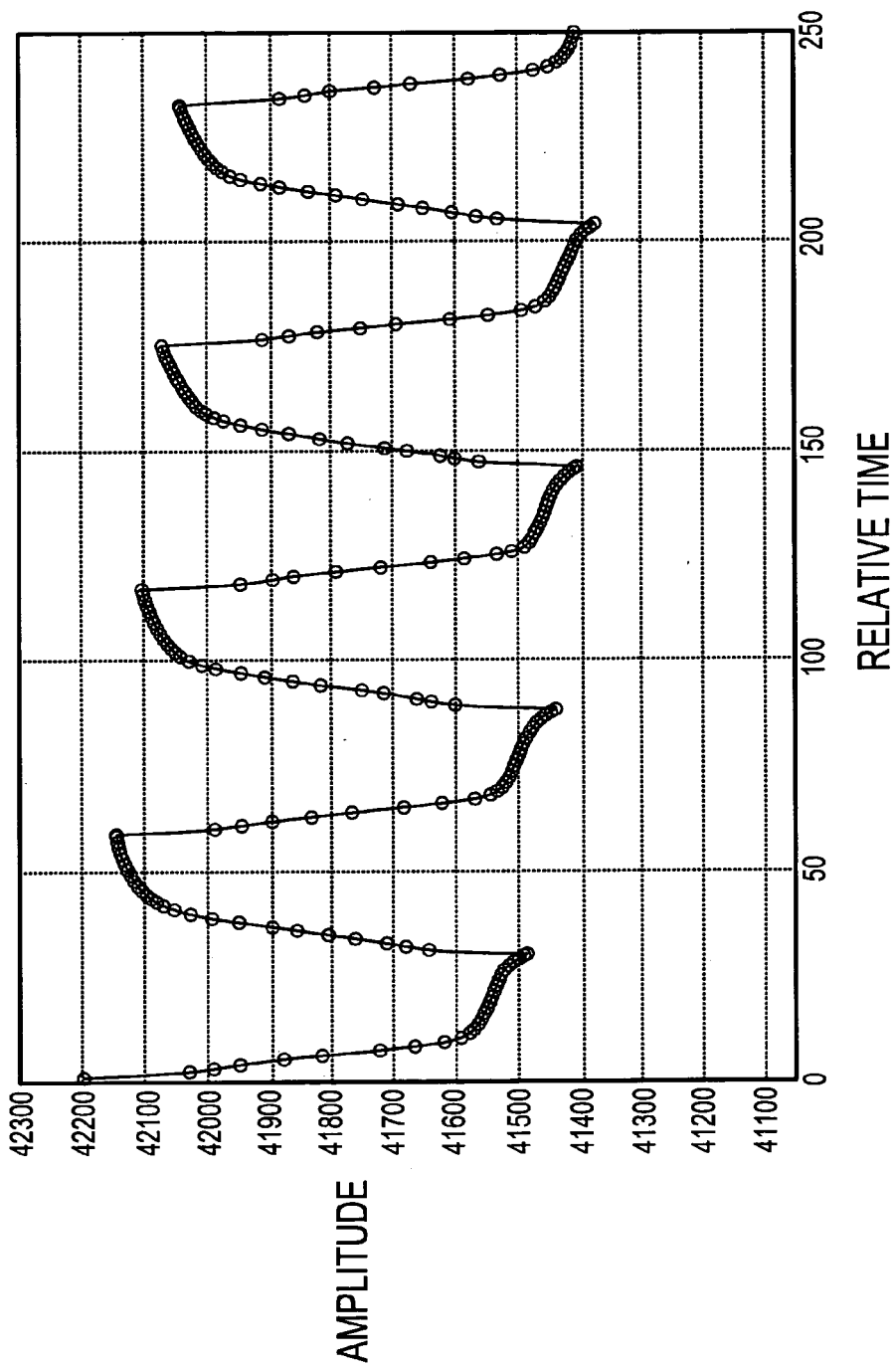
Figure 25C:
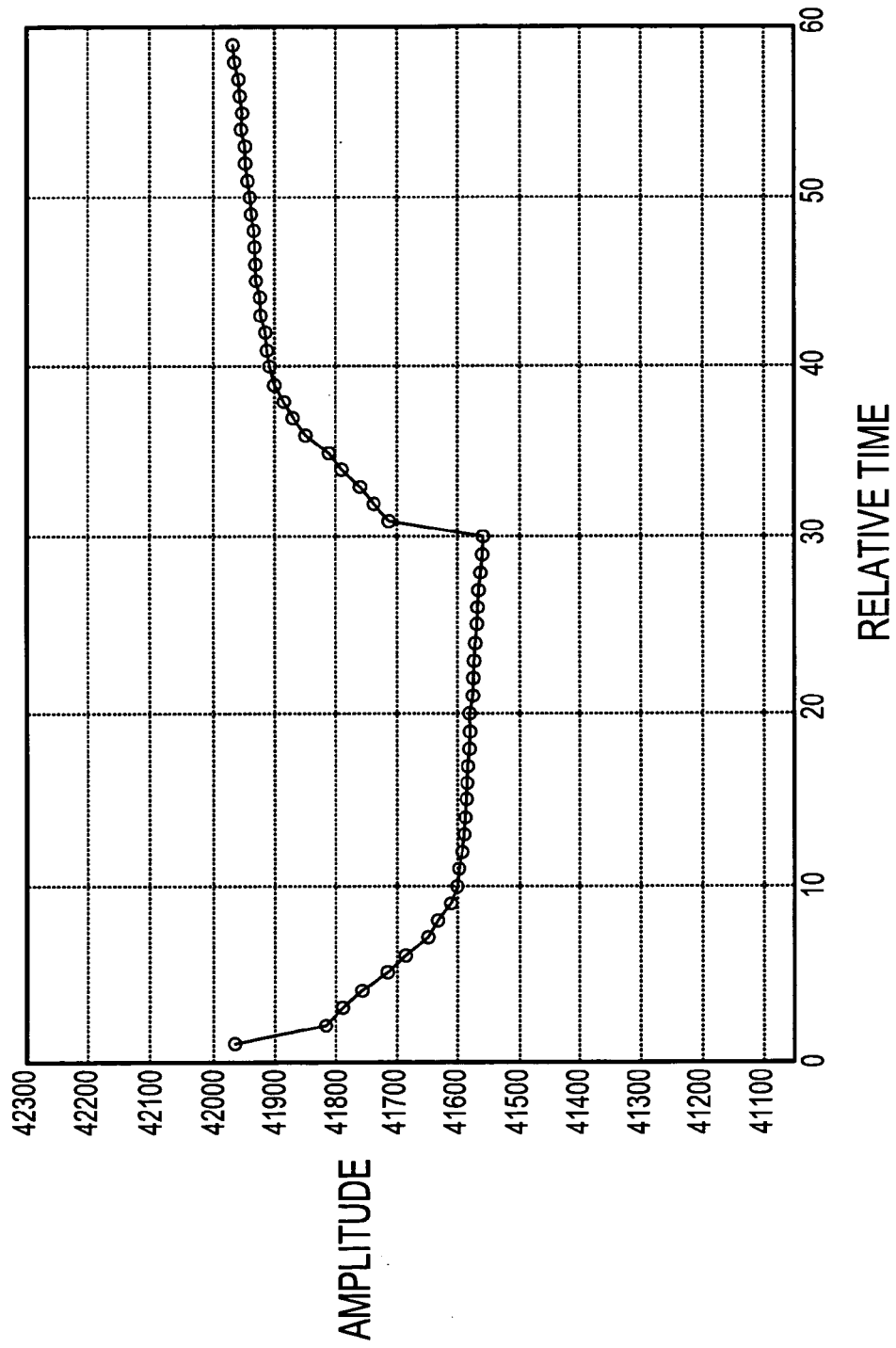
Figure 26A:
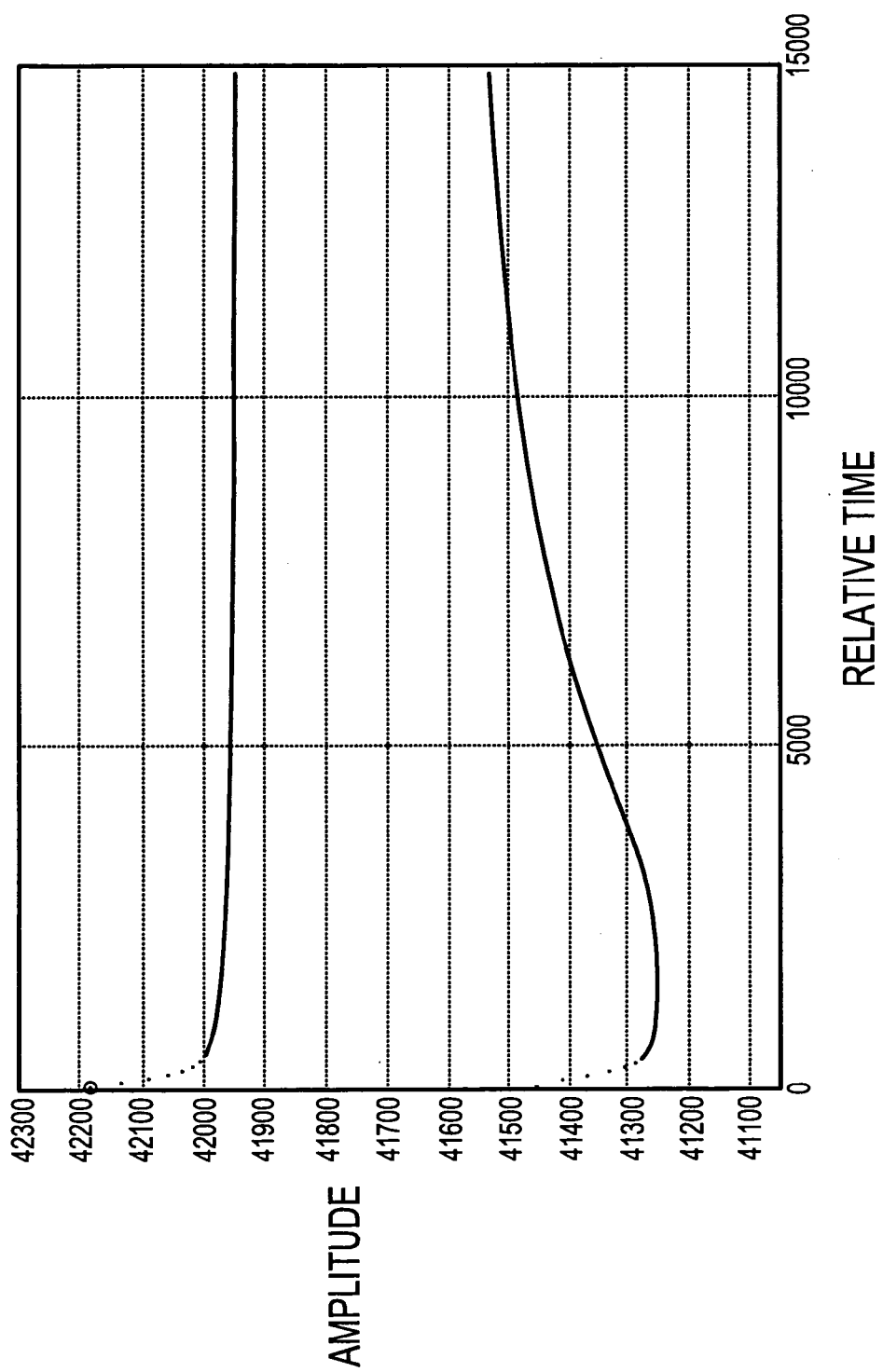
Figure 26B:
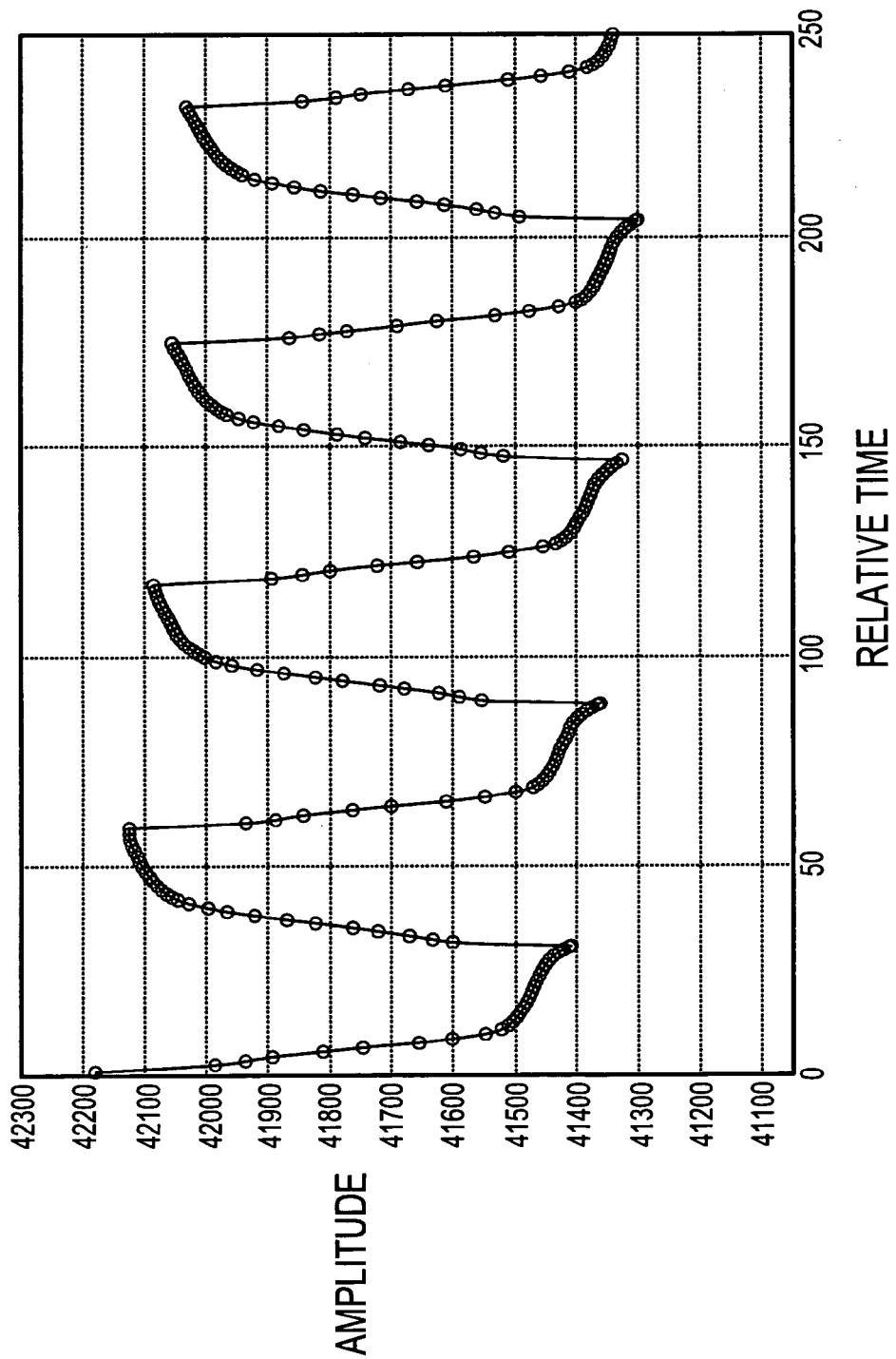
Figure 26C:
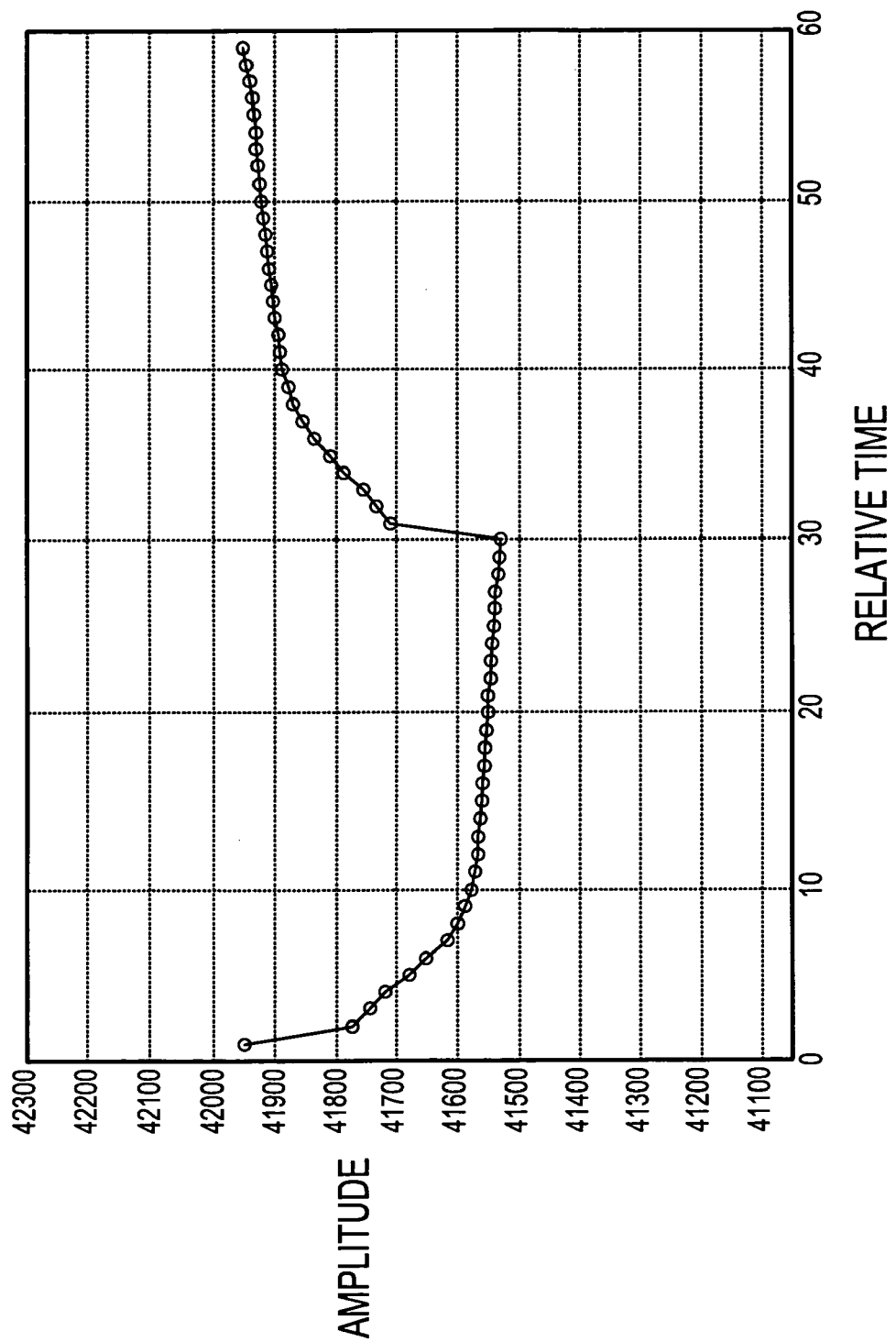
Figure 27A:
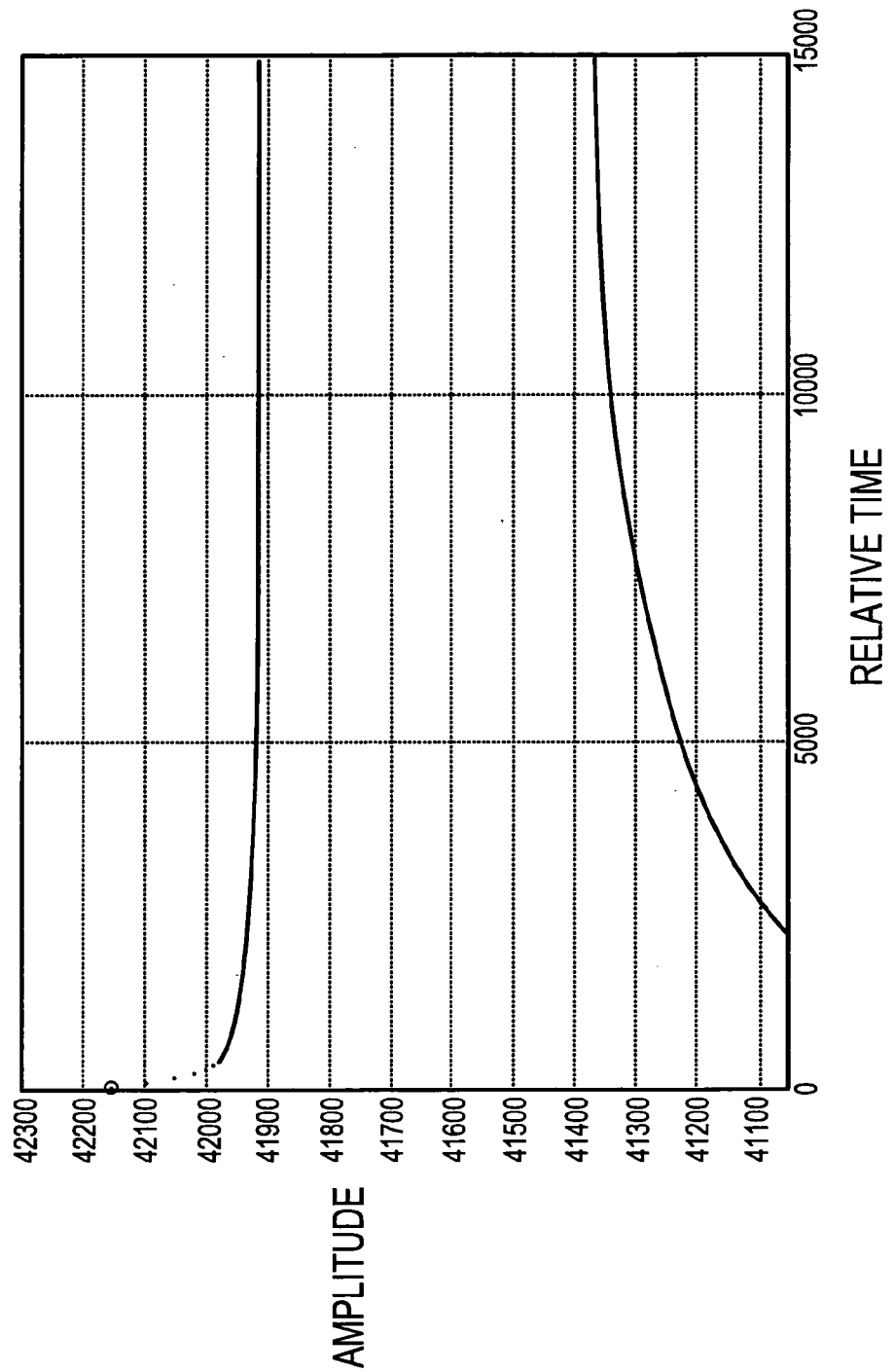
Figure 27B:
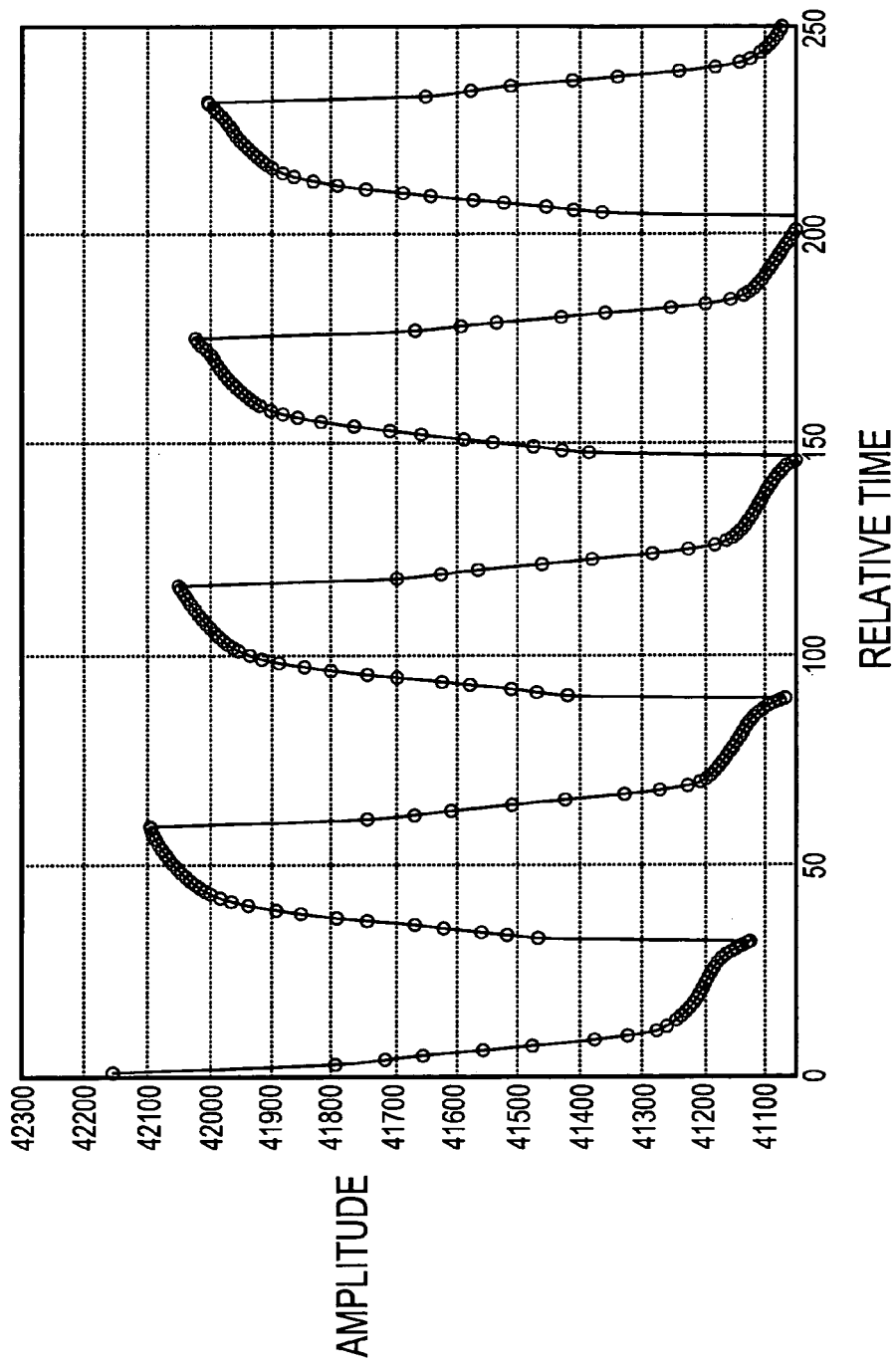
Figure 27C:
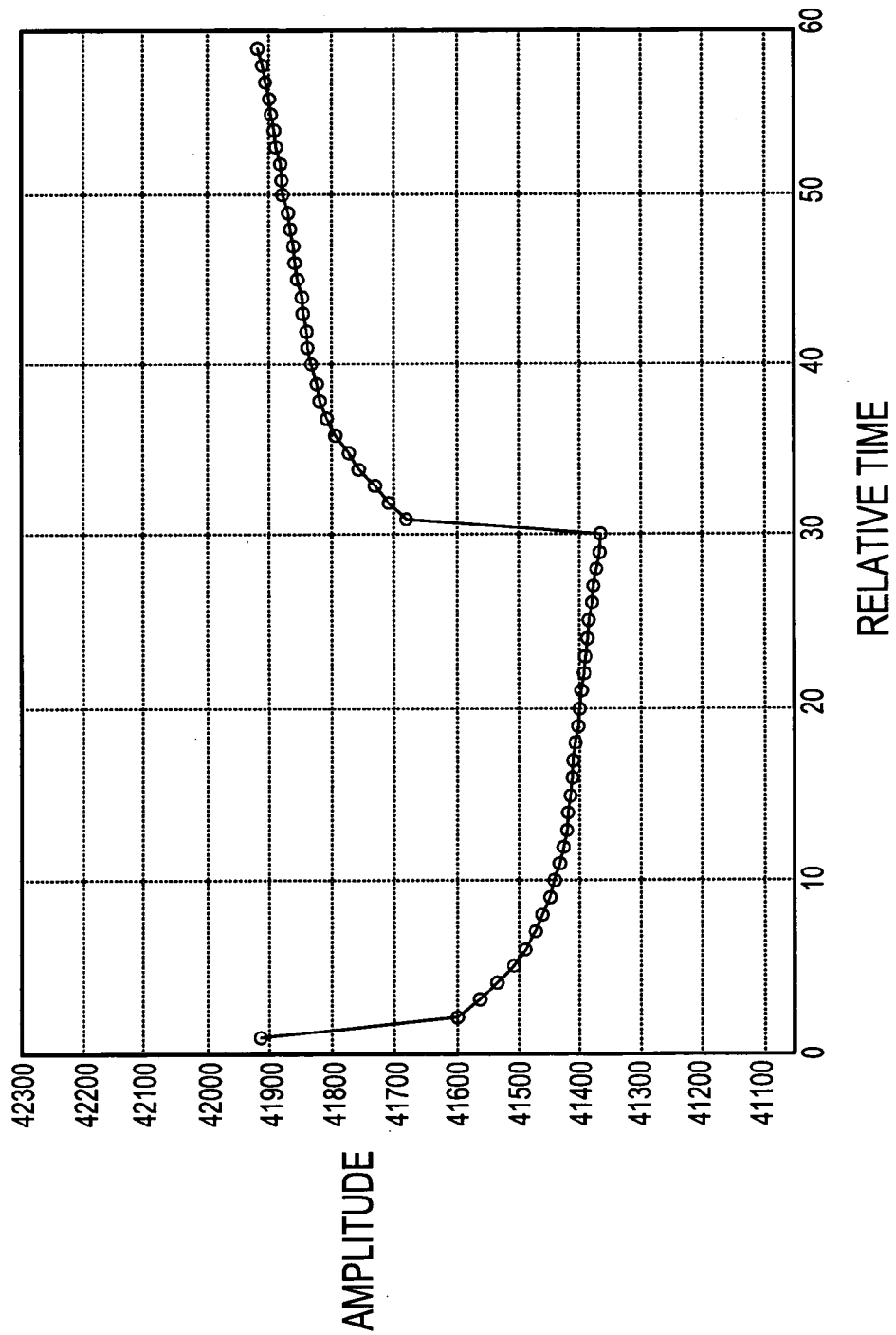

The cell was subjected to eight successive 2-hour, 400 milliampere discharges; by the end of the last discharge, the terminal voltage of the cell had fallen to 2.499 volts, indicating approaching 'end of life'. FIGS. 20A–20C through FIGS. 27A—27C provide the details of the tests, each performed immediately prior to the upcoming discharge (and so, 24 hours after the preceding discharge event). FIGS. 20A–20C provide data 24 hours after the final discharge event. This sequence of 'test followed by discharge' ensures that the data is representative of the cell's state of charge before the associated discharge event, allowing quantitative, predictive relationships to be determined.

Referring to FIG. 20A, the very first two data points (a circle for the positive envelope, a dot for the negative) are coincident, and correspond to the open circuit voltage of the cell before the onset of the excitation. As soon as the excitation commences, the 'loaded' voltage of the cell (the lower extrema envelope curve in the plot) drops off precipitously, while the 'recovery' voltage of the cell (the upper extreme envelope curve in the plot) quickly assumes a constant value. After a short while, the negative slope of the lower envelope reverses, as the 'loaded' cell voltage begins to recover. This effect is well known from standard discharge test profiles, but it is interesting that it also appears so clearly under the present pulsed discharge/rest paradigm. What is unexpected is that the slope displayed by the upper side of the envelope is virtually constant for most of the test, irrespective of the changes at the lower margin. The reason for this is that the upper curve represents the 'recovered' condition of the cell, in the absence of discharge current, whereas the shape bottom curve indicates the evolution of a new, stable dynamic equilibrium in response to the current. As will be explained below, it is the relationship between these two curves during each test, and especially their overall shape in comparison to previously established baseline data that allows accurate estimation of the cell's state of charge.

Because the $LiSO_2$ cell maintains a nearly constant open circuit terminal voltage over most of its operating life, OCV alone is not suitable as a direct indication of state of charge. However, when such cells are tested according to the disclosed method, the specific shape and amplitude of the resulting amplitude envelope signature curve reveals trends that are directly and monotonically correlated with state of charge. Both the upper and lower extreme envelopes change as a function of state of charge.

Figure 28A:
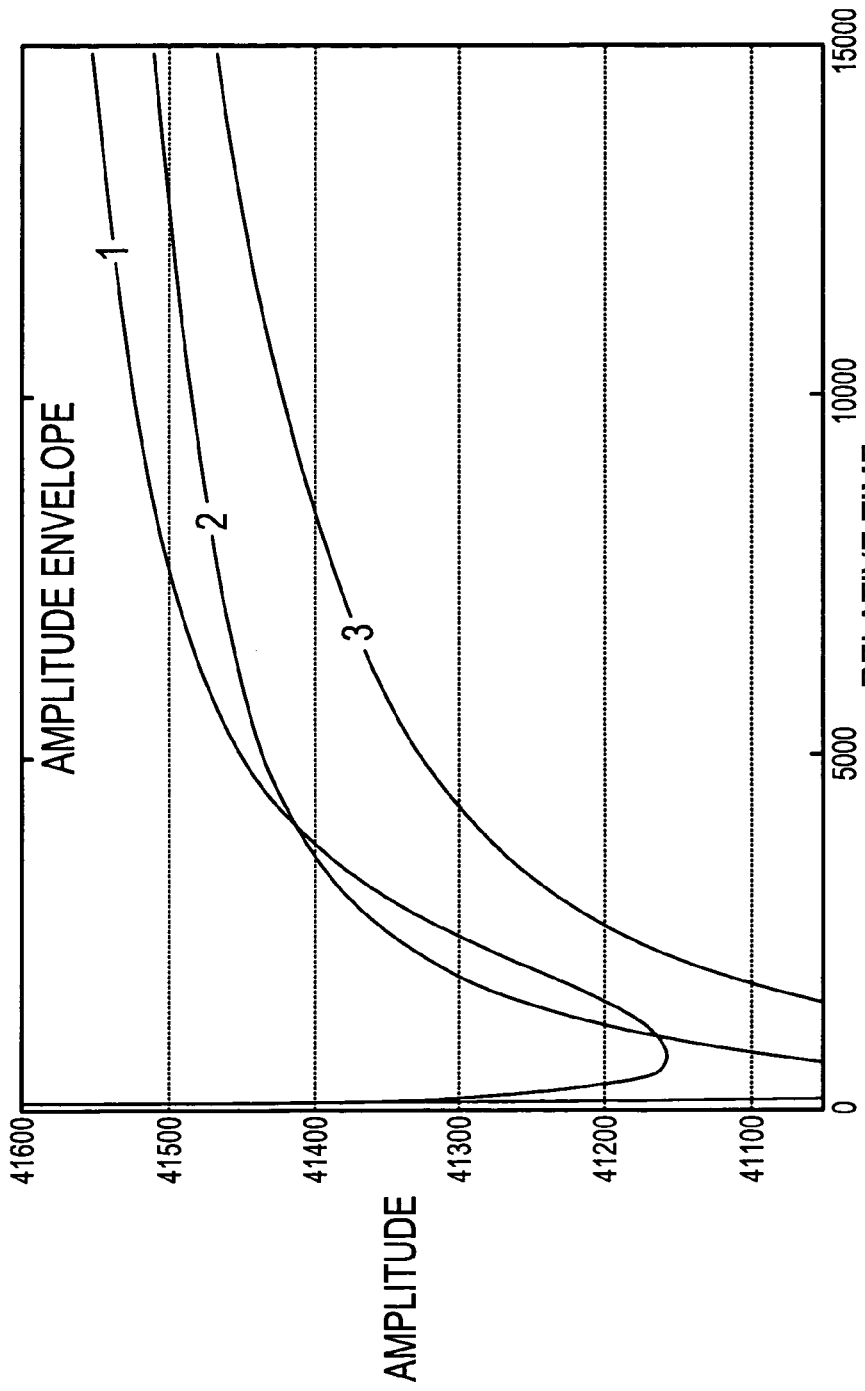
FIG. 28A shows a plot of lower extrema data.
Figure 28B:
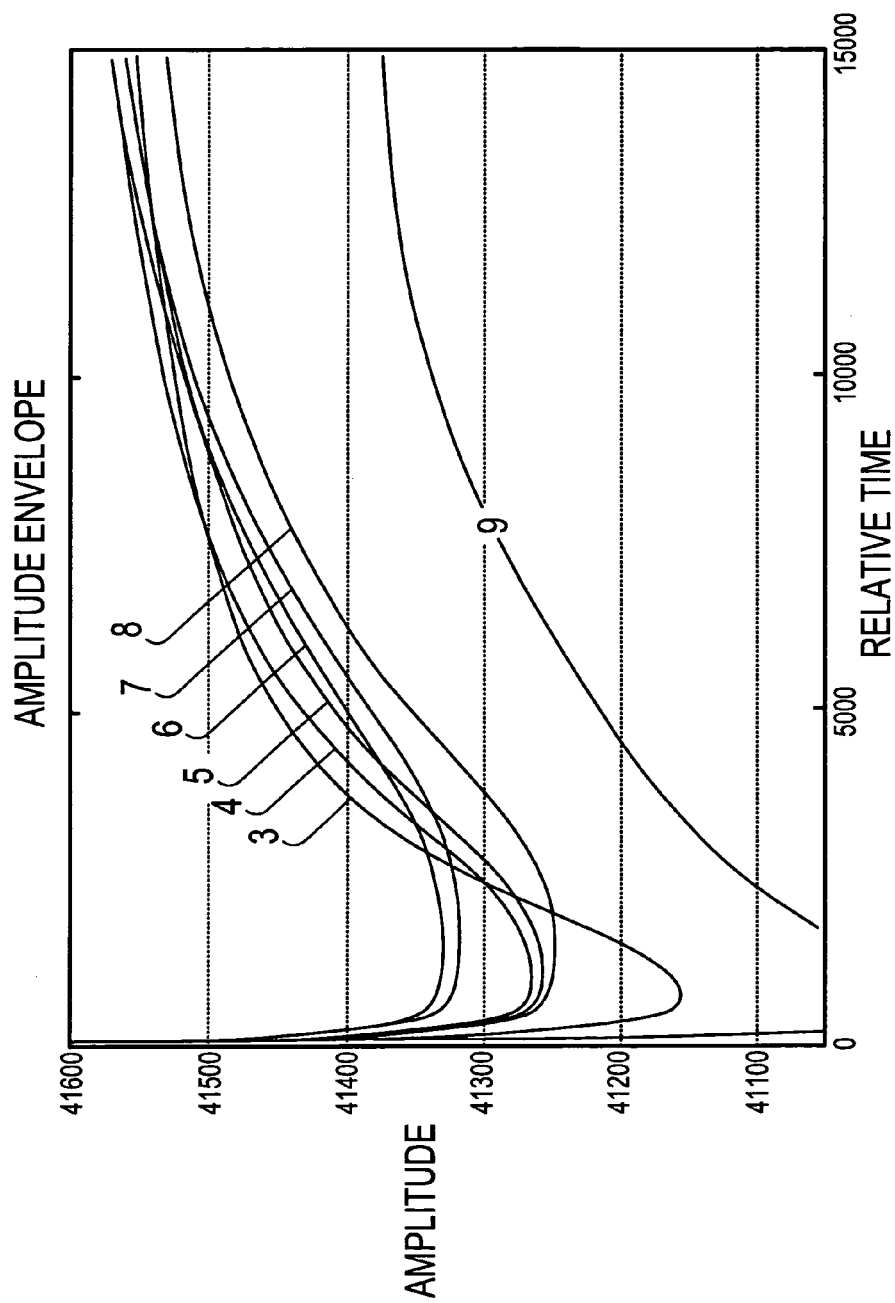
FIG. 28B shows a plot of lower extrema data.

In the lower envelope, the characteristic of most importance is the location (the value alone the 'y' time axis) of the ascending portion of the curve following the inflection point as the slope becomes positive: as the cell's state of charge is reduced (i.e., progressively discharged), this ascending (and almost linear on the semi-log plot) portion moves toward the right, that is, occurs later in time following the onset of discharge excitation. This orderly progression continues until the cell nears the end of its life, whereupon the lower curve begins to move downward radically, indicating that the cell cannot sustain the discharge current. The lower extrema data from all the tests are compiled in FIGS. 28A and 28B. Note that the initial points of plots 1 and 2 fall well below the edge of the graph: this indicates substantial passivation, as expected since these data were obtained from the cell prior to any substantial discharging.

Figure 29A:
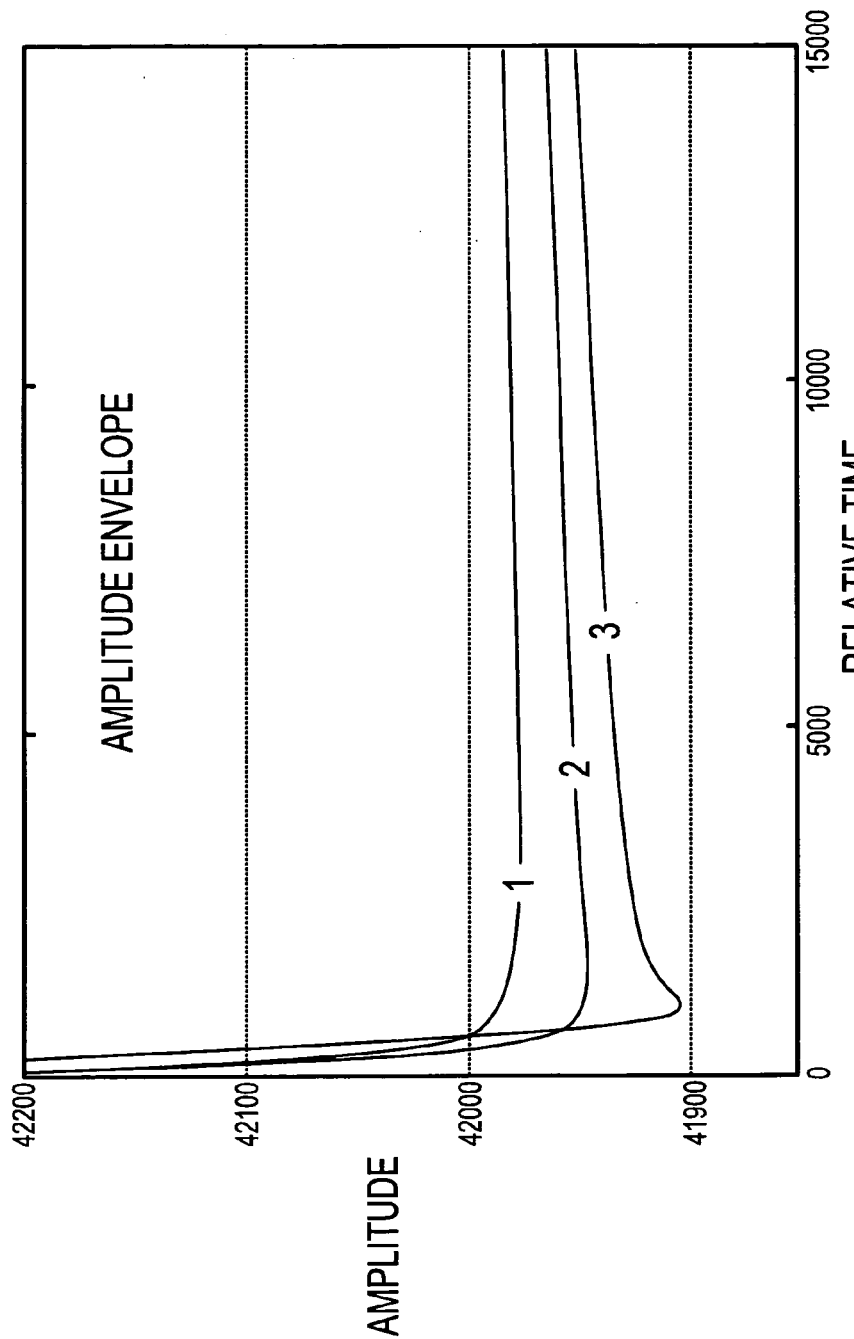
FIG. 29A shows a plot of upper extrema data.
Figure 29B:
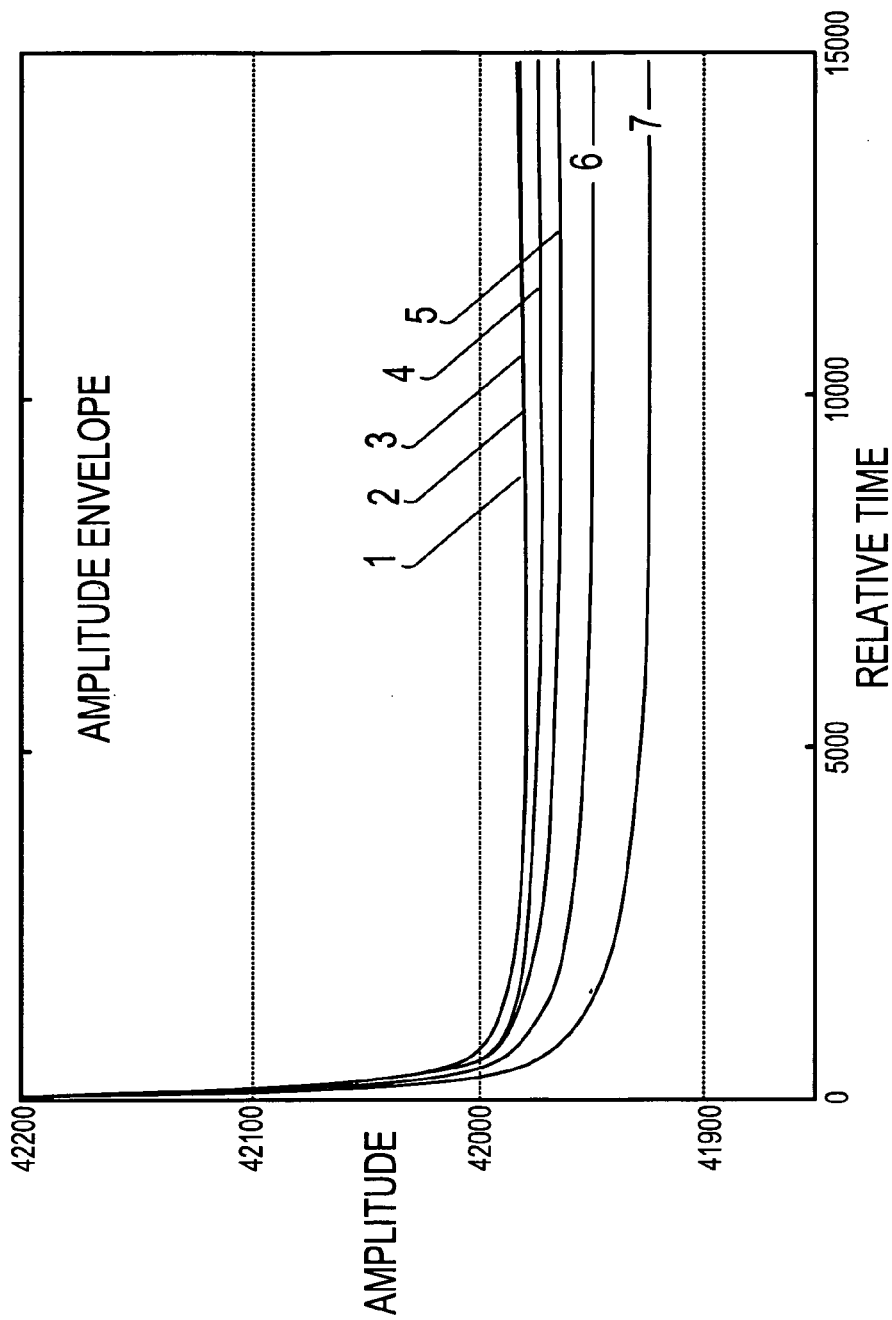
FIG. 29B shows a plot of upper extrema data.

Throughout most of the cell's life, the upper extrema envelope is seen to hold a more stable value than the lower margin (depending of course on the amplitude of the discharge current). As the cell approaches complete discharge, the average DC value of the upper envelope begins to decrease. The size of this decrement, as seen in FIGS. 29A and 29B, can then be used in conjunction with the lower extrema information as an effective indicator of state of charge toward the end of cell life.

Advantages Conferred by the Disclosed Method

State of charge can be accurately determined on the basis of a selected small number of raw data points taken from measurements on an unknown cell, and then compared to previously stored baseline values. This data reduction technique can be economically implemented by using a triggerable sampler which takes data only at the pre-specified times (stored in local microcomputer memory, or within an ASIC or similar device) during the test sequence. The basic discharge/rest excitation method permits both the cell's 'loaded terminal voltage', and 'recovery terminal voltage' to be obtained (essentially simultaneously) during a single test protocol. From these data, both the upper and lower amplitude envelope extrema can be extracted, allowing high resolution state of charge estimation for cells at any charge condition. Defective or severely depleted cells can be detected early on (within 100 microseconds) during the first discharge pulse. If a 'defective' or 'discharged' determination is made, testing may be terminated in a timely fashion, prior to catastrophic failure of the cell. When sufficiently high-speed sampling is employed (fast enough to capture the electrochemical events of interest in a specific application), cell failure mechanisms can be identified.

Brand new cells, or partially depleted (used) cells that have become considerably passivated due to extended storage times, can be detected within a few tens of microseconds, and the excitation current can be increased accordingly for a few cycles to remove the passivation and then subsequently reduced, yielding more accurate test results and state of charge determination. The pulse/rest method permits relatively high current to be employed (as compared to the cell's nominal 'C' rate), permitting shorter test periods as compared with traditional DC discharge/open-circuit techniques. The present method employs an equivalent excitation frequency of 0.762 Hz. However, this may be modified to suit particular applications. The Present method employs a 50% duty cycle excitation, however this ratio may be modified to suit particular applications. The present method employs an alternating sequence of constant amplitude discharge pulses and rest periods. However, the composition of the excitation sequence may be modified (e.g., varying the amplitude of successive pulses) to suit particular applications.

The method can be extended to apply to secondary (rechargeable) cells, by redefining the excitation to include charging pulses, interleaved appropriately with discharge and rest pulses. In this case, the amplitude envelope extrema will consist of four components: 'discharging terminal voltage'; 'recovery-after-discharge terminal voltage'; 'charging terminal voltage'; and 'recovery-after-charge terminal voltage'. The former pair permits evaluation of the cell's ability to deliver energy, while the latter pair provides an estimate of the cell's energy (charge) acceptance capability, which is very important when this method is used within, for example, a charger or a UPS.

The extended test method (charge/rest/discharge excitation) can be implemented directly within a rapid pulse-type charger, where the charging waveform is appropriately modulated to serve directly as the testing waveform. The measurement method may take the form of: software (embedded in a system which already provides the necessary hardware); a stand-alone instrument; an embedded controller or test subsystem; an integrated circuit or chip set. The method may be used to implement diagnostic tools for commercial cell test and evaluation, or in a precision configuration (device) intended for diverse analytic, electrochemical laboratory applications. The extended method may be used to enhance speed and efficiency in 'forming charge' applications, wherein a newly manufactured cell/battery is first charged. The present method may be generalized to operate with many cell/battery sizes and chemistries. The present method may be used to assist or control various commercially available battery systems, chargers, battery cyclers and battery evaluation/qualification devices.

Various signal processing and/or data analysis methods or algorithms may be applied, in various combinations, to excitation-response time-series data to analyze or otherwise generally characterize, the underlying electrochemical processes within the cell. Such methods may be parametric and/or nonparametric, may apply mathematical/numerical transformations of data (e.g. Fourier, Laplace, etc.), may apply signal decompositions, and/or other processing methods. These methods may be designed to extract information contained in the data, estimate/infer parameters of the system under test, for example by calculating basic parameters such as relative amplitude, bias, slopes, curvature, etc., or by fitting (as by numerical minimization of an error function) of measured or derived data to parameterized models. One example of the latter case is the estimation of time constants and initial conditions of "steady-state" transient response waveforms by fitting to parameterized model consisting of a sum of exponentials.

For such analysis, this technique is far superior to traditional Frequency Response Analysis, with its protracted measurement times, and the necessity for positing arbitrary equivalent electric circuits as a heuristic or predictive aid regarding the underlying electrochemical phenomena. The present method will allow assessment of the 'rechargeability', of an unknown cell (i.e., it won't try to charge a lithium primary, type, which is dangerous), and with suitable baseline data, allow immediate identification of various cell chemistries.

As described above, the methods described above may be embodied in the form of computer-implemented processes and apparatuses for practicing those processes. In addition, these methods may also be embodied in the form of computer program code containing instructions embodied in tangible media, such as floppy diskettes, CD-ROMs, hard drives, or any other computer-readable storage medium, wherein, when the computer program code is loaded into and executed by a computer, the computer becomes an apparatus for practicing the invention. Existing systems having reprogrammable storage (e.g., flash memory) may be updated to implement the invention. Furthermore, these methods may also be embodied in the form of computer program code, for example, whether stored in a storage medium, loaded into and/or executed by a computer, or transmitted over some transmission medium, such as over electrical wiring or cabling, through fiber optics, or via electromagnetic radiation, wherein, when the computer program code is loaded into and executed by a computer, the computer becomes an apparatus for practicing the invention. When implemented on a general-purpose microprocessor, the computer program code segments configure the microprocessor to create specific logic circuits.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the scope thereof. Therefore, it is intended that the invention not be limited to the particular embodiment disclosed as the best mode contemplated for carrying out this invention, but that the invention will include all embodiments falling within the scope of the appended claims. Moreover, unless specifically stated any use of the terms first, second, etc. do not denote any order or importance, but rather the terms first, second, etc. are used to distinguish one element from another.

What we claim is:

1. A method for determining characteristics of a system under test (SUT) comprising the steps of:
   providing, by an excitation means, a time-varying current-mode electrical excitation to a system under test, which time varying signal comprises a periodic or quasi-periodic waveform;
   detecting, by a detection means, the conjugate electrical response elicited from the system under test by the excitation;
   converting the detected response from an analog signal into a digital response signal by means of an analog-to-digital conversion means, controlled by a synchronous sampling clock controlling means; and
   performing at least one predetermined analysis of the digital response signal to determine at least one characteristic of the system under test;
   wherein the characteristics of the excitation signal are adjustable, said characteristics including:
   the amplitude of the excitation that is comprised of one or more waveforms that are generated either by analog circuitry means, or digital circuitry means;
   the duration of each portion of a waveform, where a portion of a waveform is bounded at each of it's end points by either zero crossing corresponding to a change of relative polarity, or by a zero amplitude value;
   the relative phase, with respect to a separate reference clock signal, of each waveform comprising the excitation signal.

2. The method of claim 1, wherein the system under test may be one of:
   a chamber that is suitably disposed to receive an analyte and is equipped with at least two electrical members, at least one of which serves as a collector electrode and at least another serves as an emitter electrode; and
   an electrochemical accumulator, comprising at least one cell, which is provided with terminals to which excitation and sense test signal connections can be effected.

3. The method of claim 1, wherein the analog-to-digital conversion means is an Analog to Digital converter controlled by a separate synchronous sampling-clock, said sampling clock being responsive to a separate clock source operative in accordance with a pre-determined sampling schedule.

4. The method of claim 1, wherein the excitation may take the form of either a current or a voltage and the time-varying excitation signal may comprise, in any order, either at least one of, or a consecutively emitted plurality of any combination of, the following waveforms:
   a cycle comprising portions, which may occur in either order, of a period of discharging, that is, negative, current, followed by a period of zero current, the duty-cycle ratio of each of which cycles may be adjusted independently from cycle to cycle, wherein the boundary point between said portions represents the end point and beginning point of the leading and trailing waveform portions respectively;
   a cycle comprising portions, which may occur in either order, of a period of charging, that is, positive, current, followed by a period of zero current, the duty-cycle ratio of which cycles may be adjusted independently from cycle to cycle, wherein the boundary point between said portions represents the end point and beginning point of the leading and trailing waveform portions respectively; and
   a cycle comprising portions, which may occur in either order, of a period of charging, that is, positive, current followed by a period of discharging, negative current, the duty-cycle ratio of which cycles may be adjusted independently from cycle to cycle, wherein the boundary point between said portions represents the end point and beginning point of the leading and trailing waveform portions respectively.

5. The method of claim 1, wherein the electrical excitation is a periodic time varying signal comprising one or more whole waveform cycles having substantially identical amplitude, polarity and duration characteristics.

6. The method of claim 1, wherein the electrical excitation is a quasi-periodic time varying signal comprising a plurality of waveform cycles, at least two of which cycles have at least one distinctly different characteristic, which characteristics may include the amplitude of a part-cycle or the duration of a part-cycle, or the relative polarity of corresponding part-cycles.

7. The method of claim 1, wherein the time-varying current excitation signal exhibits a plurality of abrupt discontinuities and comprises one or more waveforms, which waveform may be any of:
   a rectilinear waveform, exhibiting a leading edge that constitutes an abrupt amplitude transition, followed by a substantially constant-amplitude portion, followed by another abrupt amplitude transition representing a trailing edge;
   a ramping waveform comprising, in either order, an abrupt amplitude step representing an abrupt amplitude and a portion whose amplitude varies with time in a linear fashion, thus exhibiting a constant, but non-zero, first derivative with respect to time; and
   a triangle waveform comprising two distinct adjacent ramping segments each exhibiting a separate non-zero slope and whose adjacent ends are coincident at a point whereat the value of the slope of the waveform exhibits an abrupt transition.

8. The method of claim 1, wherein, over the course of a test event, the time average of the excitation current is non-zero so that either, the DUT is excited with a net positive current representing charging, the DUT is excited with a net negative current representing discharging.

9. The method of claim 1, where in the range of achievable excitation amplitudes may be sufficiently wide to allow both:
   non-invasive testing, wherein no irreversible changes are wrought on the system or device under test; and
   invasive testing, wherein irreversible changes are wrought on the system or device under test.

10. The method of claim 1, wherein at the step of performing, a point-to-point averaging technique is applied as follows to reduce noise in the data:
   when response data obtained from the system under test indicates, by the lack of any slowly varying offset/bias component in the response signal, that it is substantially in a state of equilibrium, noise reduction is achieved by performing point-to-point averaging directly on corresponding data points obtained from a plurality of consecutive response cycles, to obtain a single cycle of averaged data points; or
   when response data obtained from the system under test indicates by the presence of a slowly varying offset/bias component that exhibits a substantially constant slope over a plurality of response cycles, noise reduction is achieved by first determining the nature of the slowly-time-varying offset, then removing, by subtraction, the contribution of said offset from each response data point to obtain a series of compensated data points, and finally performing point-to-point averaging directly on the compensated data point obtained during said plurality of consecutive response cycles, to obtain a single cycle of averaged data points.

11. The method of claim 3, wherein at least one collector electrode and one emitter electrode each also serve as sense electrodes.

12. The method of claim 2, wherein additional electrical members are provided that serve as sense electrodes distinct from the collector and emitter electrodes.

13. The method of claim 2, wherein the sense electrodes are suitably positioned with respect to the separate excitation electrodes, to function in the manner of a Kelvin sense connection.

14. The method of claim 1, wherein the chamber contains, in addition to the analyte, a separate medium provided to permit the flow of electric current between the analyte and the other electrodes.

15. The method of claim 1, wherein the system under test corresponds to an electrochemical accumulator and the excitation comprises one or more complex pulse-type excitation signals characterized by alternating periods of discharging current and zero current to the cell.

16. The method of claim 1, wherein the systems under test comprises an accumulator, and the conjugate response signal represents the time-varying cell polarization voltage developed between the terminals of the accumulator due to a current mode excitation, and said time-varying cell polarization voltage information is analyzed to determine at least one characteristic of the accumulator, which characteristic may include:
   the relative state of charge of the accumulator;
   the relative state of health of the accumulator;
   the relative degree of passivation exhibited by the accumulator;
   the real component of the accumulator's complex impedance or conductance, as a function of frequency;

the imaginary component of the accumulator's complex impedance or conductance, as a function of frequency; or a specific failure or error condition in the accumulator.

17. The method of claim 1, wherein the value of the first time-derivative of the time-varying polarization voltage response is computed for at least one portion of the time-dependent polarization voltage data, and used to determine at least one characteristic of the accumulator, which characteristic may include:

the relative state of charge of the accumulator;
the relative state of health of the accumulator;
the relative degree of passivation exhibited by the accumulator;
a specific failure or error condition in the accumulator.

18. The method of claim 1, wherein at the step of performing the analysis may be any of:

the determination of the presence, at a minimal concentration, of a least one particular analyte or chemical substance contained with a test chamber;

the determination of the concentration of at a least one particular analyte or chemical substance contained with a test chamber; and the determination of the quantity of at least one particular analyte or chemical substance contained within the test chamber; and wherein the excitation is periodic, the calculation of the Fourier or LaPlace transforms of the digitally represented excitation and response data, which transforms may be further manipulated to yield the corresponding complex impedance spectrum;

the extraction of information from results of at least one previous analysis, allowing a characterization of at least one equivalent circuit model that describes the underlying electrochemical system;

the determination of asymmetries between the positive and negative parts of the response waveform, or sets of part-cycles that have been subjected to point-by-point averaging to achieve noise reduction, said asymmetries representing hysteresis effects indicating disparities of forward and backwards reactions occurring within the analyte;

the determination of amplitude extrema contour curves;

the determination of slowing changing bias conditions within the DUT, through the application of sliding-average or other low-pass filtering methods;

the determination of transitions between linear and non-linear response regimes within the DUT, and therefrom determine reaction-point thresholds; and the extraction of information from results of at least one previous analysis, allowing a characterization of at least one underlying electrochemical process that occurs within the electrochemical system in response to the excitation.

19. The method of claim 2, wherein the analyte has been modified to incorporate an electrochemically sensitive marker component.

20. An apparatus disposed to perform electrical and electrochemical measurements comprising at least:

an excitation driver;
an excitation receiver;
a response sensing preamplifier;
a synchronous sampling means; and
suitable means of interconnection to a system or device under test, whereby an excitation signal may be forced to flow through said system or device, and the resultant conjugate response signal detected and conveyed to the preamplifier operatively connected to a synchronous sampling means.

21. The apparatus of claim 20, wherein the excitation driver is either:

disposed to emit a current-mode signal, while the excitation received is disposed to receive a current-mode signal, and the preamplifier is disposed to detect a voltage-mode response; or disposed to emit a voltage-mode signal, while the excitation received is disposed to receive a voltage-mode signal, and the preamplifier is disposed to detect a current-mode response.

22. The apparatus of claim 20, wherein the synchronous sampling means operates according to a pre-determined sampling schedule such that:

sampling may commence concurrently with an abrupt excitation transition and proceed according to a predetermined set of time delay values;

sampling may commence, or re-commence, at any boundary point between the portions of an excitation cycle and proceed therefrom according to a predetermined set of time delay values; and sampling may be preformed on both the excitation signal and the response signal.

23. The apparatus of claim 20, wherein a chamber is disposed to receive an analyte, and said chamber is equipped with electrodes suitably disposed for providing an excitation signal to, and detecting a response signal from, the analyte.

24. The apparatus of claim 22, wherein the electrodes within a test chamber are configured to provide a Kelvin connection with respect to the analyte.

* * * * *